United States Patent
Jacobs, Jr. et al.

(10) Patent No.: US 12,150,986 B2
(45) Date of Patent: Nov. 26, 2024

(54) HSV-2-DELTA-gD VACCINES AND METHODS FOR THEIR PRODUCTION AND USE

(71) Applicant: Albert Einstein College of Medicine, Bronx, NY (US)

(72) Inventors: William Jacobs, Jr., Pelham, NY (US); Betsy Herold, Rowayton, CT (US); Joseph Dardick, Bronx, NY (US); Kayla A. Weiss, Bronx, NY (US)

(73) Assignee: ALBERT EINSTEIN COLLEGE OF MEDICINE, Bronx, NY (US)

( * ) Notice: Subject to any disclaimer, the term of this patent is extended or adjusted under 35 U.S.C. 154(b) by 0 days.

(21) Appl. No.: 18/071,109

(22) Filed: Nov. 29, 2022

(65) Prior Publication Data

US 2023/0293674 A1    Sep. 21, 2023

Related U.S. Application Data

(63) Continuation of application No. 17/051,992, filed as application No. PCT/US2019/030259 on May 1, 2019, now abandoned.

(60) Provisional application No. 62/665,050, filed on May 1, 2018.

(51) Int. Cl.
| | | |
|---|---|---|
| A61K 39/245 | (2006.01) | |
| C07K 1/13 | (2006.01) | |
| C12N 7/00 | (2006.01) | |
| C12N 15/10 | (2006.01) | |

(52) U.S. Cl.
CPC .............. *A61K 39/245* (2013.01); *C07K 1/13* (2013.01); *C12N 7/00* (2013.01); *C12N 15/102* (2013.01); *C12N 2710/16034* (2013.01)

(58) Field of Classification Search
CPC .............. A61K 2039/505; A61K 39/12; A61K 2039/5258; A61K 2039/5254; A61K 2039/6075; A61K 35/763; A61K 39/245; A61K 39/42; C07K 14/005; C12N 7/00; C12N 15/86; C12N 2710/16622; C12N 2710/16634
See application file for complete search history.

(56) References Cited

U.S. PATENT DOCUMENTS

| | | | |
|---|---|---|---|
| 2008/0118530 A1* | 5/2008 | Kew ........................ | A61P 37/00 424/274.1 |
| 2013/0028924 A1 | 1/2013 | Ertl et al. | |
| 2013/0136768 A1* | 5/2013 | Picker ................... | A61K 39/275 435/320.1 |
| 2015/0232812 A1 | 8/2015 | Coffin | |
| 2016/0158343 A1 | 6/2016 | Jacobs, Jr. et al. | |
| 2017/0202952 A1 | 7/2017 | Jacobs, Jr. et al. | |

FOREIGN PATENT DOCUMENTS

| | | |
|---|---|---|
| WO | 2005049845 A2 | 6/2005 |
| WO | 2005049846 A2 | 6/2005 |
| WO | 2015134368 A2 | 9/2015 |

OTHER PUBLICATIONS

Roychoudhury S, Mukherjee D. A detailed comparative analysis on the overall codon usage pattern in herpesviruses. Virus Res. Mar. 2010;148(1-2):31-43. Epub Dec. 5, 2009. (Year: 2009).*
Shen Y, Lai T, Campbell RE. Red fluorescent proteins (RFPs) and RFP-based biosensors for neuronal imaging applications. Neurophotonics. Jul. 2015;2(3):031203. Epub Jun. 19, 2015. (Year: 2015).*
Yao XD, Elias P. Recombination during early herpes simplex virus type 1 infection is mediated by cellular proteins. J Biol Chem. Jan. 26, 2001;276(4):2905-13. Epub Nov. 7, 2000. (Year: 2000).*
Ackerman, M. et al.; "A robust, high-throughput assay to determine the phagocytic activity of clinical antibody samples"; Journal of Immunological Methods, vol. 366, Issues No. 1-2; 2011; pp. 8-19; doi:10.1016/j.iim.2010.12.016.
Bouvier, et al., "Animal Models for Influenza Virus Pathogenesis and Transmission" Viruses 2010, vol. 2 (1530-1563).
Burn, C. et al.; "A Herpes Simplex Virus (HSV)-2 Single-Cycle Candidate Vaccine Deleted in Glycoprotein D Protects Male Mice From Lethal Skin Challenge With Clinical Isolates of HSV-1 and HSV-2"; The Journal of Infectious Diseases, vol. 217; 2018; pp. 754-758.
Cheshenko, et al., "HSV Activates Akt to Trigger Calcium Release and Promote Viral Entry: Novel Candidate Target for Treatment and Suppression", The FASEB Journal, vol. 27(7), Jul. 2013, pp. 2584-2599.
Dardick, J. et al.; "A novel vaccine vector: herpes simplex virus type-2 deleted in glycoprotein D (HSV-2 ΔgD) and expressing modified influenza A (IAV) hemagglutinin (HA) antigens"; Journal of Immunology, vol. 198, 1 Supplement; 2017; 5 pages.
Davis, A.R. et al.; "High throughput method for creating and screening recombinant adenoviruses"; Gene Therapy, vol. 5; 1998; pp. 1148-1152.
Eisenberg, et al., "Amino-Terminal Sequences of Glycoprotein D of Herpes Simplex Virus Types 1 and 2" Journal of Virology, Jan. 1984, vol. 49, No. 1 (265-268).
European Search Report for European Application 19796848.0 [PCT/US2019/030259] dated May 25, 2022; 3 pages.
Fusco, et al., "The pro-fusion domain of herpes simplex virus glycoprotein D (gd) interacts with the gD N terminus and is displaced by soluble forms of viral receptors" PNAS, vol. 102, No. 26 (Jun. 28, 2005) (9323-9328).
Gibson, et al., "Enzymatic assembly of DNA molecules up to several hundred kilobases" Nature Methods, May 2009, vol. 6, No. 5 (343-347).
Haynes, et al., "Immune-Correlates Analysis of an HIV-1 Vaccine Efficacy Trial" The New England Journal of Medicine, Apr. 5, 2012, vol. 366, No. 14 (1275-1286).
He, et al., "Epitope specificity plays a critical role in regulating antibody-dependent cell-mediated cytotoxicity against influenza A virus" PNAS, Oct. 18, 2016, vol. 113, No. 42 (11931-11936).

(Continued)

*Primary Examiner* — Rachel B Gill
(74) *Attorney, Agent, or Firm* — CANTOR COLBURN LLP

(57) ABSTRACT

Recombinant herpes simplex virus 2 (HSV-2) vaccine vectors, compositions and vaccines comprising such, and methods of use thereof are each provided.

19 Claims, 25 Drawing Sheets

Specification includes a Sequence Listing.

(56) References Cited

OTHER PUBLICATIONS

International Search Report and Written Opinion for International Application PCT/US2019/030259; International Filing Date: May 1, 2019; Date of Mailing: Jul. 17, 2019; 18 pages.

Jegaskanda, et al., "Influenza-Specific Antibody-Dependent Cellular Cytotoxicity: Toward a Universal Influenza Vaccine" The Journal of Immunology, 2014; 193:469-475.

Kantor, et al., "Methods of Gene Transfer to the Central Nervous System" Adv Genet. 2014; 87:125-197; doi:10.1016/B978-0-12-800149-3.00003-2 (67 pgs).

Liao, et al., "Co-evolution of a broadly neutralizing HIV-1 antibody and founder virus" Nature, Apr. 25, 2013, 496 (7446), (469-476).

Mullarkey, et al., "Broadly Neutralizing Hemagglutinin Stalk-Specific Antibodies Induce Potent Phagocytosis of Immune Complexes by Neutrophils in an Fc-Dependent Manner" mBio vol. 7, Issue 5, 2016 (12 pgs).

Nicola, et al., "Structure-Function Analysis of Soluble Forms of Herpes Simplex Virus Glycoprotein D" Journal of Virology, Jun. 1996, vol. 170, No. 6, (3815-3822).

Osterholm, et al., "Efficacy and effectivness of influenza vaccines: a systematic review and meta-analysis" Lancet Infect Dis 2012; vol. 12 (36-44).

Petro, et al., "Herpes simplex type 2 virus deleted in glycoprotein D protects against vaginal, skin and neural disease" Elife 2015;4:e06054 (18 pages).

Petro, et al., "HSV-2 ΔgD elicits FcγR-effector antibodies that protect against clinical isolates" JCI Insight Aug. 4, 2016; vol. 1 (12):e88529.

Schmeisser, et al., "Incorporation of a lambda phage recombination system and EGFP detection to simplify mutagenesis of Herpes simplex virus bacterial artificial chromosomes" BMC Biotechnology 2007, 7:22 (11 pgs).

Vasileiou, et al., "Effectiveness of Influenza Vaccines in Asthma: A Systematic Review and Meta-Analysis" Clinical Infectious Diseases, Oct. 15, 2017, vol. 65 (1388-1395).

Wang, et al., "Incorporation of High Levels of Chimeric Human Immunodeficiency Virus Envelope Glycoproteins into Virus-Like Particles" Journal of Virology, Oct. 2017, vol. 81, No. 20 (10869-10878).

Warden et al., "Herpesvirus BACs: Past, Present, and Future" Journal of Biomedicine and Biotechnology, vol. 2011, Article ID 124595, doi:10.1155/2011/124595 (16 pgs).

Wohlbold, et al., "Vaccination with soluble headless hemagglutinin protects mice from challenge with divergent Influenza viruses", Vaccine, 2015, vol. 33(29), (3314-3321).

Saade et al.; "Technologies for enhanced efficacy of DNA vaccines"; Expert Review of Vaccines, vol. 11, Issue No. 2; 2012; pp. 189-209; DOI: 10.1586/erv.11.188.

Xu, Z. et al.; "Effect of Plasmid Dosage and Immunization Occasions on Immune Response Induced by Gene-gun Delivered DNA Vaccine"; Chinese Journal of Biologicals, vol. 23, Issue No. 6; pp. 609-612 (English Abstract).

* cited by examiner

MKANLLVLLCALAAADADTICIGYHA(NNST)DTVDTVLEK(NVT)VTHSVNLLEDSHNG
KLCRLKGIAPLQLGKCNIAGWLLGNPECDPLLPVRSWSYIVETPNSENGICYPGDFIDYEE
LREQLSSVSSFERFEIFPKESSWPNHNTTKGVTAACSHAGKSSFYRNLLWLTEKEGSYPK
LKNSYVNKKGKEVLVLWGIHHPSNSKDQQNIYQNENAYVSVVTSNYNRRFTPEIAERP
KVRDQAGRMNYYWTLLKPGDTIIFEANGNLIAPRYAFALSRGFGSGIITS(NAS)MHECN
TKCQTPLGAI(NSS)LPFQNIHPVTIGECPKYVRSAKLRMVTGLRNIPSIQSRGLFGAIAGFI
EGGWTGMIDGWYGYHHQNEQGSGYAADQKSTQNAINGITNKVNSVIEKMNIQFTAVG
KEFNKLEKRMENLNKKVDDGFLDIWTYNAELLVLLENERTLDFHDSNVKNLYEKVKSQ
LKNNAKEIGNGCFEFYHKCDNECMESVR(NGT)YDYPKYSEESKLNREKVDGVKLESM
GIYQILAIYSTVASSLVLLVSLGAISFWMCS(NGS)LQCRICI D*NFRNMRKNTLVST

HA1 Stalk

HA1 Head

HA2 Stalk

HA2 Transmembrane

HA2 Cytosolic

~~Strikethrough~~ = Genetic material after stop codon

Underline = Fusion peptide

*Bold and Italic* = Disulfide bond sites () = Glycosylation Site for PR8 Virus Glycosylation sites vary from virus to virus

FIG. 6

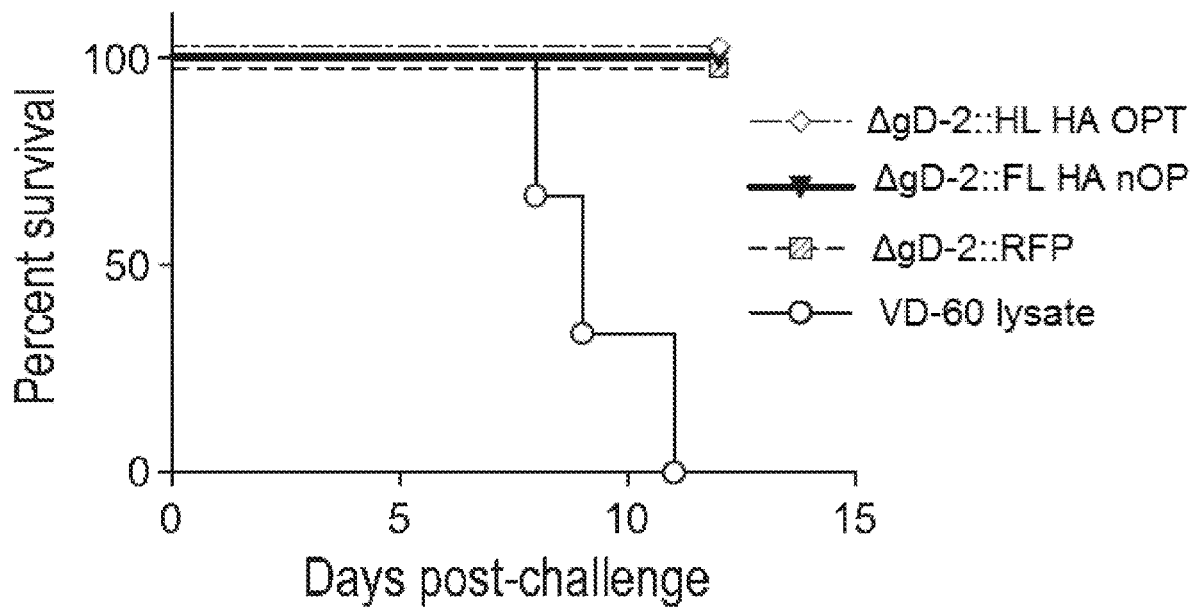
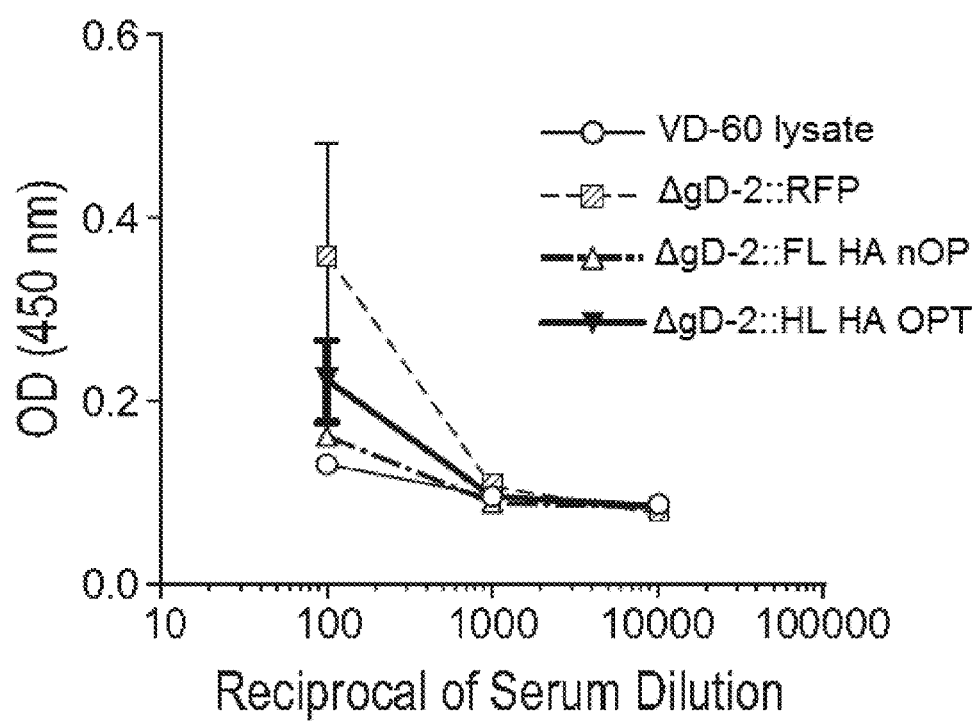
FIG. 8

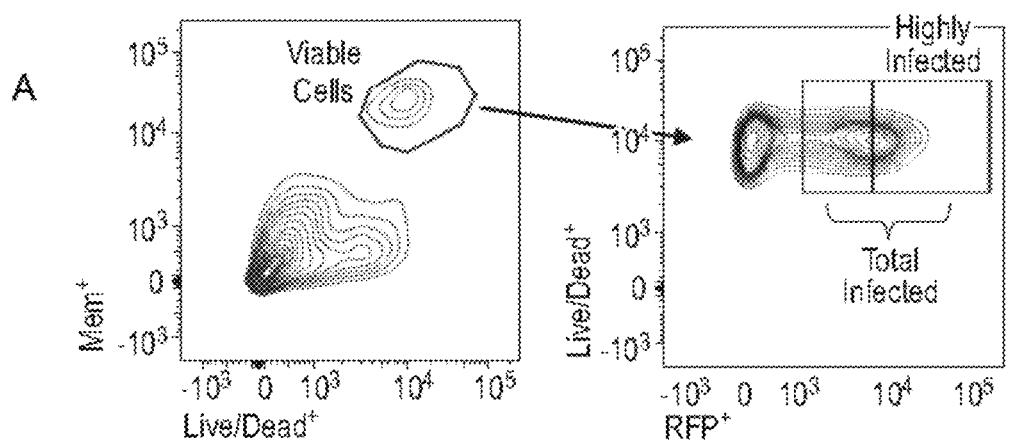
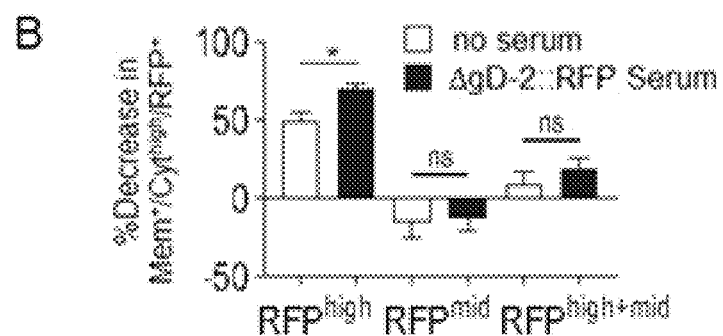
FIG. 15A-15B
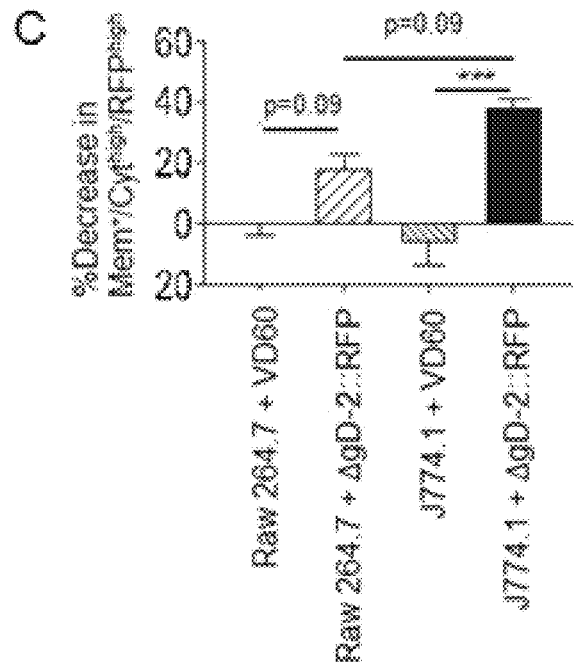
FIG. 15C

HSV-2-DELTA-gD VACCINES AND METHODS FOR THEIR PRODUCTION AND USE

CROSS-REFERENCE TO RELATED APPLICATIONS

This application is a continuation of U.S. application Ser. No. 17/051,992, filed on Oct. 30, 2020, which is a National Stage application of PCT/US2019/030259, filed on May 1, 2019, which claims the benefit of U.S. Provisional Application No. 62/665,050, filed on May 1, 2018, both of which are incorporated by reference herein in their entirety.

STATEMENT OF GOVERNMENT SUPPORT

This invention was made with government support under grant numbers AI117321 and AI007501 awarded by the National Institutes of Health. The government has certain rights in the invention.

BACKGROUND OF THE INVENTION

Pathogen infections, including influenza and HIV viral infections, have a massive impact on global health. Vaccines have been developed for many pathogens, including both influenza and HIV viral infections, however they have failings and limitations. Thus, a novel vaccine strategy must be engineered and evaluated.

SUMMARY OF THE INVENTION

Disclosed herein are new and improved HSV-2-based vaccines for various antigenic targets, including influenza and HIV.

A process is provided for producing a vaccine vector directed against a heterologous antigen, the process comprising:
  a) providing an HSV-2 genome comprising:
    (i) a fully or partially deleted in a gene encoding HSV-2 glycoprotein D, and
    (ii) a nucleic acid comprising a promoter-FP construct, wherein FP is a nucleic acid encoding a fluorescent protein;
  b) co-transfecting a host cell with (i) the HSV-2 genome of a) and (ii) a linear DNA fragment encoding the heterologous antigen under conditions whereby allelic recombination occurs between the HSV-2 genome and the DNA fragment;
  c) screening plaques resulting from b) to identify plaques not showing fluorescence under excitation light which elicits fluorescent protein fluorescence;
  d) recovering from those plaques not showing fluorescence in c) recombinant HSV-2 viruses or virions so as to obtain a vaccine vector directed against the heterologous antigen.

Also provided is a recombinant herpes simplex virus-2 (HSV-2) having a genome encoding a heterologous antigen made by the process described herein.

Also provided is a recombinant herpes simplex virus-2 (HSV-2) having (i) a complete deletion of an HSV-2 glycoprotein D-encoding gene (referred to as ΔgD-2) in the genome thereof and (ii) (a) encoding: a promoter, a heterologous antigen signal sequence, a heterologous antigen or (b) encoding: a promoter, a heterologous antigen.

Also provided is a recombinant herpes simplex virus-2 (HSV-2) having (i) a partial deletion of an HSV-2 glycoprotein D-encoding gene in the genome thereof and (ii) (a) encoding, in order, an HSV-2 gD signal sequence, a heterologous antigen, an HSV-2 gD transmembrane domain, optionally an HSV-2 gD cytosolic domain, but not encoding an HSV-2 gD extracellular domain, or (b) encoding, in order, an HSV-2 gD signal sequence, a heterologous antigen, and transmembrane cytoplasmic tail of HSV-2 gD.

Also provided is an isolated cell comprising therein a recombinant HSV-2 virus as described herein, wherein the cell is not present in a human being.

Also provided is a vaccine composition comprising the recombinant HSV-2 virus as described herein.

Also provided is a pharmaceutical composition comprising a recombinant HSV-2 virus as described herein, and a pharmaceutically acceptable carrier.

Also provided is a method of eliciting and/or enhancing an immune response in a subject comprising administering to the subject an amount of (i) a recombinant HSV-2 virus as described herein; (ii) a vaccine as described herein; or (iii) a pharmaceutical composition as described herein, in an amount effective to elicit and/or enhance an immune response in a subject.

Also provided is a method of treating or reducing the likelihood of an influenza infection in a subject comprising administering to the subject an amount of (i) a recombinant HSV-2 virus as described herein; (ii) a vaccine as described herein; or (iii) a pharmaceutical composition as described herein, in an amount effective to treat or reduce the likelihood of an influenza infection in a subject.

Also provided is a method of treating or reducing the likelihood of an HIV infection in a subject comprising administering to the subject an amount of (i) a recombinant HSV-2 virus as described herein; (ii) a vaccine as described herein; or (iii) a pharmaceutical composition as described herein, in an amount effective to treat or reduce the likelihood of an HIV infection in a subject.

Also provided is a method of vaccinating a subject for influenza infection comprising administering to the subject an amount of (i) a recombinant HSV-2 virus as described herein; (ii) a vaccine as described herein; or (iii) a pharmaceutical composition as described herein, in an amount effective to vaccinate a subject for influenza infection.

Also provided is a method of vaccinating a subject for HIV infection comprising administering to the subject an amount of (i) a recombinant HSV-2 virus as described herein; (ii) a vaccine as described herein; or (iii) a pharmaceutical composition as described herein, in an amount effective to vaccinate a subject for HIV infection.

Also provided is a method of quantitating a rate or amount of antibody-dependent cell-mediated killing (ADCK) in a population of cells comprising infecting a plurality of cells of the population of cells with a fluorescent protein-expressing recombinant HSV-2 that comprises a genome deleted for the gene encoding HSV-2 gD, under conditions permitting expression of the fluorescent protein in the cells, contacting the plurality of infected cells with an antibody-containing solution and a population of immune cells, and quantitating at one or more time points the amount of cells exhibiting fluorescent protein fluorescence and, optionally, one or more markers, so as to quantitate over time the amount of live infected cells, so as to thereby quantitating the rate or amount of ADCK in the population of cells.

BRIEF DESCRIPTION OF THE DRAWINGS

RFP) genomic DNA and verified with PCR. FIG. 1A Purified pYUB2169 containing the desired gD::HA gene was cut with PacI and co-transfected into VD60 cells alongside HSV-2 ΔgD::PEF1α-RFP genomic DNA. Electroporation was used. Resultant RFP-plaques were purified three times and assessed for the presence of HA. FIG. 1B Recombinant viruses were verified by PCR amplification of the extracellular HA domain from plasmid and recombinant viral DNA. Primers used were located 100 base pairs (bp) upstream and downstream of the extracellular HA domain. Recombinant viruses both showed the desired band, as visualized by comparison to plasmid DNA. No band at that size was present in wells which contained DNA from ΔgD*2 (B3×2.9)(Lanes 1 and 4). Lane 2 shows DNA from pYUB2169 containing full-length HA construct. Lane 3 shows DNA from recombinant HSV-2 ΔgD-2::HA (B3×2.10) containing the non-codon optimized full-length extracellular domain of HA. Lane 5 shows DNA from recombinant HSV-2 ΔgD-2::HAstalk containing the codon-optimized stalk domain of HA. Lane 6 shows DNA from B3×2.11.

FIG. 2 shows antibody response to vaccination with ΔgD-2::GFP (B3×2.7) or ΔgD-2 (B3×2.9).

FIG. 3 shows results of antibody-dependent cellular cytotoxicity of cells infected with ΔgD-2::GFP virus vs. unmarked ΔgD-2 virus.

FIG. 4. T-cell response to ΔgD-2::GFP virus vs. unmarked virus.

FIG. 5. ΔgD-2 vaccination protects against challenge with wild-type HSV-2 strain 4674, similar to protection with ΔgD-2::GFP.

FIG. 6. Construction of chimeric ΔgD-2::HA viruses and immune response in mice. The regions corresponding to the HA1 Stalk region, the HA1 Head region, the HA2 Stalk region, the HA2 Transmembrane region, and the HA2 Cytosolic region are indicated in the amino acid sequence and functional domains of A/Puerto Rico/1934/8 (PR8) HA (SEQ ID NO: 2). For chimeric ΔgD-2::HA viruses, the HA1 stalk, HA1 head (or 4 glycine residues), and HA2 stalk were fused to the transmembrane, cytosolic, and signal sequence domains of HSV-2 (G) gD. For the headless ΔgD-2::HA genes, the HA1 head domain was replaced with 4 glycine residues.

FIG. 7. Presence of chimeric ΔgD-2::HA in recombinant viruses verified by PCR. The lanes as follows: Lane 1: ΔgD-2genomic DNA, Lane 2: ΔgD-2::FL HA nOP genomic DNA, Lane 3: pBJJ1 plasmid DNA, Lane 4: ΔgD-2genomic DNA, Lane 5: ΔgD-2::HL HA nOP genomic DNA, Lane 6: pBJJ2 plasmid DNA. Primers used for PCR amplification were located just upstream and downstream of the HA extracellular domains. No exogenous promoter was inserted into the expression cassette. As a result, chimeric gene expression was regulated by the endogenous promoter.

FIG. 8. Mice vaccinated with ΔgD-2::FL HA nOP (β3χ1) and gD-2::HL HA OPT (β3χ3) are fully protected against HSV-2 challenge but do not form anti-HA IgGs. Mice were prime-boost vaccinated on days 0 and 21 with a control VD60 cell lysate or 1×106 PFU of gD-2::FL HA nOP, gD-2::HL HA OPT, or ΔgD-2::RFP. FIG. 8A. At day 42, mice were challenged with a 10× LD90 of wild type HSV-2 4674. Mice vaccinated with gD-2::FL HA nOP and gD-2::HL HA OPT were fully protected from challenge. FIG. 8B. At day 40 post-prime vaccination, mice were bled to look at serum antibodies. ELISAs performed against soluble PR8 HA show the absence of HA-specific IgGs in mice.

FIG. 9 is a map of pEGFP-N1 expression plasmid. The PCMV::HA::SV40 polyA cassettes were restriction cloned into pBRL812, a plasmid containing >5.5 kB of the HSV-2 (G) genome upstream and downstream of US6. pBRL812 was cut with AsiSI and PacI and co-transfected with ΔgD-2::RFP genomic DNA into VD60 cells. Allelic exchange was identified by lack of RFP expression and RFP negative plaques were picked and purified three times before verification of recombination by PCR.

FIG. 10. Map of the pBRL812 HSV recombination plasmid prepared as described in the above description of FIG. 9.

FIG. 11A. Verification of ΔgD-2::PCMV-FL HA nOP. PCR using primers just upstream and downstream of the PCMV::HA::SV40 PolyA cassette. In FIG. 11A, unlabeled lane: DNA ladder, Lane 1: pJHA1, Lane 2: 1.2.1 potential recombinant isolate, and Lane 3: negative control ΔgD-2 genomic DNA.

FIG. 11B. Verification of ΔgD-2::PCMV-HL HA nOP using PCR using primers just upstream and downstream of the PCMV::HA::SV40 PolyA cassette. Unlabeled lane: DNA ladder, Lane 1: pJHA2, lane 2: 2.2.2 potential recombinant isolate, Lane 3: 2.3.1 potential recombinant isolate, and Lane 4: negative control ΔgD-2 genomic DNA.

FIG. 11C. Verification of ΔgD-2::PCMV-HL HA OPT. PCR using primers just upstream and downstream of the PCMV::HA::SV40 PolyA cassette. Lane 1: pJHA4, Lane 2: 1.2.2 potential recombinant isolate, Lane 3: 1.2.3 potential recombinant isolate, unlabeled lane: DNA ladder. The latter (1.2.3 potential recombinant) isolate was expanded to make the original ΔgD-2::PCMV-HL HA OPT stock.

FIG. 12: ΔgD-2::PCMV-HA recombinant viruses all express HA. VD60 cells were infected with 3 MOI of ΔgD-2::PCMV-FL HA nOP, ΔgD-2::PCMV-HL HA nOP, or ΔgD-2::PCMV-HL HA OPT. At 16 hours post-infection, cells were harvested and stained for HSV-protein and HA expression. HSV protein expression was measured using serum from mice vaccinated with ΔgD-2::RFP. HA expression was measured using monoclonal anti-HA stalk IgG C179. Cells were stained with either cell permeable or cell impermeable methods. Statistics were calculated by student's t test of geometric means between control fluorescence and fluorescence in wells stained for HA expression. Only ΔgD-2::PCMV-FL HA nOP induced high levels of HA expression in infected cell membranes, but all three viruses induced expression as measured by cell-permeable staining.

FIG. 13 shows that ΔgD-2::PCMV-FL HA nOP does not spread from cell to cell.

FIGS. 14A-14E. Kinetics of fluorescent protein expression and infection with HSV-2 ΔgD-2::RFP (ΔgD-2::RFP) compared to the parental HSV-2 ΔgD-2::GFP (ΔgD-2) strain. FIG. 14A. HSV-2 ΔgD-2::RFP (ΔgD-2::RFP) was created by transfecting VD60 cells simultaneously with HSV-2 ΔgD-2::GFP (ΔgD-2) genomic DNA and a plasmid containing pEF1α::RFP flanked on either side by regions homologous to the HSV-2 (G) genome. Homologous recombination between genomic and plasmid DNA yielded ΔgD-2::RFP. Recombinant viruses were isolated by three rounds of plaque purification and verified with PCR and viral genome sequencing. FIGS. 14B and 14C. Vero cells were infected with 1 MOI of HSV-2 ΔgD-2 (B) or ΔgD-2::RFP. Kinetics of infection, RFP expression, and GFP expression were monitored over time. Both viruses show similar kinetics of infection. ΔgD-2 induced very little GFP expression even at 24 hours post-infection while ΔgD-2::RFP induced high levels of RFP expression beginning at 4.5 hours post-infection. FIGS. 14D and 14E. Images show Vero (D) and VD60 (E) cells at 12 hours post-infection with 1 MOI of ΔgD-2::RFP. Infected VD60 cells are forming syncytia, indicative of productive infection. Vero cells have not formed any syncytia. Images taken with deconvolution at 10× magnification.

FIGS. 15A-15C. Validation of novel rapid fluorometric antibody-dependent cell-mediated killing (RFADCK) assay in both Raw 264.7 and J774.1 cells. FIG. 15A. Highly expressing target cells were isolated by flow analysis using dual expression of membrane and live/dead markers. The proportion of cells expressing high levels of HSV proteins was then gated by determining the mean RFP intensity for populations of infected target cells. The percent difference in the proportion of this population between treated and untreated groups was then calculated as ADCK. FIG. 15B. Infected target cells were incubated in the presence or absence of serum from ΔgD-2::RFP prior to co-culture with J774.1 macrophages. Cells were fixed after 12 hours of co-culture and the proportions of RFPhigh and RFPmid target cells were quantified. In assay wells containing serum from ΔgD-2:RFP vaccinated mice, there were significantly fewer RFPhigh cells at the end of the co-culture ($p<0.05$, mean=70.5, 49.3), but not RFPmid or RFPhigh+mid cells. Values represent 3 independent experiments done at least in duplicate. FIG. 15C. ADCK assays were performed in parallel using Raw 264.7 and J774.1 macrophages as effector cells. The number of RFPhigh cells present in co-cultures containing serum from mice vaccinated with ΔgD-2:RFP or VD60 cell lysate were compared to that of co-cultures without serum. Serum from ΔgD-2:RFP vaccinated mice induced more killing in co-cultures containing both Raw 264.7 and J774.1 cells ($p=0.09$, $p<0.001$; mean=18.8%, 38.3%). Data represents three independent experiments done in triplicate with J774.1 and Raw 264.7 cells at effector to target cell ratios of 10:1. Target cells used in all experiments were HEK 293. Statistics in B were done using student's t tests. Statistics in C were done using one-way ANOVA. Error bars reflect SEM. *$p<0.05$; ***$p<0.001$.

FIG. 17A. ADCK assay was carried out using bone marrow-derived macrophages (BMDMs) from both FcγR−/− and WT mice. Baseline killing of infected target cells was determined in co-cultures containing serum from VD60 lysate vaccinated mice. Data represents the percent difference between co-cultures containing serum from ΔgD-2::RFP vaccinated mice and the baseline. At an embodiment effector:target ratio of 10:1, WT BMDMs carried out significantly more ADCK in the presence of HSV-2 ΔgD-2::RFP vaccinated serum than FcγR−/− BMDMs ($p<0.05$). Killing of infected cells by FcγR−/− BMDMs in co-cultures containing serum from ΔgD-2::RFP vaccinated mice was indistinguishable from that of co-cultures containing serum from VD60 lysate mock-vaccinated mice. FIG. 17B. ADCK assay was carried out using BMDMs derived from naïve guinea pig marrow. Baseline ADCK was determined by co-cultures containing serum from naïve animals. An effector:target ratio of 5:1 was used due to limited marrow availability. At this ratio, BMDMs in co-cultures containing pooled serum from ΔgD-2 vaccinated guinea pigs carried out significantly more ADCK than BMDMs in co-cultures containing pooled serum from VD60 mock-vaccinated guinea pigs ($p<0.001$). Each pooled sample contained serum from 6-9 animals. Data represents two independent assays run in triplicate. HEK 293 cells were used as target cells. Statistics were done by student's t test. Error bars reflect SEM. *$p<0.05$; ***$p<0.001$.

FIG. 21A. The mice were bled one-week post-boost and serum neutralization titer was measured against A/Puerto Rico/1934/8 IAV (PR8). Mice immunized with ΔgD-2::HAPR8 developed significant neutralizing Ab titers against PR8 (mean=304). Dotted line represents the limit of detection for the assay. FIGS. 21B and 21C. Three weeks post-boost, mice were challenged intranasally with a 6×LD50 of PR8. Mice were sacrificed when they reached 75% of their initial weight. Mice immunized with ΔgD-2::HAPR8 were fully protected from PR8 challenge while mice that received control vaccinations all succumbed to infection before day 9. Statistics for neutralization titer were calculated by ANOVA. Survival statistics were calculated by Mantel-Cox log-rank test *$p<0.05$; $p<0.01$; *$p<0.001$.

In FIG. 22A, ΔgD-2::RFP DNA was co-transfected into VD60 cells alongside an HA expression cassette containing the hemagglutinin (HA) gene from IAV H1N1 strain A/Puerto Rico/1934/8 (PR8) downstream of PCMV and upstream of a poly-adenylation signal. In FIG. 22B, extracellular and intracellular HA expression was measured by flow cytometry in Vero and VD60 cells infected with 3 MOI of ΔgD-2, ΔgD-2::HAPR8, or ΔgD-2 containing a truncated version of the PR8 HA expression cassette (ΔgD-2::HL HAPR8).

In FIG. 23F, serum from mice immunized with ΔgD-2::HAPR8 induced significant hemagglutination inhibition compared to serum from mice immunized with ΔgD-2 ($p<0.001$; meanHAI titer=80). Mice immunized with ΔgD-2::RFP did not develop any hemagglutination inhibiting antibodies. All graphs show 1 representative experiment with n=5 mice/group. Statistics were calculated using Student's T-test. **$p<0.01$.

FIGS. 24A-24L show that mice immunized with ΔgD-2::HAPR8 develop protection against IAV challenge. Mice were prime-boost immunized 21 days apart with VD60 cell lysate, ΔgD-2, or ΔgD-2::HAPR8, bled at day 28 post-prime, and challenged intranasally 14 days later with a 6× LD50 of IAV. FIGS. 24A-24C, mice immunized with ΔgD-2::HAPR8 developed significant neutralizing titers to PR8 (mean titerPR8=1:304; pVD60<0.01; pΔgD-2<0.05; n=10 mice/group). Mice immunized with ΔgD-2::HAPR8 were also fully protected from weight loss and mortality followed by challenge with PR8 (p<0.001, n=5 mice/group). FIGS. 24D-24F. Mice immunized with ΔgD-2::HAPR8 developed significant neutralizing antibodies against A/California/2009 H1N1 (A/Cal/2009) IAV (mean titerA/Cal=26; pVD60<0.01 pΔgD-2=0.1; n=10 mice/group). Mice immunized with ΔgD::HAPR8 were partially protected from weight loss and mortality following challenge with A/Cal/2009 (p<0.05, n=15 mice/group). As shown in FIGS. 24G-24I, mice immunized with ΔgD-2::HAPR8, ΔgD-2::RFP, or VD60 cell lysate did not develop neutralizing antibody titers against influenza strains A/Victoria/3/75 H3N2 (A/Vic), and A/Aichi/68 H3N2 (X-31) and were not protected from weight loss and mortality following challenge (nneutralization=10 mice/group; nA/Vic challenge=15 mice/group; nX-31 challenge=5 mice/group). Neutralization titers were measured using microneutralization assays against the respective strains. Mice were sacrificed after reaching 70% of starting weight. Statistics for neutralization assays done using 3-way ANOVA tests. Statistics for survival done using Mantel-Cox log-rank tests. *p<0.05; p<0.01; *p<0.001.

In FIGS. 25A and 25B, the mice were bled 1-week post-boost and the serum was analyzed by ELISA. Mice that received ΔgD-2 or ΔgD-2::HAPR8 generated similarly high levels of HSV-specific IgG (FIG. 25A). Additionally, these IgGs were predominantly IgG2c. In FIG. 25C, rapid fluorometric antibody-dependent cell-mediated killing (RFADCK) assay was carried out using the same serum as in FIGS. 25A and 25B. Sera from mice vaccinated with ΔgD-2 or ΔgD-2::HAPR8 elicited significant ADCK activity in the presence of J774.1 macrophages and ΔgD-2 infected cells compared with serum from mice given VD60 cell lysate (p<0.01). There was no difference between the ADCK activity elicited by sera from mice vaccinated with ΔgD-2 and ΔgD-2::HAPR8. In FIGS. 25D to 25F, at 21 days post-boost, mice were challenged by skin scarification with a 10× LD90 of HSV-2 4674. Mice that received VD60 cell lysate succumbed to HSV-2 by 10 and developed significant epithelial and neurological disease. Mice that received ΔgD-2 and ΔgD-2::HAPR8 were fully protected from morbidity and mortality following challenge. n=5 mice/group from a representative experiment. Statistics for RFADCK assay done using 3-way ANOVA tests. Statistics for survival done using Mantel-Cox log-rank tests. p<0.01; **p<0.0001.

DETAILED DESCRIPTION

Figure 1A:
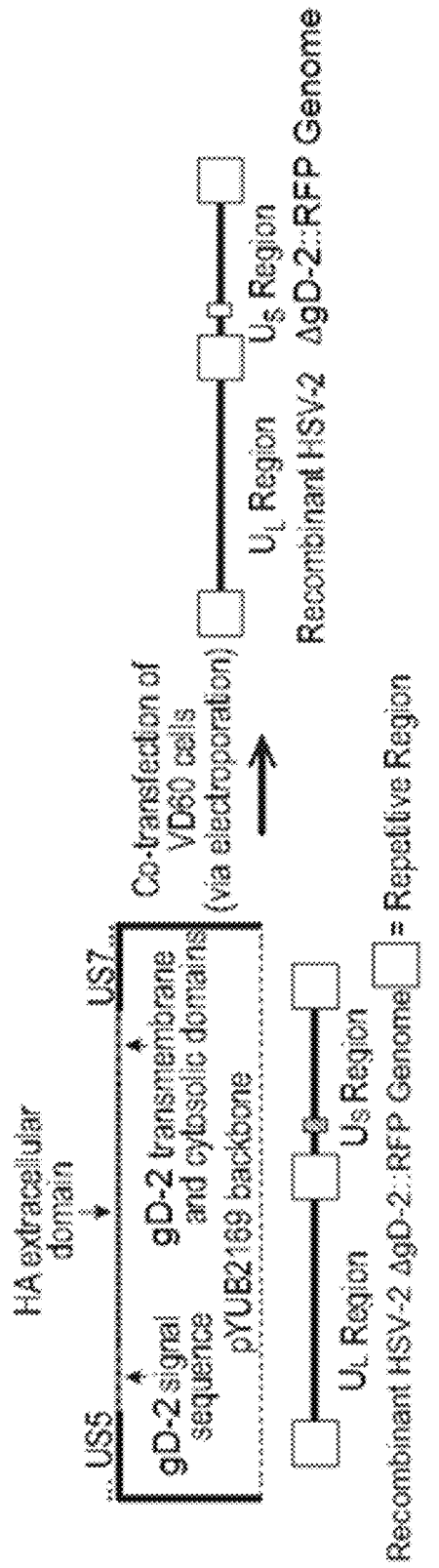
FIGS. 1A-1B. HSV-2 ΔgD::HA and HSV-2 ΔgD::HAstalk were created by co-transfection of plasmid DNA and ΔgD-2::PEF1α-RFP (B3×2.8, also referred to as ΔgD-2.

A process is provided for producing a vaccine vector directed against a heterologous antigen, the process comprising:
a) providing an HSV-2 genome comprising:
   (i) a fully or partially deleted in a gene encoding HSV-2 glycoprotein D, and
   (ii) a nucleic acid comprising a promoter-FP construct, wherein FP is a nucleic acid encoding a fluorescent protein;
b) co-transfecting a host cell with (i) the HSV-2 genome of a) and (ii) a linear DNA fragment encoding the heterologous antigen under conditions whereby allelic recombination occurs between the HSV-2 genome and the DNA fragment;
c) screening plaques resulting from b) to identify plaques not showing fluorescence under excitation light which elicits fluorescent protein fluorescence;
d) recovering from those plaques not showing fluorescence in c) recombinant HSV-2 viruses or virions so as to obtain a vaccine vector directed against the heterologous antigen.

In embodiments, the promoter of the promoter-FP construct is a heterologous promoter.

A process is also provided for producing a vaccine vector directed against an antigen, the process comprising:
a) providing an HSV-2 genome comprising:
   (i) a deletion in a gene encoding HSV-2 glycoprotein D, and
   (ii) a nucleic acid comprising an $P_{EF1\alpha}$-RFP construct, where $P_{EF1\alpha}$ is a promoter of Elongation Factor 1α gene and RFP is a nucleic acid encoding red fluorescent protein, wherein $P_{EF1\alpha}$ and RFP are fused together ($P_{EF1\alpha}$-RFP);
b) co-transfecting a host cell with (i) the HSV-2 genome of a) and (ii) linear DNA fragments encoding, in order, (i) HSV-2 gD signal sequence, the antigen, HSV-2 gD transmembrane domain, HSV-2 gD cytosolic domain, but not encoding a HSV-2 gD extracellular domain, or (ii) HSV-2 gD signal sequence, the antigen, and transmembrane cytoplasmic tail of HSV-2 gD, under conditions permitting allelic recombination;
c) screening plaques resulting from b) to identify plaques not showing red fluorescence under excitation light which elicits red fluorescent protein fluorescence;
d) recovering from those plaques not showing red fluorescence in c) recombinant HSV-2 viruses or virions so as to obtain a vaccine vector directed against the antigen.

A variety of promoters can be employed. Heterologous promoters are preferred including those with high efficiency. Such promoters include the CMV promoter, including the cytomegalovirus major immediate-early promoter. The human elongation factor-1 alpha (EF-1 alpha) constitutive promoter is of human origin and can be used to drive ectopic gene expression in vitro and in vivo. A variety of PEF-1 alpha may be used. The human EF1α gene sequence is known in the art, for example see NCBI accession No. J04617. Other heterologous promoters known in the art and usable in the invention include, but are not limited to, CMV enhancer fused to the chicken beta-actin promoter (CAG), mouse cytomegalovirus (mouse CMV), Chinese hamster elongation factor-1α (CHEF-1α), and phosphoglycerate kinase (PGK).

In embodiments of the processes, the host cell is a complementing cell, for example a cell that phenotypically complements for HSV-1 glycoprotein D. In embodiments of the processes, the host cell is a VD60 cell, which phenotypically complements HSV-1 gD. In embodiments, the vaccine vector produced is genotypically deleted for HSV-2 gD and is phenotypically complemented for HSV-1 gD on a lipid bilayer thereof. In embodiments, the vaccine vector produced does not genotypically encode any HSV gD.

In embodiments, the host cell is co-transfected with (i) the HSV-2 genome of a) and (ii) a linear DNA fragment encoding, in order, (i) HSV-2 gD signal sequence, the heterologous antigen, HSV-2 gD transmembrane domain, HSV-2 gD cytosolic domain, but not encoding a HSV-2 gD extracellular domain, or (ii) HSV-2 gD signal sequence, the heterologous antigen, and transmembrane cytoplasmic tail of HSV-2 gD.

In embodiments, the host cell is co-transfected with (i) the HSV-2 genome of a) and (ii) linear DNA fragments encoding, in order, (i) a promoter, the heterologous antigen, and optionally a poly-A signal.

In embodiments, the co-transfecting is effected by electroporation.

Examples of nucleic acid-encodable fluorescent proteins for use in the invention include red, far red, yellow, green, orange, cyan or photo switchable fluorescent protein. Examples of such proteins are well known in the art. Supplies include Molecular Probes (ThermoFisher USA) and Takara (USA). In an embodiment, the fluorescent protein is Red Fluorescent Protein. Fluorescent proteins with an excitation range of 554-584 nanometers (nm) and an emission range of 562-610 nm are preferred. Examples include Red Fluorescent Protein, mCherry, mTomato, J-Red and mOrange. RFP has an excitation of 556 nm and emission of 584 nm. Alternatively, firefly luciferase or nano-luciferase can be used.

In embodiments, the antigen is not an HSV-2 antigen, i.e. it is a heterologous antigen. As used herein, an antigen is heterologous when it is heterologous relative to HSV-2, i.e. is not naturally found on or in a wildtype HSV-2.

The heterologous antigen can be derived from a living organism, comprising for example, a virus, a bacteria, a parasite, a human cell, an animal cell, or a combination thereof. The heterologous antigen can be a surface protein or a non-surface protein.

The virus can be a pathogenic virus, examples of which include cytomegalovirus (CMV), coxsackie virus, Crimean-Congo hemorrhagic fever virus, chikungunya virus, dengue virus, Dhori virus, Eastern equine encephalitis (EEE) virus, ebola virus, Epstein Barr virus (EBV), hepatitis virus, herpesvirus, human immunodeficiency (HIV) virus, human papilloma virus, human SARS corona virus, human T lymphotropic virus (HTLV), influenza virus, measles virus, mumps virus, Norwalk virus, rabies virus, rotavirus, rubella virus, severe fever with thrombocytopenia syndrome (SFTS) virus, respiratory syncytial virus (RSV), varicella zoster virus, Western equine encephalitis virus, West Nile virus, yellow fever virus, Zika virus, or a combination thereof.

The bacteria can be a pathogenic bacteria, examples of which include *Bacillus* sp., *Baronella* sp., *Bordatella* sp., *Borelli* asp., *Brucella* sp., *Campylobacter* sp., *Chlamydia* sp., *Clostridium* sp., *Corynebacterium* sp., *Enterococcus* sp., *Escherichia* sp., *Haemophilus* sp., *Helicobacter* sp., *Legionella* sp., *Leptospira* sp., *Listeria* sp., *Mycobacterium* sp., *Mycoplasma* sp., *Neisseria* sp., *Rickettsia* sp., *Pseudomonas* sp., *Salmonella* sp., *Shigella* sp., *Staphylococcus* sp., *Streptococcus* sp., *Treponema* sp., *Vibrio* sp., *Yersinia* sp., or a combination thereof.

The parasite can be a pathogenic parasite, examples of which include *Acanthamoeba* spp., *Balamuthia* spp., *Babesia* sp., *Balantidium coli, Blastocystic* sp., *Cryptospiridium* sp., *Cyclospora cayetanensis, Entamoeba histolytica, Giardia lamblia, Isospora bello, Leishmania* sp., *Naegleria foweri, Plasmodium* sp., *Rhinosporidium seeberi, Sarcocystis* sp., *Toxoplasma gondii, Trichomonas* sp., *Trypanosoma* sp., or a combination thereof.

The human cell or animal cell can be, for example, a cancer cell.

In embodiments, the heterologous antigen is an influenza antigen. In embodiments, the heterologous antigen is an influenza hemagglutinin (HA) antigen. In embodiments, the HA antigen is a full-length HA extracellular domain or is a HA stalk domain.

In embodiments, the heterologous antigen is an HIV antigen. In embodiments, the HIV antigen is an Env gp145.

In embodiments, the heterologous antigen is under control of an upstream CMV promoter and has a downstream SV40 poly-A signal. The SV40 poly-A signal is known in the art. It promotes polyadenylation and transcription termination.

In embodiments, the promoter is a promoter of Elongation Factor 1☐ gene (PEF1α) and wherein PEF1α and FP are fused together (PEF1α-FP).

In embodiments, the nucleic acid is codon-optimized for expression. See, for example, Table 4 in the examples hereinbelow.

Also provided is a vaccine vector made by the process described herein.

Also provided is a recombinant herpes simplex virus-2 (HSV-2) having a genome encoding a heterologous antigen made by the process described herein.

Also provided is a recombinant herpes simplex virus-2 (HSV-2) having (i) a complete deletion of an HSV-2 glycoprotein D-encoding gene in the genome thereof and (ii) (a) encoding: a promoter, a heterologous antigen signal sequence, and a heterologous antigen or (b) encoding: a promoter and a heterologous antigen.

Also provided is a recombinant herpes simplex virus-2 (HSV-2) having (i) a partial deletion of an HSV-2 glycoprotein D-encoding gene in the genome thereof and (ii) (a) encoding, in order, an HSV-2 gD signal sequence, a heterologous antigen, an HSV-2 gD transmembrane domain, optionally an HSV-2 gD cytosolic domain, but not encoding an HSV-2 gD extracellular domain, or (b) encoding, in order, an HSV-2 gD signal sequence, a heterologous antigen, cytosolic domain of HSV-2 gD.

Also provided is a recombinant herpes simplex virus-2 (HSV-2) having (i) a partial deletion of an HSV-2 glycoprotein D-encoding gene in the genome thereof and (ii) (a) encoding, in order, an HSV-2 gD signal sequence, a heterologous antigen, an HSV-2 gD transmembrane domain, an HSV-2 gD cytosolic domain, but not encoding an HSV-2 gD extracellular domain, or (b) encoding, in order, an HSV-2 gD signal sequence, a heterologous antigen, and transmembrane cytoplasmic tail of HSV-2 gD.

In embodiments, the recombinant HSV-2 further comprises a parasitic surface glycoprotein on a lipid bilayer thereof, wherein the parasite is a parasite of a mammal.

In an embodiment, the HSV-2 glycoprotein D-encoding gene is an HSV-2 US6 gene. (For example, see Dolan et al. J Virol. 1998 March; 72(3): 2010-2021. (PMCID: PMC109494) "The Genome Sequence of Herpes Simplex Virus Type 2" for HSV-2 genome and US6 gene, hereby incorporated by reference in its entirety). In embodiments, the HSV-2 glycoprotein D-encoding gene is equivalent of an HSV-2 US6 gene. Such equivalents are easily identifiable by those of skill in the art using readily available sequencing and alignment tools.

In embodiments, the heterologous antigen is an influenza antigen. In embodiments, the heterologous antigen is an influenza hemagglutinin (HA) antigen.

In embodiments, the HA antigen is a full-length HA extracellular domain or is a HA stalk. In embodiments, the full-length HA includes a HA signal sequence. In embodiments, the HA is an HA of a human influenza A or human influenza B. Examples of the hemagglutinin gene ("HA") include GenBank V01098.1; NCBI Reference Sequence: NP_040980.1. HA gene sequences, and the mature hemagglutinin peptide sequences, are well known in the art, and multiple HA sequences are available to those skilled in the art at the NCBI database. In addition, one skilled in the art can readily identify the commonly discussed stalk, extracellular domain and other regions of hemagglutinin. In addition, seasonal influenza virus strain sequences, including the HA sequence, are routinely sequenced and identified in the art.

Other influenza genes, as heterologous antigens, that can be added to ΔgD-2 by allelic exchange with B3×2.8 (ΔgD-2::PEF1α-RFP) include neuraminidase (NA), matrix protein 1 (M1), influenza A virus (IAV) matrix protein 2 (M2), influenza B virus (IBV) matrix protein 2 (M2), nucleoprotein (NP), and influenza B virus NB. A combination comprising at least one of the foregoing can also be used. The corresponding modified headless HA gene for each strain can be added as well as a version of each headless antigen where a trimerization domain has been added to increase stability. Table 1 provides non-limiting influenza examples of other such antigen genes. Other examples include inserting the HA gene from A/Vietnam/1203/04, the HA, headless HA, NA, M1, M2, NP, and NB genes from, e.g., B/Yamagata/16/1988 and B/Victoria/2/1987 strains.

Figure 1B:
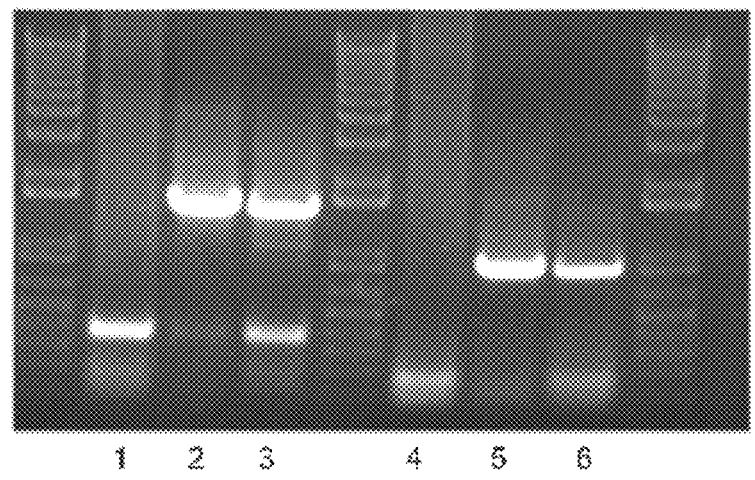

One method for generating the recombinant HSV-2 gD −/− viral vector expressing HIV or Influenza A virus antigens is as follows:

1. Generating an engineered HSV-2 genome by partially deleting the glycoprotein D encoding gene Us6 such that only glycoprotein D signal sequence and the transmembrane-cytoplasmic domain sequence is left (no extracellular domain sequence present). The deleted portion of the glycoprotein D gene is replaced with a $P_{EF1\alpha}$-RFP gene wherein red fluorescent protein (RFP) is expressed under the control of a $P_{EF}1\alpha$ promoter.
2. A cosmid pYUB2169 can be engineered to express a gene for a heterologous antigen (e.g., HIV envelope protein antigen Env gp145 or Influenza virus HA stalk antigen) of choice that is flanked by sequences of the HSV-2 signal sequence and the transmembrane-cytoplasmic domain sequence on either respective side.
3. Both HSV-2 gD−/− RFP+ genome of (1) and engineered cosmid pYUB2169 of (2) can be introduced into a VD60 cell line.
4. Within the VD60 cell line, homologous recombination occurs between the HSV-2 partially deleted glycoprotein D gene (RFP gene inserted) of (1) and the pYUB2169-HIV Env gp145 or Influenza A virus HA stalk antigen expressing gene of (2). A successful recombination is expected to lead to loss of RFP gene and generation of a HSV-2 gD−/− virus expressing a heterologous HIV or Influenza virus antigen (see FIG. 1A-1B).
5. VD60 cell culture plaques that are negative for RFP expression contain HSV-2 gD−/− the virus particles are expected to express HIV Env gp145 or I influenza virus HA stalk antigen.
6. The HSV-2 gD−/− virus expressing a heterologous HIV Env gp145 or Influenza A virus HA stalk antigen thus generated can be used to vaccinate a person and elicit at strong antibody mediated response and protective immunity against HIV or Influenza Virus.

In embodiments, the heterologous antigen is an HIV antigen. In embodiments, the HIV antigen is an HIV-1 or HIV-2 antigen. For example, the heterologous antigen is an HIV-1 antigen. In embodiments, the HIV is a C-subtype. In embodiments, the HIV antigen is an Env, Pol, Gag, or Nef. In an embodiment, the HIV antigen is an Env antigen. In embodiments, the HIV antigen is a C-subtype Env antigen. In embodiments, the antigen is an Env gp145. In embodiments, the heterologous antigen is a fully intact membrane-proximal external region (MPER). In embodiments, the heterologous antigen is extended by a polylysine tail. In embodiments, the heterologous antigen is not extended by a

TABLE 1

GENBANK SEQUENCE ACCESSION CODES FOR EXAMPLES OF EXEMPLARY INFLUENZA ANTIGENS

| Antigens | A/Puerto Rico/ 1934/8 H1N1 | A/California/ 04/2009 Pandemic H1N1 swine flu | A/Hong Kong/ 156/97 Avian H5N1 | A/New York/ 35/2017 Seasonal H3N2 | A/Hong Kong/ 213/2003 Avian H5N1 | A/Shanghai/ 01/2014 Avian H7N9 | A/swine/ Missouri/ 2124514/ 2006 Swine H2N3 | A/Italy/ 3/2013 Avian H7N7 | A/Netherlands/ 602/2009 H1N1 | A/Hong Kong/ 33982/2009 H9N2 |
|---|---|---|---|---|---|---|---|---|---|---|
| HA | | KX136139 | AF028709 | CY256029 | AB212054 | KJ411975 | EU258939 | KF918337 | CY148123 | KF188316 |
| NA | CY121111 | KX136323 | AF036357 | CY256031 | AB212056 | KJ411977 | EU258937 | KF918339 | CY039528 | KF188318 |
| M1 | KC866600 | KX135622 | AF036358 | CY256032 | AB212057 | KJ411976 | EU258938 | KF918340 | CY046944 | KF188319 |
| M2 | KC866600 | KX135622 | AF036358 | CY256032 | | KJ411976 | EU258938 | KF918340 | CY046944 | KF188319 |
| NP | CY148246.1 | KX136793 | AJ291400 | CY256030 | AB212055 | KJ411978 | EU258936 | KF918338 | CY046943 | KF188317 | polylysine tail. HIV gp145 Env protein sequences are readily identifiable by alignment tools, and are routine to sequence. In embodiments, the ectodomain of HIV Env gp145 is fused with the signal peptide and transmembrane cytoplasmic tail of HSV gD.

Also provided is a cell comprising therein a recombinant virus as described herein, wherein the cell is not present in a human being.

Also provided is a vaccine composition comprising a recombinant virus as described herein. In embodiments, the vaccine comprises an adjuvant which is not derived from the HSV-2. Adjuvants are well known in the art and include alum, oil-in-water or water-in-oil emulsions, aluminum salts such as aluminum hydroxide, aluminum phosphate, and aluminum potassium sulfate, and monophosphoryl lipid A. In embodiments, the vaccine does not comprise an adjuvant.

Also provided is a pharmaceutical composition comprising a recombinant HSV-2 virus as described herein, and a pharmaceutically acceptable carrier. Pharmaceutically acceptable carriers are well-known in the art.

Also provided is a method of eliciting and/or enhancing an immune response in a subject, the method comprising administering to the subject an amount of (i) a recombinant virus as described herein; (ii) a vaccine as described herein; or (iii) a pharmaceutical composition as described herein, in an amount effective to elicit and/or enhance immune response in a subject.

Also provided is a method of eliciting and/or enhancing an immune response in a subject against a pathogen expressing a heterologous antigen, the method comprising administering to the subject an amount of (i) a recombinant virus as described herein; (ii) a vaccine as described herein; or (iii) a pharmaceutical composition as described herein, in an amount effective to elicit and/or enhance immune response in a subject, wherein the recombinant virus of (i), (ii) or (iii) expresses the heterologous antigen.

Also provided is a method of treating or reducing the likelihood of an influenza infection in a subject, the method comprising administering to the subject an amount of (i) a recombinant virus as described herein; (ii) a vaccine as described herein; or (iii) a pharmaceutical composition as described herein, in an amount effective to treat or reduce the likelihood of an influenza infection in a subject. For treating or reducing likelihood of influenza, the heterologous antigen is an influenza HA antigen. Also provided is a method of vaccinating a subject for influenza infection comprising administering to the subject an amount of (i) a recombinant virus as described herein; (ii) a vaccine as described herein; or (iii) a pharmaceutical composition as described herein, in an amount effective to vaccinate a subject for influenza infection.

Also provided is a method of treating or reducing the likelihood of an HIV infection in a subject, the method comprising administering to the subject an amount of (i) a recombinant virus as described herein; (ii) a vaccine as described herein; or (iii) a pharmaceutical composition as described herein, in an amount effective to treat or reduce the likelihood of an HIV infection in a subject. For treating HIV or reducing likelihood of HIV, the heterologous antigen is an HIV antigen. Also provided is a method of vaccinating a subject for HIV infection comprising administering to the subject an amount of (i) a recombinant virus as described herein; (ii) a vaccine as described herein; or (iii) a pharmaceutical composition as described herein, in an amount effective to vaccinate a subject for HIV infection.

Also provided is a method of eliciting and/or enhancing an immune response in a subject, the method comprising administering to the subject an amount of a recombinant herpes simplex virus-2 (HSV-2) made by a process described herein and comprising (i) a complete deletion of an HSV-2 glycoprotein D-encoding gene in the genome thereof and (ii) encoding a promoter, a influenza hemagglutinin (HA) antigen signal sequence, and an HA antigen in an amount effective to elicit and/or enhance an immune response in a subject.

Also provided is a method of treating or reducing the likelihood of an influenza infection in a subject, the method comprising administering to the subject an amount of a recombinant herpes simplex virus-2 (HSV-2) made by a process described herein and comprising (i) a complete deletion of an HSV-2 glycoprotein D-encoding gene in the genome thereof and (ii) encoding a promoter, a influenza hemagglutinin (HA) antigen signal sequence, and an HA antigen in an amount effective to treat or reduce the likelihood of an influenza infection in a subject.

Also provided is a method of vaccinating a subject for influenza infection, the method comprising administering to the subject an amount of a recombinant herpes simplex virus-2 made by a process described herein and comprising (i) a complete deletion of an HSV-2 glycoprotein D-encoding gene in the genome thereof and (ii) encoding a promoter, a influenza hemagglutinin (HA) antigen signal sequence, and an HA antigen in an amount effective to vaccinate a subject for influenza infection.

In embodiments, the HA antigen is a full-length HA extracellular domain.

In embodiments, the methods further comprise, subsequent to an initial administration of the recombinant herpes simplex virus-2 encoding a full-length HA extracellular domain, administering one or more amounts of a recombinant herpes simplex virus-2 having (i) a complete deletion of an HSV-2 glycoprotein D-encoding gene in the genome thereof and (ii) encoding a promoter, a HA antigen signal sequence, and an HA stalk, but not encoding a full-length HA.

In an embodiment of the methods or processes, the HSV-2 glycoprotein D comprises the amino acid sequence set forth in SEQ ID NO:1:

```
MGRLTSGVGTAALLVVAVGLRVVCAKYALADPSLKMADPNRFRGKNLPVL

DQLTDPPGVKRVYHIQPSLEDPFQPPSIPITVYYAVLERACRSVLLHAPS

EAPQIVRGASDEARKHTYNLTIAWYRMGDNCAIPITVMEYTECPYNKSLG

VCPIRTQPRWSYYDSFSAVSEDNLGFLMHAPAFETAGTYLRLVKINDWTE

ITQFILEHRARASCKYALPLRIPPAACLTSKAYQQGVTVDSIGMLPRFIP

ENQRTVALYSLKIAGWHGPKPPYTSTLLPPELSDTTNATQPELVPEDPED

SALLEDPAGTVSSQIPPNWHIPSIQDVAPHHAPAAPSNPGLIIGALAGST

LAVLVIGGIAFWVRRRAQMAPKRLRLPHIRDDDAPPSHQPLFY
(HSV-2 reference strain HG52)
```

In an embodiment, the HSV-2 in which the HSV-2 glycoprotein D-encoding gene is deleted is an HSV-2 having a genome (prior to the deletion) as set forth in one of the following Genbank listed sequences: HSV-2(G) (KU310668), HSV-2(4674) (KU310667), B3×1.1 (KU310657), B3×1.2 (KU310658), B3×1.3 (KU310659), B3×1.4 (KU310660), B3×1.5 (KU310661), B3×2.1 (KU310662), B3×2.2 (KU310663), B3×2.3 (KU310664), B3×2.4 (KU310665), B3×2.5 (KU310666). These sequences are hereby incorporated by reference.

A cell is provided comprising therein a recombinant HSV-2 genome as described herein.

Also provided is a vaccine composition comprising the recombinant HSV-2 virus as described herein. In an embodiment, the vaccine comprises an immunological adjuvant. In an embodiment, the vaccine does not comprise an immunological adjuvant. In an embodiment of the vaccine, compositions or pharmaceutical compositions described herein comprising a recombinant HSV-2, the HSV-2 is live-attenuated.

Also provided is a composition comprising the recombinant HSV-2 virus as described herein, wherein the genome of the virus or virion comprises at least a deletion of a second gene, wherein the second gene is necessary for HSV-2 viral replication or virulence.

A pharmaceutical composition comprising the recombinant HSV-2 virus as described herein, and a pharmaceutically acceptable carrier.

In an embodiment, the composition or pharmaceutical composition or vaccine is formulated so that it is suitable for subcutaneous administration to a human subject. In an embodiment, the composition or pharmaceutical composition or vaccine is formulated so that it is suitable for oral administration to a human subject. In an embodiment, the composition or pharmaceutical composition or vaccine is formulated so that it is suitable for intravaginal administration to a human subject. In an embodiment, the composition or pharmaceutical composition or vaccine is formulated so that it is suitable for intra-muscular, intra-nasal, or mucosal administration to a human subject. In embodiments of the methods herein, and embodiments of the composition or pharmaceutical composition or vaccine formulations herein, administration can be auricular, buccal, conjunctival, cutaneous, subcutaneous, endocervical, endosinusial, endotracheal, enteral, epidural, via hemodialysis, interstitial, intrabdominal, intraamniotic, intra-arterial, intra-articular, intrabiliary, intrabronchial, intrabursal, intracardiac, intracartilaginous, intracaudal, intracavernous, intracavitary, intracerebral, intracisternal, intracorneal, intracoronary, intradermal, intradiscal, intraductal, intraepidermal, intraesophagus, intragastric, intravaginal, intragingival, intraileal, intraluminal, intralesional, intralymphatic, intramedullary, intrameningeal, intramuscular, intraocular, intraovarian, intraepicardial, intraperitoneal, intrapleural, intraprostatic, intrapulmonary, intrasinal, intraspinal, intrasynovial, intratendinous, intratesticular, intrathecal, intrathoracic, intratubular, intratumor, intratympanic, intrauterine, intravascular, intravenous, intraventricular, intravesical, intravitreal, laryngeal, nasal, nasogastric, ophthalmic, oral, oropharyngeal, parenteral, percutaneous, periarticular, peridural, rectal, inhalationally, retrobulbar, subarachnoid, subconjuctival, sublingual, submucosal, topically, transdermal, transmucosal, transplacental, transtracheal, ureteral, urethral, or vaginal. A combination comprising at least one of the foregoing routes of administration can also be used.

Also provided is a method of eliciting an immune response in a subject, the method comprising administering to the subject an amount of (i) the recombinant HSV-2 virus as described herein in an amount effective to elicit an immune response in a subject.

In an embodiment, the HSV-2 glycoprotein D-encoding gene is an HSV-2 US6 gene. In an embodiment, the HSV-2 recombinant virus encodes a heterologous surface glycoprotein. In an embodiment the heterologous surface glycoprotein is an HSV-1 gD. In an embodiment, the HSV-2 recombinant virus comprises a non-genotypically encoded HSV-1 gD also encodes a heterologous surface glycoprotein that is not a herpesvirus glycoprotein and/or is and not involved in herpesviridae infection, and which is encoded by a transgene that has been inserted into the genome of the recombinant HSV-2. In an embodiment, the genome of the recombinant HSV-2 does not encode any herpes virus gD. In an embodiment, the surface glycoprotein is present on a lipid bilayer of the virus by way of infecting a cell with a recombinant HSV-2 having a deletion of an HSV-2 glycoprotein D-encoding gene, wherein the cell is or has been transfected to express the surface glycoprotein on a cell membrane thereof, and wherein the recombinant HSV-2 comprising the surface glycoprotein present on a lipid bilayer is produced from the cell. In an embodiment the host cell is a HSV-1 gD complementing cell. In an embodiment, the host cell encodes an HSV-1 gD under the endogenous gene promoter. In an embodiment the host cell is a HSV-1 gD complementing VD60 cell. (See, e.g., Ligas et al., J Virol. 1988 May; 62(5):1486-94, hereby incorporated by reference).

Also provided is a cell comprising therein a recombinant virus as described herein, wherein the cell is not present in a human being.

A vaccine composition comprising a recombinant virus as described herein. In an embodiment of the vaccine composition, the vaccine composition comprises an immunological adjuvant.

Also provided is a composition comprising a recombinant virus as described herein, wherein the genome of the virus comprises at least a deletion of a second gene, wherein the second gene is necessary for HSV-2 viral replication.

In an embodiment, the recombinant virus as described herein does not comprise a deletion of a second gene.

Reducing the likelihood of a viral infection is understood to mean amelioration of the extent of development of the relevant disease or chances of infection in a subject treated with the virus, vaccine or compositions described herein, as compared to an untreated subject.

In an embodiment of the methods herein for immunizing, vaccinating or eliciting an immune response, passive transfer of the virus or the antibodies or immune factors induced thereby may be effected from one subject to another. The relevant product may be treated after obtention from one subject before administration to a second subject. In a preferred embodiment of the inventions described herein, the subject is a mammalian subject. In an embodiment, the mammalian subject is a human subject.

In an embodiment, vaccinating a subject with an antigen elicits a humoral immune response to that antigen in the subject. A vaccinated individual is usually able to mount a more efficacious immune response to a subsequent challenge from a pathogen comprising that antigen than they would be able to prior to vaccination.

In an embodiment of the methods described herein, the subject has not yet been infected with influenza virus. In an embodiment of the methods described herein, the subject has not yet been infected with HIV. In an embodiment of the methods described herein, the subject has been infected with influenza virus. In an embodiment of the methods described herein, the subject has been infected with HIV.

In embodiments, the influenza infection is a human influenza A infection. In embodiments, the influenza infection is a human influenza B infection. In embodiments, the HIV infection is an HIV-1 infection. In embodiments, the HIV infection is an HIV-2 infection.

"Codon optimization" is defined as modifying a nucleic acid sequence for enhanced expression in the cells of interest, e.g. human, by replacing at least one, more than one, or a significant number, of codons of the native sequence with codons that are more frequently or most frequently used in the genes of that vertebrate. Various species exhibit particular bias for certain codons of a particular amino acid. In one aspect, the present invention relates to codon optimized inserts, nucleic acids or vectors, or host cells comprising such.

Also provided is a method of quantitating a rate or amount of antibody-dependent cell-mediated killing (ADCK) in a population of cells comprising infecting a plurality of cells of the population of cell with a fluorescent protein-expressing recombinant HSV-2 that comprises a genome deleted for the gene encoding HSV-2 gD, under conditions permitting expression of the fluorescent protein in the cells, contacting the plurality of infected cells with an antibody-containing solution and a population of immune cells, and quantitating at one or more time points the amount of cells exhibiting fluorescent protein fluorescence and, optionally, one or more markers, so as to quantitate over time the amount of live infected cells, so as to thereby quantitating the rate or amount of ADCK in the population of immune cells.

Also provided is a method of quantitating a rate or amount of antibody-dependent cell-mediated killing (ADCK) in a population of cells comprising infecting a plurality of cells of the population of cells with a fluorescent protein-expression expressing recombinant HSV-2 that comprises a genome deleted for the gene encoding HSV-2 gD, under conditions permitting expression of the fluorescent protein in the cells, contacting the plurality of infected cells with an antibody-containing solution, and quantitating at one or more time points the amount of cells exhibiting fluorescent protein fluorescence and, optionally, one or more markers, so as to quantitate over time the amount of live infected cells, so as to thereby quantitating the rate or amount of ADCK in the population of cells.

In embodiments, the recombinant HSV-2 is made by a process as described herein.

In embodiments, the method is performed in vitro. In embodiments, the population of immune cells comprises a population of macrophages. In embodiments, the macrophages are human. In embodiments, the antibody-containing solution comprises serum. In embodiments, the fluorescent protein is as described hereinabove. In an embodiment, the fluorescent protein is Red Fluorescent Protein. In an embodiment, only the cells quantitated as RFPhigh are considered live. In an embodiment, the plurality of cells are RFPhigh if they express RFP above the mean intensity of an RFp-expressing cell of the infected population of cells. In embodiments, the method is performed with the population of immune cells present at effector:target ratio of 5:1 or greater. In embodiments, the method is performed with the population of immune cells present at effector:target ratio of 10:1 or greater.

In embodiments, the amount of cells exhibiting fluorescent protein fluorescence and, optionally, one or more markers, is measured by fluorescence-activated cell sorting (FACS). In embodiments, the amount of cells exhibiting fluorescent protein fluorescence and, optionally, one or more markers, is measured by fluorescence spectrometer, fluorescence microplate reader, and fluorescence microscopy or fluorescence plate reader. In embodiments, the one or more markers comprise a cell membrane marker and/or a live/dead marker.

In embodiments, the method further comprises quantitating at one or more time points the amount of cells exhibiting fluorescent protein fluorescence and, optionally, one or more markers, in a control population of infected cells otherwise identical, but not contacted with an antibody-containing solution and comparing the amount or rate quantitated to that quantitated for the population of cells contacted with the antibody-containing solution.

In other embodiments of the invention relating to assays for ADCK, instead of a fluorescent protein the marker in the recombinant HSV-2 ΔgD-2 can be a beta galactosidase or an alkaline phosphatase. Thus, the methods, processes and compositions disclosed herein can comprise, mutatis mutandis, recombinant HSV-2 ΔgD-2 comprising a nucleic acid in the genome thereof encoding beta galactosidase or an alkaline phosphatase.

"And/or" as used herein, for example, with option A and/or option B, encompasses the separate embodiments of (i) option A, (ii) option B, and (iii) option A plus option B.

All combinations of the various elements described herein are within the scope of the invention unless otherwise indicated herein or otherwise clearly contradicted by context.

This invention may be better understood from the Examples, which follow.

EXAMPLES

Example 1

An engineered HSV-2 virus that replaces the gD gene (ΔgD-2) with a gene that strongly expresses the red fluorescent protein (RFP) was constructed. Once achieved, this provided an improved screen for identifying and obtaining new recombinants. The ΔgD-2::RFP recombinant was made from a ΔgD-2 that showed protection. The red fluorescent ΔgD-2:RFP, referred to herein also as B3×2.8 or ΔgD-2::PEF1α-RFP, retains the capacity of the original ΔgD-2 to elicit protective immunity against HSV infection but also appears to have unaltered in vitro replication kinetics. Moreover, ΔgD-2::RFP possesses significant advantages over HSV-2 ΔgD::GFP virus for making recombinants. Since the RFP gene is fused to a highly efficient promoter, for example promoter of the EF1α (Elongation Factor 1 α) gene, its expression is easily detected using a fluorescent microscope. In addition, visualization of red fluorescence in cells infected with ΔgD-2::RFP does not have the background found with the green fluorescent ΔgD-2. This property enables unambiguous identification of recombinant viruses in which the ΔgD-2::PEF1α-RFP allele is replaced by other allelic exchange substrates.

Construction of the HSV-2 ΔgD-−/+gD-1 virus (hereafter called "ΔgD-2") using HSV-2(G) as the backbone was accomplished as detailed below. To make the allelic exchange constructs, an expression construct was generated by Gibson cloning into an *E. coli* plasmid, cloning the expression construct in between the SpeI and BclI sites of a shuttle (for example, cosmid pYUB2169) that contains 12 kb of the HSV-2(G) virus spanning from US1 To US9, electroporated the Pad restriction fragment from the pYUB2169 recombinant alongside ΔgD-2::RFP DNA into VD60 cells, and screening the resulting plaques for loss of red fluorescence. (See FIG. 1).

This system was used to generate two sets of recombinant ΔgD-2 strains containing hemagglutinin (HA) antigens derived from the influenza A virus (IAV) strain A/Puerto Rico/8/1934 (PR8). The first set of recombinants contain chimeric gD::HA genes recombined into the US6 region of ΔgD-2 through the use of, for example, pYUB2169. These recombinant genes were made up of the extracellular domain of PR8 HA fused to the transmembrane, cytosolic, and signal sequence domains of HSV-2 (G) gD. The second set of recombinants contain modified or unmodified PR8 HA genes fused to an upstream CMV promoter and downstream SV40 polyadenylation signal. These cassettes were inserted into the US6 region of ΔgD-2 using a modified pYUB2169 identified as pBRL812. Each set of recombinants contained three type of HA genes:

FL HA nOP—Full-length extracellular domain hemagglutinin, non-codon optimized.

HL HA nOP—Headless extracellular domain hemagglutinin, non-codon optimized.

HL HA OPT—Headless extracellular domain hemagglutinin, codon-optimized.

The following constructs were made:

ΔgD-2::RFP (ΔgD-2::PEF1α-RFP) was constructed by (1) introducing a kanamycin marker in RFP plasmid ptwB, (2) amplifying the kan marker and RFP (dTomato) with oligos having ~50 bp homologous sequence upstream and downstream of US6, (3) recombining in DY331 cells, then adding the PCR product followed by transformation with cosmid pYUB2156. (4) The kan marker was removed by restriction digest and ligation. (5) HSV2(G) genomic DNA and pYUB2167 were co-transfected in VD60 cells to generate ΔgD-2::RFP by allelic exchange.

ΔgD-2 was obtained by co-transfection of cosmid pYUB2163 with the ΔgD-2::RFP genome in VD60 cells to generate the ΔgD-2 genome by allelic exchange. This genome is free of all markers and antibiotic resistance genes. The resultant unmarked virus was sorted based on lack of RFP expression. RFP-negative plaques were purified three times and the lack of the RFP gene was verified by PCR and sequencing.

ΔgD-2::FL HA nOP was constructed by (1) Gibson cloning the cytosolic, transmembrane, and signal sequence domains of HSV-2 (G) gD to the extracellular domain of custom synthesized PR8 HA (Genscript, Piscataway, NJ) in the pYUB2169 plasmid and (2) co-transfecting the resultant plasmid, pBJJ1, with the ΔgD-2:RFP genome in VD60 cells to generate the desired recombinant by allelic exchange.

ΔgD-2::HL HA nOP was constructed similarly to ΔgD-2::FL HA nOP, but using a custom synthesized PR8 HA gene where the HA1 head domain was replaced with 4 glycine residues (Genscript). The plasmid used for transfection was called pBJJ2.

ΔgD-2::HL HA OPT was constructed similarly to ΔgD-2::HL HA nOP, but using a custom synthesized PR8 HA gene where the HA1 head domain was replaced with 4 glycine residues and every codon which had less than 9.5% representation in HSV-2 (G) gD for its cognate amino acid was replaced with the codon most abundant in HSV-2 (G) gD (Genscript). The plasmid used for transfection was called pBJJ4.

ΔgD-2::PCMV-FL HA nOP was constructed by (1) restriction cloning the full length PR8 HA gene (Genscript) in between the xbaI and HindIII restriction sites of pEGFP-N1 (Addgene, Cambridge, MA) (2) restriction cloning the PCMV-FL HA nOP::SV40 polyA cassette from the resultant plasmid into the SpeI and BclII sites of pBRL812. The resulting plasmid, pJHA1, was cut with PacI and AsiSI and co-transfected with the ΔgD-2::RFP genome in VD60 cells to generate the desired recombinant by allelic exchange.

ΔgD-2::PCMV-HL HA nOP was constructed similarly to ΔgD-2::PCMV-FL HA nOP but using a custom synthesized PR8 HA gene where the HA1 head domain was replaced with 4 glycine residues (Genscript). The plasmid used for transfection was called pJHA2.

ΔgD-2::PCMV-HL HA OPT was constructed similarly to ΔgD-2::PCMV-FL HA nOP but using a custom synthesized PR8 HA gene where the HA1 head domain was replaced with 4 glycine residues and every codon which had less than 9.5% representation in HSV-2 (G) gD for its cognate amino acid was replaced with the codon most abundant in HSV-2 (G) gD (Genscript). The plasmid used for transfection was called pJHA4.

TABLE 2

HSV-2 VIRUSES GENERATED

| Stock # | Parent | Genotype | How Constructed | Reference |
|---|---|---|---|---|
| B³x 2.6 | HSV-2 G | Wild-type | N/A | ATCC |
| B³x 2.7 | HSV-2 G | ΔgD-2::GFP | Allelic Exchange w G | Petro, Gonzalez et al. *Elife* Petro et al. *JCI* |
| B³x 2.8 | B³x 2.7 | ΔgD-2::RFP (also referred to as ΔgD-2::$P_{EF1\alpha}$-RFP) | Allelic Exchange w B³x 2.6 | Disclosed herein |
| B³x 2.9 | HSV-2 G | ΔgD-2 | Allelic Exchange w B³x 2.8 (Unmarked ΔgD-2) | Disclosed herein |
| B³x 2.10 | HSV-2 G | ΔgD-2::$HA_{PR8}$ | Allelic Exchange w B³x 2.8 | Disclosed herein |
| B³x 2.11 | HSV-2 G | ΔgD-2:: $HA_{PR8-STALK}$ | Allelic Exchange w B³x 2.8 | Disclosed herein |
| β³χ1 | HSV-2 G | ΔgD-2::FL HA nOP | Allelic Exchange w B³x 2.8 | Disclosed herein |
| β³χ2 | HSV-2 G | ΔgD-2::HL HA nOP | Allelic Exchange w B³x 2.8 | Disclosed herein |
| β³χ3 | HSV-2 G | ΔgD-2::HL HA OPT | Allelic Exchange w B³x 2.8 | Disclosed herein |
| β³χ4 | HSV-2 G | ΔgD-2::$P_{CMV}$-FL HA nOP | Allelic Exchange w B³x 2.8 | Disclosed herein |
| β³χ5 | HSV-2 G | ΔgD-2::$P_{CMV}$-HL HA nOP | Allelic Exchange w B³x 2.8 | Disclosed herein |
| β³χ6 | HSV-2 G | ΔgD-2::$P_{CMV}$-HL HA OPT | Allelic Exchange w B³x 2.8 | Disclosed herein |

Figure 2:
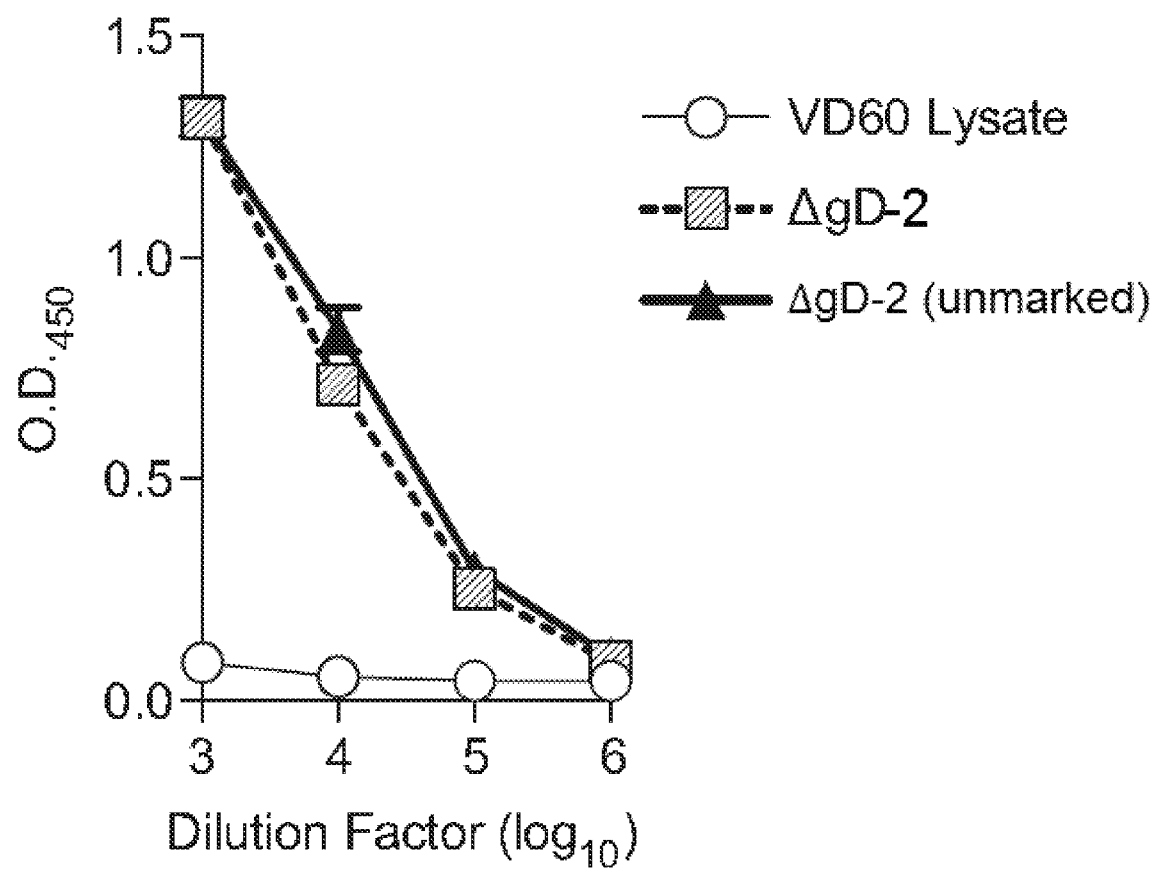

Whole genome sequencing was used to verify the deletion of US6. To test immunogenicity, mice were vaccinated on Day 0 (d0) and d21, then sera was taken on d40. ΔgD-2 elicited anti-HSV antibodies that are similar to those obtained with ΔgD-2::GFP (See FIG. 2).

Figure 3:
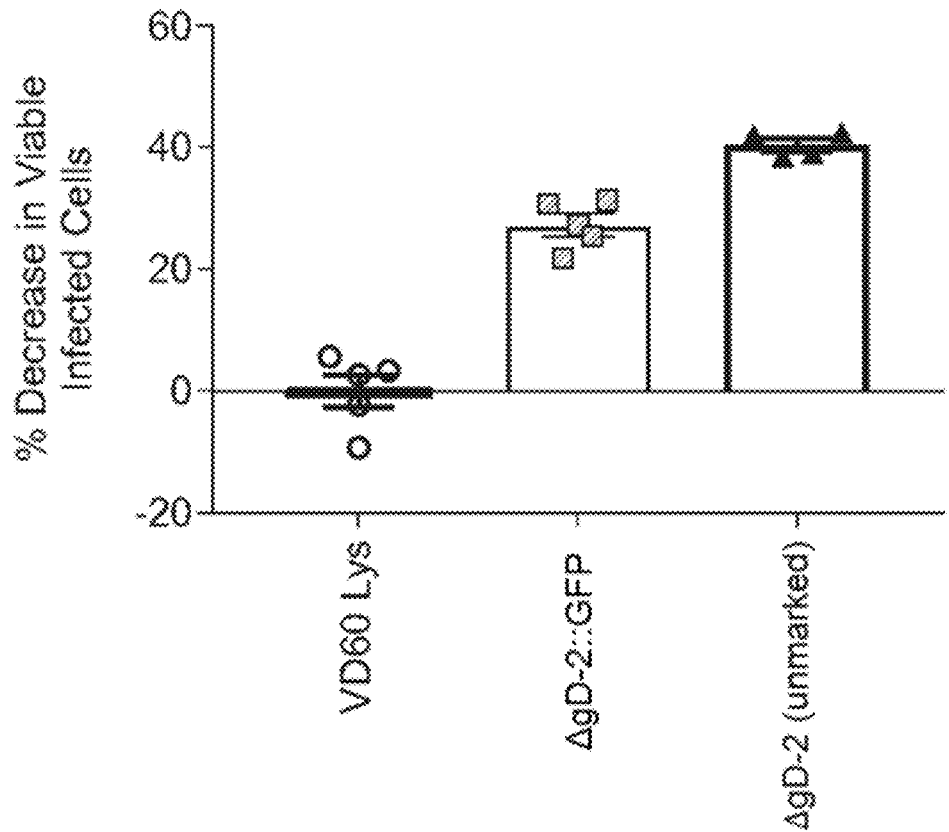
Figure 4:
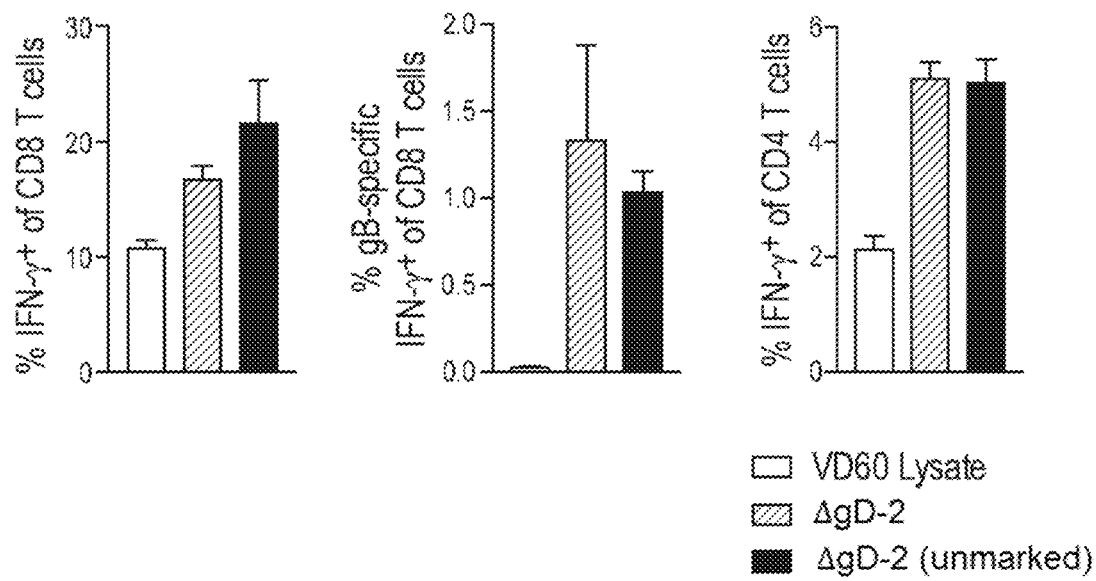

Mechanistically, it seems that the most important correlates of protection are ADCC and ADCP. Sera from ΔgD-2 vaccinated mice induced significantly more ADCC/ADCP immunity than sera from ΔgD-2::GFP vaccinated mice (FIG. 3). The CD8 and CD4 T-cell responses were similar at 40 days using the same vaccination strategy (FIG. 4).

Figure 5:
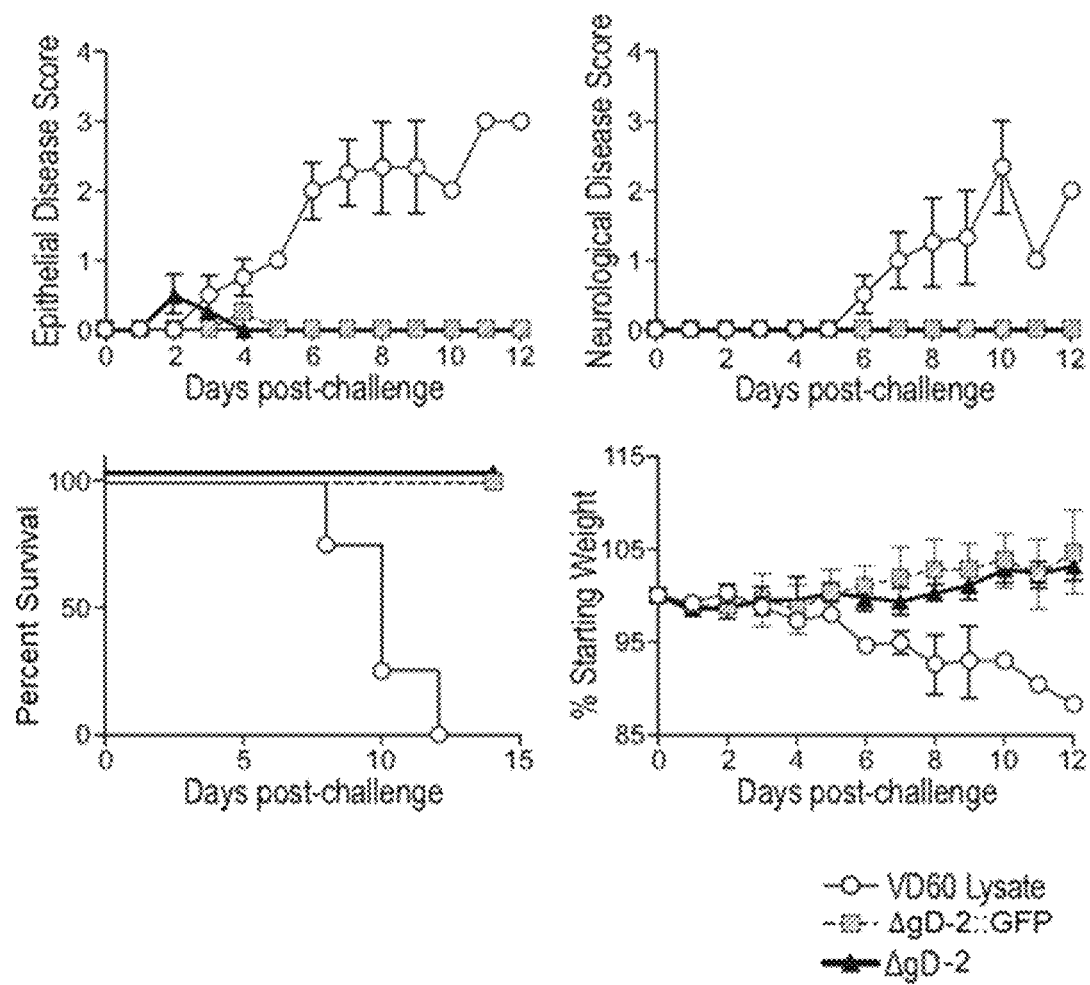

ΔgD-2 vaccination protects mice against challenge with a wild-type HSV-2 4674, which is a clinical isolate obtained from the virology laboratory at Montefiore Hospital, Bronx, NY, as well as the GFP-marked construct. Mice were vaccinated with either the wild-type HSV-2 or the GFP-marked construct virus on d0 and d21. Twenty-one days after boost, mice were challenged subcutaneously with 10× LD90 HSV-2 4674 and followed for skin lesion changes, presence of virus in the dorsal root ganglia, body weight, and survival. The unmarked virus behaved nearly identically by all measures (FIG. 5).

Materials and Methods

HSV-1(17) (Brown et al., 1973), HSV-2(G) (Ejercito et al., 1968), HSV-1(F) (Ejercito et al., 1968), and HSV-2(333) ZAG (Nixon et al., 2013), a recombinant virus expressing the green fluorescent protein (GFP) were propagated on Vero cells. HSV-2 4674 (Nixon et al., 2013) was propagated on HaCAT cells. VD60 cells (Vero cells encoding gD-1 under the endogenous gene promoter (Ligas and Johnson, 1988)) were passaged in DMEM supplemented with 10% fetal bovine serum. Stocks of HSV-2 ΔgD-2 (ΔgD-/+gD-1) virus were propagated on complementing VD60 cells and titered on VD60 and Vero cells. Concentrated viral stocks were stored at −80° C. and diluted in PBS to the desired concentration when needed.

Construction of ΔgD-2::GFP. Plasmid pcDNA3-eGFP (13031; Addgene, Cambridge, MA, USA) was used as a template to PCR amplify the pCMV-eGFP-Neo$^r$ and OriE-Amp$^r$ regions flanked by Van91I restriction enzyme sites. The pCMV-eGFP-Neo$^r$ region was PCR-amplified using primers Fwd-pCMV and Rev-NeoR-Term (see Table 3 for a list of primers). The OriE-Ampr region was PCR amplified using primers Fwd-Origin and Rev-AmpR.

In parallel, genomic regions flanking the left and right of the US6 gene (gD) in HSV-2 were PCR amplified using purified viral DNA (HSV-2 strain 4674) as a template and primers LL-V91I-US6 plus LR-V91I-US6 for the left homology arm and primers RL-V91I-US6 and RR-V91I-US6 for the right homology arm (see Table 3 for sequence alignment). All four PCR fragments were gel purified, digested with Van91I (Fermentas Molecular Biology Tools, Thermo Scientific, West Palm Beach, FL, USA), ligated with Quick-Ligase [New England Biolabs (NEB), Ipswich, Massachusetts., USA], and transformed into NEB 5-α competent cells.

The resulting plasmid (eKO2-US6) was sequence verified and extracted from E. coli using an endotoxin-free miniprep kit (MO-BIO Laboratories, Carlsbad, CA, USA). HSV-2 DNA (1 μg) was co-transfected with 100 ng of eKO2-US6 into VD60 cells using Effectene (Qiagen, Valencia, CA, USA), according to the manufacturer recommendations.

At 4 d after transfection, plates were screened for green plaques and supernatants were collected and overlaid on fresh VD60 cells for 1 h, then washed and covered with 4% low-melting agarose prepared in Optimem (Invitrogen, Carlsbad, CA, USA). Single green fluorescent plaques were picked and purified 3 times using this method. Viral stocks were grown on VD60 cells, and noncomplemented virus was generated by harvesting infected cell lysates from Vero cells, as described for HSV-1 gD-deletion viruses (Ligas, 1988).

Genotypic confirmation of the gD deletion in ΔgD-2::GFP was performed by PCR. A primer set was used to confirm the presence of wild-type (WT) and ΔgD-2 virus DNA in the samples (primers RL-V91I-US6 and RL-V91IUS6), while another set of primers (Neo-Out and US8-Out) was used to amplify a DNA region comprising eKO2-US6 and the genomic target region. To confirm deletion of gD expression, Vero or VD60 cells were infected with parental WT or ΔgD-2 virus (grown on VD60 cells and thus competent for entry) at a multiplicity of infection (MOI) of 10 plaque-forming units (PFU)/cell (based on VD60 titer). After 1-h incubation, cells were washed twice with PBS, incubated in Optimem for 48 h at 37° C., and harvested and evaluated for gD expression by Western blot.

TABLE 3

PRIMERS USED IN CONSTRUCTING A GD-2 DELETION VIRUS.

| Region amplified | Primer Name | Sequence (5' to 3') |
|---|---|---|
| a. Primers for constructing eKO2-US6 (Van91I sites are underlined) | | |
| pCMV-eGFP-Neomycin resistance | Fwd-pCMV | TTT TTT TTC CAA GAA ATG GAG GCC TAC CCG GGT TGA CAT TGA TTA TTG ACT AGT TAT TAA TAG TAA TC (SEQ ID NO: 3) |
| | Rev-NeoR-Term | TTT TTT TTC CAA TCT ATG GAG CCC CAG CTG GTT CTT TCC (SEQ ID NO: 4) |
| pUC Origin-Ampicillin resistance | Fwd-Origin | TTT TTT TTC CAA TTT ATG GGC TGG GCT GTG TGC ACG AAC C (SEQ ID NO: 5) |
| | Rev-AmpR | TTT TTT TTC CAA AAG ATG GGC AGC GCA AAA CGC CTA ACC CTA AG (SEQ ID NO: 6) |
| Left US6 homology arm | LL-V91I-US6 | TTT TTT TTC CAT AAA TTG GAA AGG GAA CAG CGA CCA AAT GTC AC (SEQ ID NO: 7) |
| Right US6 homology arm | LR-V91I-US6 | TTT TTT TTC CAT TTC TTG GTG ATA CGC GAT GCA CAC GAA AAA CG (SEQ ID NO: 8) |
| | RL-V91I-US6 | TTT TTT TTC CAT AGA TTG GTT CCC CGC TCC CGT GTA CC (SEQ ID NO: 9) |
| | RR-V91I-US6 | TTT TTT TTC CAT CTT TTG GCG GGG GCG CCT GTA TCG G (SEQ ID NO: 10) |
| b. Primers for verifying gene deletion | | |
| WT and ΔgD virus | RL-V91I-US6 | TTT TTT TTC CAT AGA TTG GTT CCC CGC TCC CGT GTA CC (SEQ ID NO: 9) |
| | RR-V91I-US6 | TTT TTT TTC CAT CTT TTG GCG GGG GCG CCT GTA TCG G (SEQ ID NO: 10) |
| ΔgD virus | Neo-Out | GTA TAC CGT CGA CCT CTA GC (SEQ ID NO: 11) |
| | US8-Out | GGT GAC TTG GTG CGC CGC C (SEQ ID NO: 12) |

Sequence homologies for the PCR fragments used to construct the eKO2-US6 plasmid. Searching the published Addgene pcDNA3-eGFP (id:13031, 6159 bp) sequence for the pCMV-eGFP-Neomycin resistance primers using Blast2 yields a 1819 bp fragment:

```
Query    10 CGGGTTGACATTGATTATTGACTAGTTATTAATAGTAATC    49
            || ||||||||||||||||||||||||||||||||||||
Sbjct   229 CGCGTTGACATTGATTATTGACTAGTTATTAATAGTAATC   268  Plus strand
```
(SEQ ID NO: 13)

```
Query     1 AGCCCCAGCTGGTTCTTTCC                         20
            ||||||||||||||||||||
Sbjct  2010 AGCCCCAGCTGGTTCTTTCC                       1991  Minus strand
```
(SEQ ID NO: 14)

Searching the pcDNA3-eGFP sequence for the pUC Origin-Ampicillin resistance primers yields a 1754 bp fragment:

```
Query     1 GCTGGGCTGTGTGCACGAACC                        21
            |||||||||||||||||||||
Sbjct  4647 GCTGGGCTGTGTGCACGAACC                      4667  Plus strand
```
(SEQ ID NO: 15)

```
Query     1 GCAGCGCAAAACGCCTAACCCTAAG                    25
            |||||||||||||||||||||||||
Sbjct   204 GCAGCGCAAAACGCCTAACCCTAAG                   180  Minus strand.
```
(SEQ ID NO: 16)

Searching the blast.ncbi.nlm.nih.gov/Blast.cgi database for Left US6 homology arm of Herpes simplex virus (type 2) (taxid:10310) returned sequence from the Human HSV-2 strain HG52, complete genome:

BLAST for Left-US6 homology arm yields a 991 bp homologous region, 1029 bp fragment:

```
Query       1 AAAGGGAACAGCGACCAAATGTCAC                    25
              |||||||||||||||||||||||||
Sbjct  140020 AAAGGGAACAGCGACCAAATGTCAC                140044  Plus strand
```
(SEQ ID NO: 17)

```
Query       1 TGATACGCGATGCACACGAAAAACG                    25
              |||||||||||||||||||||||||
Sbjct  141011 TGATACGCGATGCACACGAAAAACG                140987  Minus strand.
```
(SEQ ID NO: 18)

BLAST for Right-US6 homology arm yields a 1072 bp homologous region, 1110 bp fragment:

```
Query       1 TTCCCCGCTCCCGTGTACC                          19
              |||||||||||||||||||
Sbjct  142204 TTCCCCGCTCCCGTGTACC                      142222  Plus strand
```
(SEQ ID NO: 19)

```
Query       1 CGGGGGCGCCTGTATCGG                           18
              ||||||||||||||||||
Sbjct  143276 CGGGGGCGCCTGTATCGG                       143259  Minus strand
```
(SEQ ID NO: 20)

When synthesizing HA genes, versions were designed that replaced codons in PR8 HA that had less than 9.5% representation in HSV-2 (G) gD with codons for their respective amino acid that had the highest representation in HSV-2 (G) gD.

TABLE 4

CODONS REPLACED IN CUSTOM SYNTHESIZED CODON-OPTIMIZED HA GENES.

| Original Codon | Prevalence in HA | Prevalence in gD | Altered Codon | Prevalence in gD | Replacements Made |
|---|---|---|---|---|---|
| ATA | 38.89% | 4.35% | ATC | 86.96% | 14 |
| ATT | 30.56% | 8.70% | ATC | 86.96% | 11 |
| GTA | 28.53% | 4.00% | GTC | 40.00% | 8 |
| CTT | 9.62% | 5.13% | CTG | 43.59% | 5 |
| TTA | 11.54% | 7.69% | CTG | 43.59% | 6 |
| TCT | 28.13% | 7.69% | TCG | 69.23% | 9 |
| TCA | 53.13% | 0.00% | TCG | 69.23% | 17 |
| CCT | 5.00% | 0.00% | CCC | 65.12% | 1 |
| CCA | 50.00% | 6.98% | CCC | 65.12% | 10 |
| ACT | 23.33% | 4.35% | ACG | 39.13% | 7 |

TABLE 4-continued

CODONS REPLACED IN CUSTOM SYNTHESIZED
CODON-OPTIMIZED HA GENES.

| Original Codon | Prevalence in HA | Prevalence in gD | Altered Codon | Prevalence in gD | Replacements Made |
|---|---|---|---|---|---|
| ACA | 46.67% | 4.35% | ACC | 52.17% | 14 |
| GCA | 45.45% | 7.32% | GCC | 60.98% | 15 |
| CAT | 53.85% | 9.09% | CAC | 90.91% | 7 |
| TGT | 62.50% | 0.00% | TGC | 100.0% | 10 |
| AGT | 53.33% | 8.33% | AGC | 91.67% | 8 |
| AGA | 52.17% | 0.00% | CGC | 58.33% | 12 |
| AGG | 47.83% | 0.00% | CGC | 58.33% | 11 |

Figure 7:
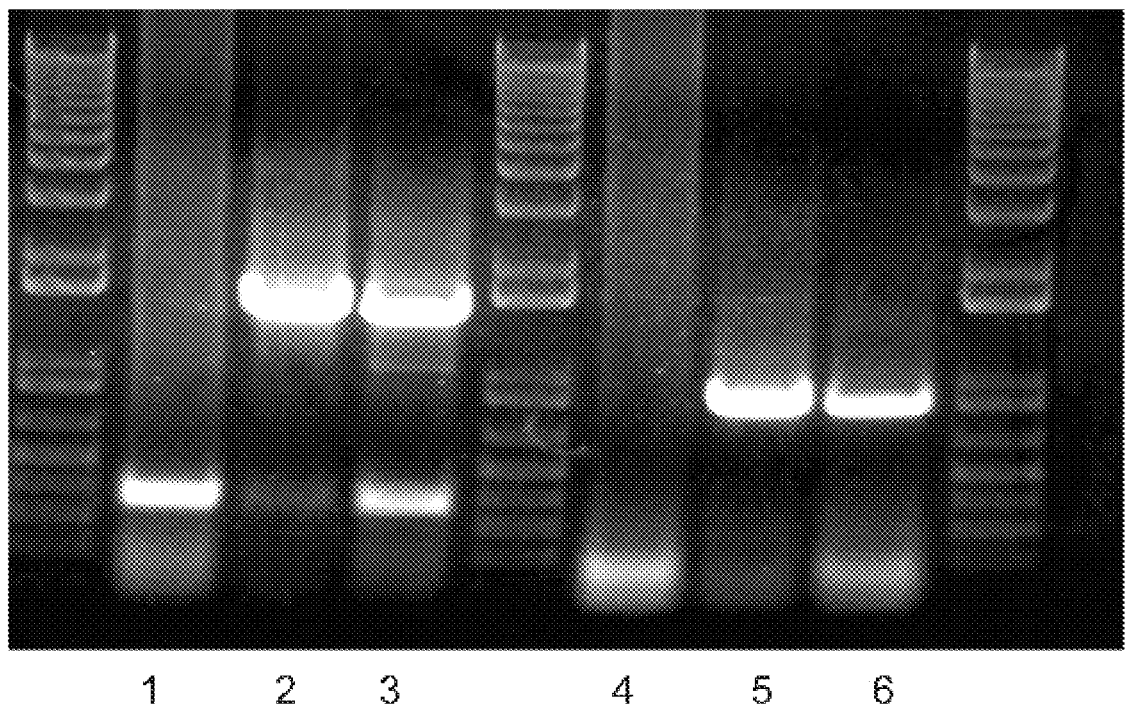
Figure 9:
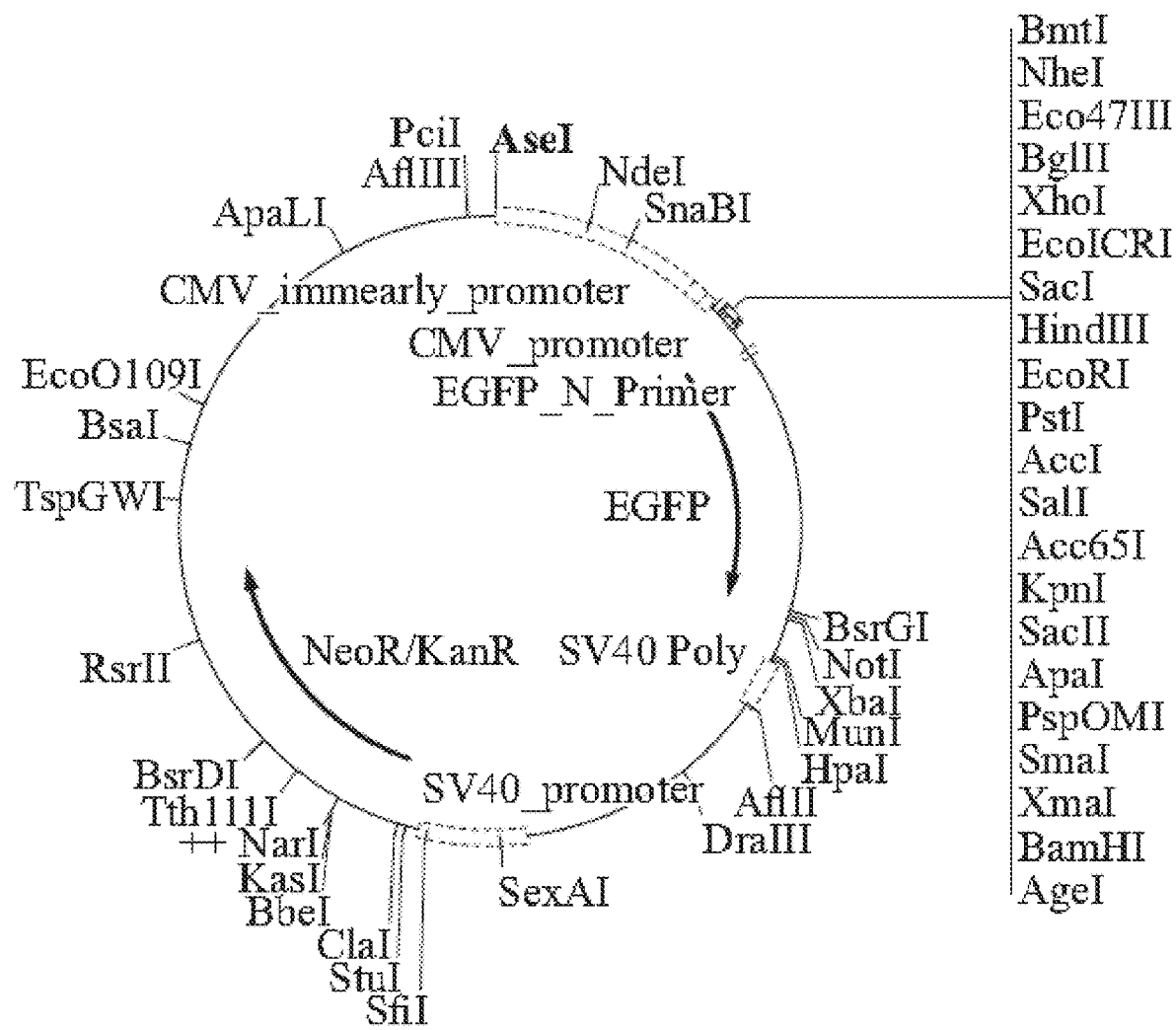
Figure 10:
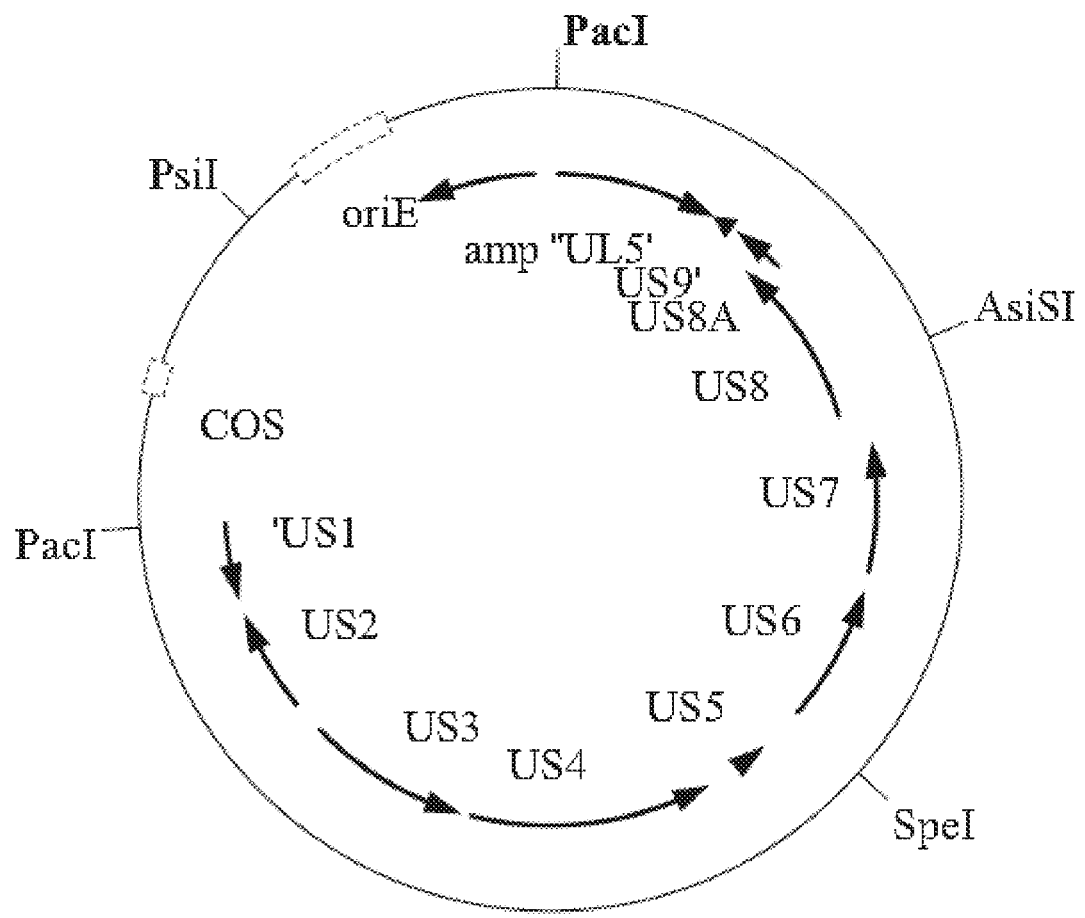
Figures 11A, 11B, 11C:
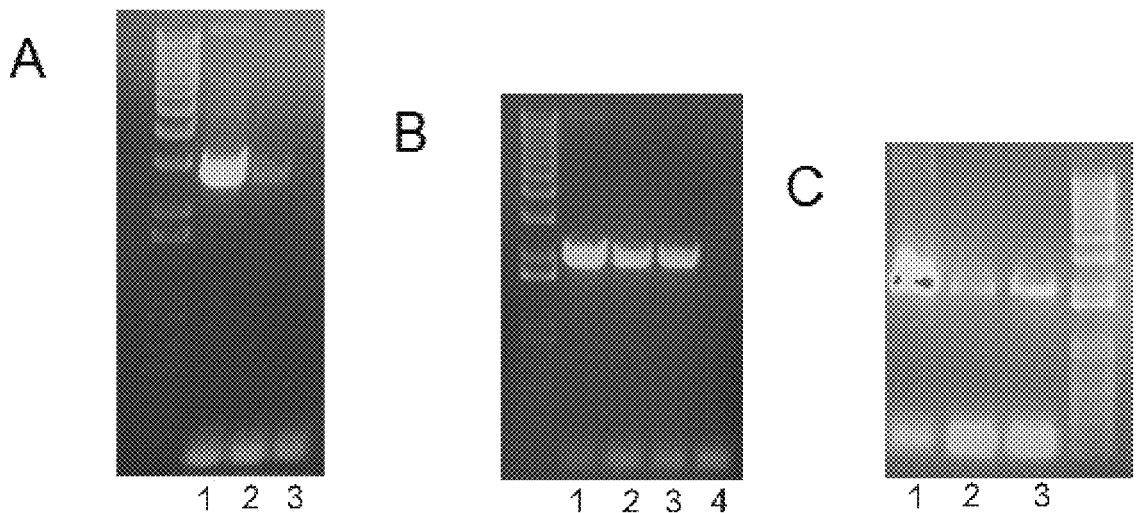

The presence of chimeric gD::HA in recombinant viruses was verified by PCR (see FIG. 7). The lanes from left to right are as follows: Lane 1; ΔgD-2genomic DNA, Lane 2; ΔgD-2::FL HA nOP genomic DNA, Lane 3; pBJJ1 plasmid DNA, Lane 4; ΔgD-2genomic DNA, Lane 5; ΔgD-2::HL HA nOP genomic DNA, and Lane 6; pBJJ2 plasmid DNA. Primers used for PCR amplification were located just upstream and downstream of the HA extracellular domains. No exogenous promoter was inserted into the expression cassette. As a result, chimeric gene expression was regulated by the endogenous promoter. Sanger sequencing was used to verify the proper construction of chimeric gD::HA genes in recombinant viruses. Upon genetic verification, 6-8 week old C57BL/6 mice were prime-boost vaccinated at days 0 and 21 with ΔgD-2::FL HA nOP or ΔgD-2::HL HA OPT in parallel with the parental ΔgD-2::RFP strain and a control group mock-vaccinated with VD60 cell lysates. 21 days post-boost, the mice were skin challenged with a 10× LD90 of HSV-2 4674 to determine whether anti-HSV immunity had been compromised.

Mice that were vaccinated with ΔgD-2::FL HA nOP and ΔgD-2::HL HA OPT are fully protected against HSV-2 challenge but do not form anti-HA IgGs (see FIG. 8). Mice were prime-boost vaccinated on days 0 and 21 with a control VD60 cell lysate or 1×106 PFU of ΔgD-2::FL HA nOP, ΔgD-2::HL HA OPT, or ΔgD-2::RFP. At day 42, mice were challenged with a 10× LD90 of HSV-2 4674. Mice vaccinated with ΔgD-2::FL HA nOP and ΔgD-2::HL HA OPT were fully protected from challenge. (See FIG. 8A) At day 40 post-prime, mice were bled to look at serum antibodies. ELISAs performed against soluble PR8 HA show the absence of HA-specific IgGs in mice. (See FIG. 8B)

Construction of ΔgD-2::PCMV-HA viruses and HA expression. It was investigated if it would be more immunogenic to insert non-chimeric HA genes into the ΔgD genome in cassettes containing a constitutive promoter and poly-adenylation sequence. To accomplish this, the synthesized PR8 HA genes were restriction cloned into expression plasmid pEGFP-N1 (Addgene). HA genes were inserted in between xbaI and HindIII sites and replaced EGFP in the plasmid.

Figure 18:
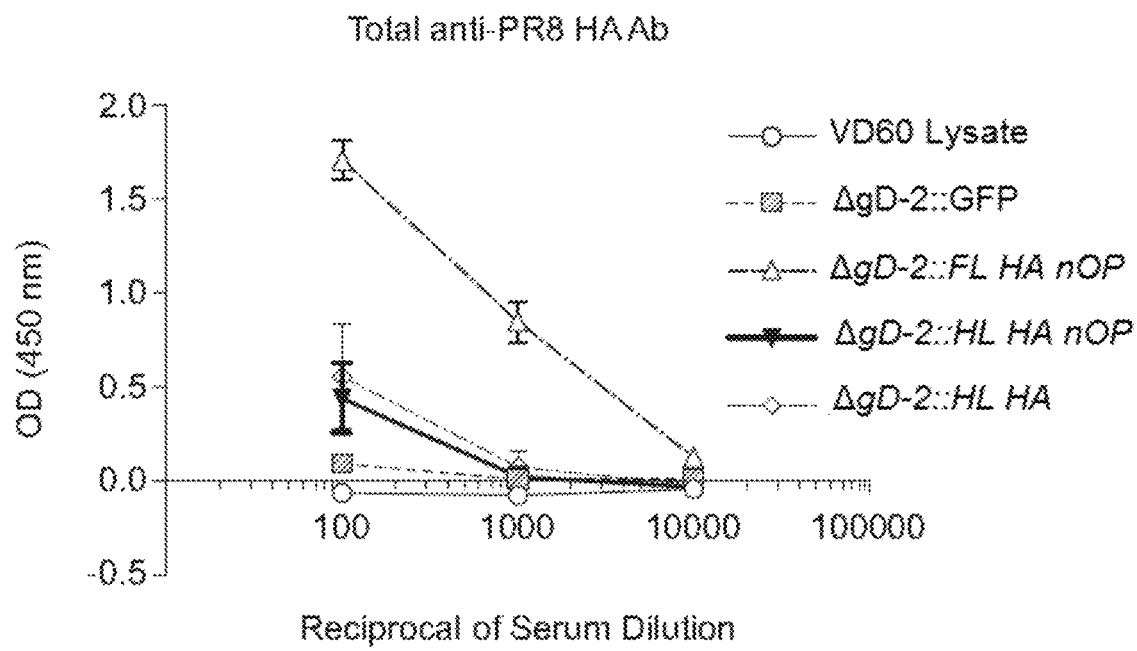
FIG. 18: Anti-HA antibodies elicited by vaccination with various PR8 influenza A virus (IAV) hemagglutinin (HA) HSV-2 recombinants (see Legend in figure).
Figure 19:
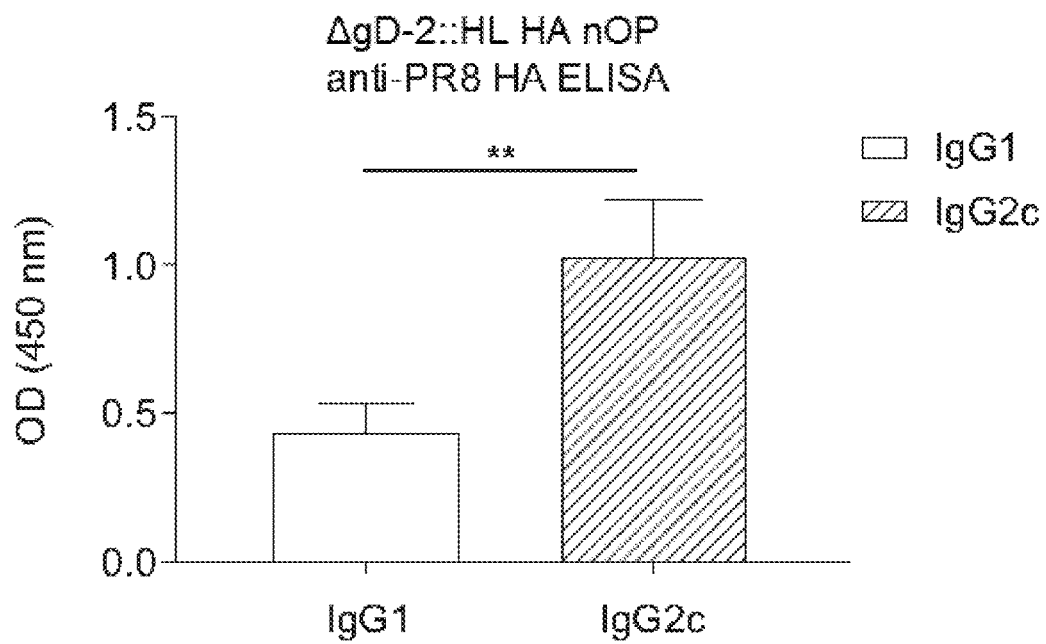
FIG. 19: Anti-HA antibody isotype elicited by vaccination with the HSV-2 recombinant ΔgD-2::FL HA nOP. **$p<0.01$.

Mice were vaccinated with ΔgD-2::PCMV-FL HA nOP. The mice were prime vaccinated with 5×106 PFU of each virus (See FIG. 18 legend for the different viruses used). n=5 mice/group, except 10 mice for ΔgD-2::FL HA nOP. Five (5) of the ΔgD-2::FL HA nOPmice were boosted with a stalk HA expressing ΔgD-2, 5 μg/mL of purified PR8 HA was used as the source of antigen. A goat anti-mouse Ig Ab was used for the total Ab ELISA. Day 14 post-prime anti-PR8 HA ELISA showed serum from mice vaccinated with stalk HA (ΔgD-2::FL HA nOP) showed an overall Ab response, but it did not register above background on the isotype ELISAs. (See FIG. 18) Importantly, vaccination with ΔgD-2::PCMV-FL HA nOP (β3χ4) yielded significantly more IgG2c than IgG1 (See FIG. 19). Vaccination with the full-length HA induced the largest anti-HA response and this response is predominantly IgG2c. This is consistent with identical IgG isotype responses being obtainable with the recombinant virus vaccine to exogenous antigens as to endogenous HSV proteins.

Figure 12:
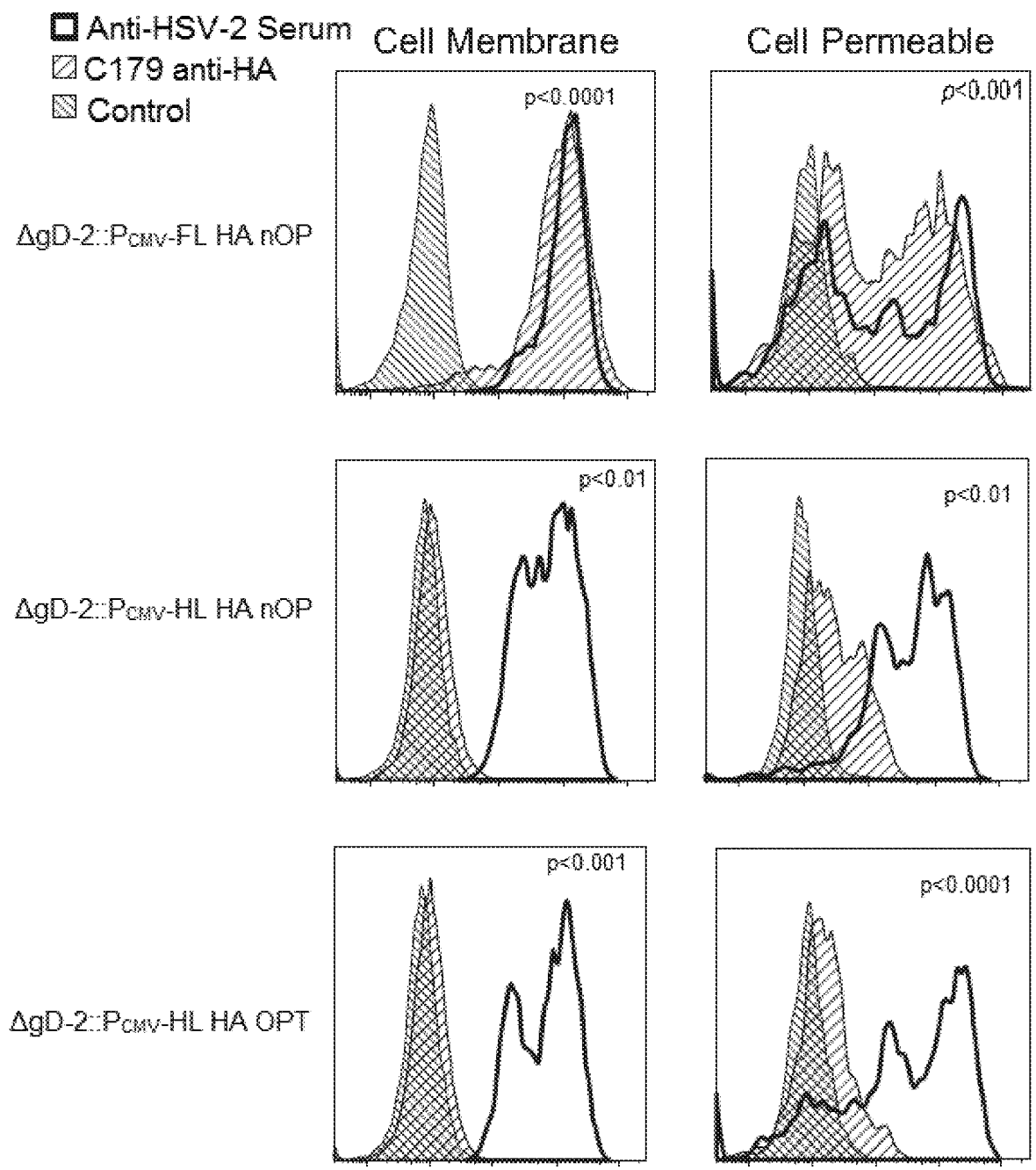

ΔgD-2::PCMV-HA recombinant viruses all express HA. As shown in FIG. 12, VD60 cells were infected with 3 MOI of ΔgD-2::PCMV-FL HA nOP, ΔgD-2::PCMV-HL HA nOP, or ΔgD-2::PCMV-HL HA OPT. At 16 hours post-infection, cells were harvested and stained for HSV-protein and HA expression. HSV protein expression was measured using serum from mice vaccinated with ΔgD-2::RFP. HA expression was measured using monoclonal anti-HA stalk IgG C179. Cells were stained with either cell permeable or cell impermeable methods. Statistics were calculated by student's t test of geometric means between control fluorescence and fluorescence in wells stained for HA expression. Only β3χ4 induced high levels of HA expression in infected cell membranes, but all three viruses induced expression as measured by cell-permeable staining.

Figure 13:
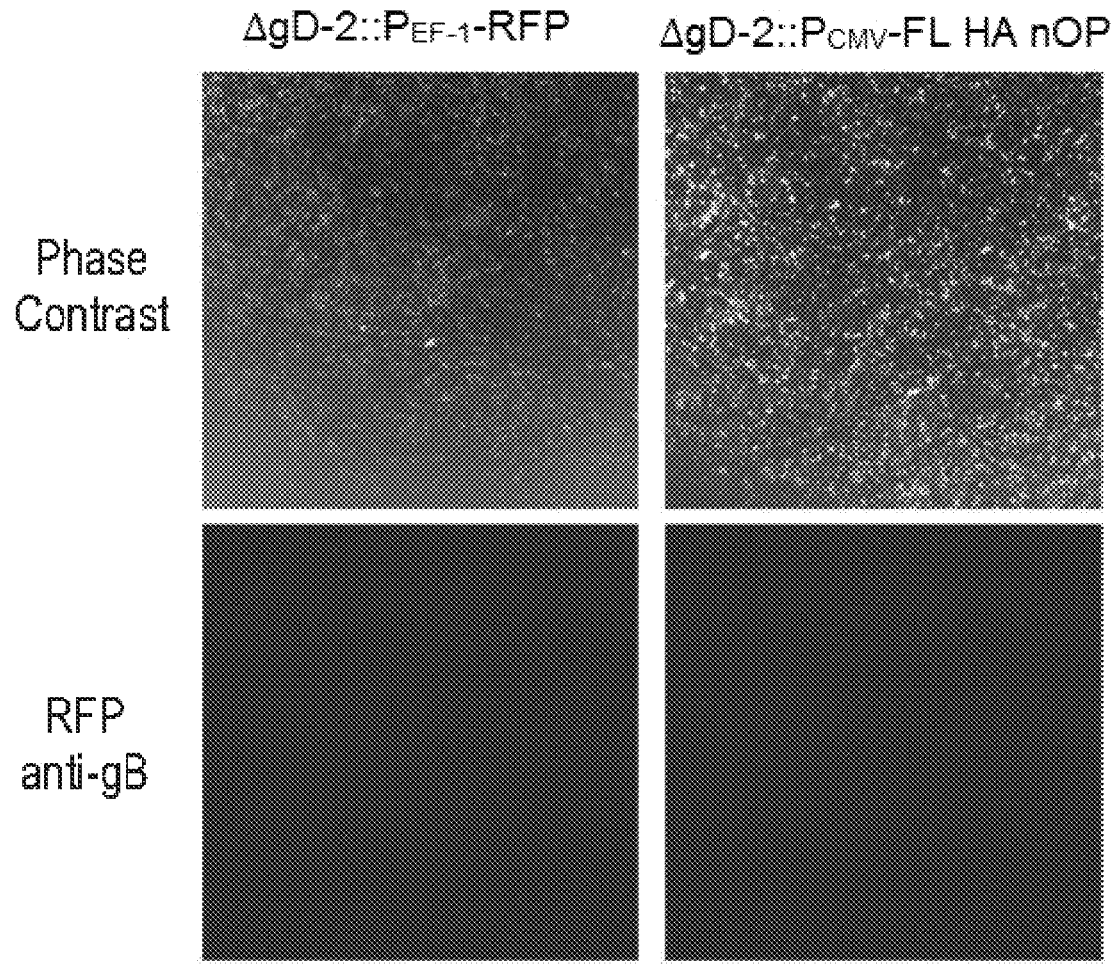

To determine if the insertion of full-length PR8 HA into ΔgD-2 would introduce a novel route of cell entry, Vero cells were infected with 0.01 MOI of ΔgD-2::P-CMV-FL HA nOP or ΔgD-2::PEF1α-RFP. At 120 hours post-infection, there were no signs of productive infection. Additionally, 5 C57BL/6 mice were given subcutaneous injections with 5×106 PFU of ΔgD-2::PCMV-FL HA nOP and monitored daily for one week. They showed no signs of disease or distress. Additionally, an in vitro assay was conducted in which non-complementing Vero cells were infected with titrations of either ΔgD-2::PCMV-FL HA nOP and ΔgD-2::PEF1α-RFP. At 70 hours post-infection, the cells were fixed and stained for HSV-2 glycoprotein B (gB) Staining shows the presence of isolated infected cells at a 10-3 dilution of each virus, but no evidence of cell-to-cell viral spread (See FIG. 13). This is not surprising, given that the influenza A and B proton pump genes, both named M2, are required the mediate release of virions from the endosome. Since β3χ4-6 do not contain either proton pump gene, they lack a mechanism to exit the endosome of cells after entry.

Example 2

Designing the HIV constructs to express in HSV-2 ΔgD virus: Producing a vaccine vector in which a glycoprotein antigen from HIV would be expressed from the ADCC-inducing HSV-2 ☐gD vector was investigated. The rationale for using this vector is that it elicits non-neutralizing, ADCC-inducing IgG antibodies against HSV, and this type of immune response has been correlated with protection in the only HIV vaccine trial to show any efficacy thus far (Haynes, Gilbert et al. 2012). For the glycoprotein antigen, the transmitted/founder clone of Env gp145 was chosen, which lacks the cytoplasmic tail, from donor CH505 in the CHAVI001 acute HIV-1 infection cohort, as this well-characterized HIV-1 clade C glycoprotein is thought to be representative of those that pass the bottleneck of infection in a region of high HIV prevalence (Liao, Lynch et al. 2013). HIV Env is not expressed particularly well in the context of natural infection and often not expressed well exogenously, so steps were investigated to enhance antigen expression in our construct. Env gp145 was found to be incorporated more efficiently into virus like particles (VLPs) than full length, and replacing the Env signal peptide and transmembrane domains with corresponding domains from host proteins or other viral glycoproteins increased incorporation into VLPs further (Wang, Liu et al. 2007). To provide efficient incorporation of HIV Env into HSV VLPs, a chimera of the ectodomain of HIV Env with the signal peptide and transmembrane cytoplasmic tail of HSV-2 gD was constructed. The signal peptide of HSV2 gD is 25 residues in length and the ectodomain is 306 residues total (Eisenberg, Long et al. 1984, Nicola, Willis et al. 1996). The allelic exchange construct was generated by Gibson assembly (Gibson, Young et al. 2009). Briefly, oligonucleotide primers were synthesized to amplify from HSV2 strain G genomic DNA arms of homologous sequence ~800 bp 5' to the 25th codon of HSV2 US6 and ~800 bp 3' to the 306th codon of HSV2 US6. The insert was amplified from the CH505 TF gp145 expression plasmid HV1300631 (gift of Huaxin Liao, Duke University) with primers that encompassed the 30th codon to codon 680. The fragments were cloned into pUC19 between EcoRI and BamHI restriction sites.

Example 3

Introduction

Functional in vitro macrophage antibody-dependent cell-mediated killing (ADCK) assay using an RFP-expressing HSV-2 ΔgD strain (as made in Example 1): The single-cycle herpes simplex virus type 2 (HSV-2) strain deleted in glycoprotein D (ΔgD-2) elicits sterilizing anti-HSV immunity by inducing antibodies that bind and activate Fcγ-receptors (FcγRs). Murine FcγRIV is highly activated in the presence of serum from vaccinated mice and is expressed on macrophages, monocytes, and neutrophils. The precise mechanisms of cell killing through FcγRs are not well understood and additional tools are needed. FcγR-binding antibodies mediate killing of HSV-infected cells by binding antigens on infected cell and then binding and activating FcγRs on innate leukocytes. This precipitates antibody-dependent cell-mediated cytotoxicity and phagocytosis (ADCC and ADCP), here referred to as antibody-dependent cell-mediated killing (ADCK). Current assays face many limitations including, but not limited to, inflexible target and effector cell lines, artificial antigen presentation systems, indirect or separate outputs for ADCC and ADCP, and the use of cumbersome radioactive isotopes.

To overcome these restrictions, a quantitative in vitro assay was constructed to study ADCK in response to anti-HSV antibodies. A ΔgD-2 variant that highly expresses the gene for red fluorescent protein (rfp) was used to mark infection. RFP and cell viability markers were then used to identify live-infected target cells, the decreasing proportion of which was determined to be the result of cell killing. FACS analysis was used to quantify the decreasing proportion of live-infected target cells after co-culture with macrophages.

Using the new assay, it was shown that serum from mice vaccinated with ΔgD-2 induces significant amounts of ADCK by both immortalized macrophage cell lines and bone marrow derived macrophages (BMDMs) from both mice and guinea pigs. Live-imaging of the assay using Raw macrophages shows that killing readouts cannot easily be attributed to cytotoxicity or phagocytosis, but that the processes can occur simultaneously, underlining the importance of using an assay which measures both. Additionally, ADCK was eliminated when BMDMs from FcγR$^{-/-}$ mice were used, indicating that the primary readout is FcγR dependent and that the assay is amenable to studying ADCK in different knockout mouse strains. This assay allows for the precise study of ADCK and its associated genes and FcγRs in different species and animal models.

Traditionally, ADCC was measured by cumbersome $^{51}$Cr release assays, but a number of FACS methods have been developed to measure ADCC in response to different antigens and antibodies. The collective term for these methods is Rapid fluorometric ADCC (RFADCC). In these assays, target cells are stained with a persistent membrane die and a live-dead marker that dissipates upon the initiation of apoptosis. ADCC activity is then measured as the decrease in proportion of membrane dye$^+$ cells that are also live-dead$^+$. In similar assays, ADCP is measured by the proportion of macrophages that are marked by the phagocytosis of fluorescent cells. However, as the data herein show, ADCC and ADCP cannot be cleanly separated by these methods, so they are referred to collectively in this text as antibody-dependent cell-mediated killing (ADCK). The prior art assays have some additional drawbacks, as they are usually restricted in their choice of antibody or effector cell. A similar assay was used in Petro et al. 2015, but the ability of HSV to infect, replicate in, and kill both target and effector cells limited the utility of the assay for studying immune cells and their FcγRs (Petro et al., 2015).

ΔgD-2 is a single-cycle virus in non-complementing cells and was recently shown not to induce dendritic cell death in vitro. It was investigated whether a brightly fluorescent ΔgD-2 strain would allow for precise investigation of the cellular mechanisms of ADCK. An RFP expressing ΔgD-2 (ΔgD-2::RFP) strain was constructed and developed with an RFADCK assay that precisely measures the effector activity of macrophages on HSV-2 ΔgD-2:RFP infected cells in vitro. The assay was validated for both immortalized and primary cell lines using J774 cells, Raw 264.7 macrophages, and bone marrow-derived macrophages (BMDMs). Unlike current RFADCC assays, this method simulates an infectious environment, measures both ADCC and ADCP, and is profoundly flexible, allowing for the use of polyclonal animal sera and different cell lines and mouse strains.

Cells Lines: Vero (CCL-81; ATCC, Manassas, VA) and VD60 cells (Vero cells containing multiple copies of gD-1 under the endogenous gene promoter) were passaged in DMEM (Thermo Fisher Scientific, Waltham, MA) supplemented with 5% fetal bovine serum (FBS, Gemini Bio-Products, West Sacramento, CA) and 10 U/ml penicillin, and 10 µg/ml streptomycin sulfate (Thermo Fisher Scientific). Bone-marrow derived macrophages (BMDMs) were obtained as previously described from C57B1/6 mice. Bone marrow precursors were stored in DMEM supplemented with 50% FBS and 10% DMSO (Sigma-Aldrich, St. Louis, MO) if not used immediately. Mouse BMDMs were differentiated using the supernatant from L929 cell cultures (ATCC). Guinea pig BMDMs were differentiated using recombinant human M-CSF (BioLegend, San Diego, CA). Raw 264.7, J774.1, and HEK 293 cells (ATCC) were passaged in DMEM supplemented with 10% FBS and 1% Pen-strep.

Creation of ΔgD-2::RFP and Virus Propagation. VD60 cells were co-transfected with HSV-2 ΔgD:GFP (ΔgD-2) genomic DNA and cosmid DNA containing 40 kB of the HSV-2 genome in which the US6 gene was replaced with tdtomato downstream of an EF1α promoter. Resultant virus was plaque purified three times using RFP expression as a marker of homologous recombination. The purified ΔgD-2::RFP virus was verified by PCR and sequencing.

ΔgD-2 and ΔgD-2::RFP were propagated on VD60 cell, which complement the gD deletion and allow for multiple rounds of replication. All viral strains were titered by serial dilution and propagation on their respective cell types.

Animals: Female C57BL/6 mice, aged 4-6 weeks, obtained from Jackson Laboratory (JAX, Bar Harbor, ME) were used to obtain serum. Male C57BL/6 mice, aged 4-6 weeks, were obtained from JAX and bone marrow cell suspensions were isolated by flushing their femurs with DMEM supplemented with 10% PBS and 1% Pen-strep. Female Hartley guinea pigs, aged 5-6 weeks, were purchased from Charles River laboratories (Wilmington, MA). Bone marrow cell suspensions were isolated by flushing femurs and tibias with DMEM supplemented with 10% FBS and 1% Pen-strep. Vaccinations were administered by subcutaneous injection. All procedures were approved by the Albert Einstein College of Medicine Institutional Animal Care and Use Committee Immunization: Mice or guinea pigs, aged 6-8 weeks, were prime vaccinated subcutaneously with 5×106 plaque forming units (PFU) of HSV-2 ΔgD::RFP or an equal volume of VD60 cell lysate in phosphate-buffered saline (PBS) to a total volume of 200 μL. Animals were boosted with the same dose 21 days later.

Antibody-dependent cell killing assay: Bone Marrow Derived Macrophages (BMDMs), J774.1 macrophages, and Raw 264.7 macrophages were incubated in LPS (Sigma-Aldrich) for 12 hours prior to co-culture with HEK 293 cells (ATCC). HEK 293 cells were double stained with PKH67 membrane (Sigma-Aldrich) and Tag-it Violet™ (Biolegend) dyes according to manufacturer's instructions. HEK cells were infected with HSV-2 ΔgD:: RFP at a MOI of 3 in serum free DMEM 4 hours before co-culture. The infection media was removed after 3.5 hours and was replaced with a 1:5 dilution of heat-inactivated mouse or guinea pig serum collected at day 40 from mice prime-boost injected as described previously with either HSV-2 ΔgD:: RFP or VD60 cell lysate. HEK 293T cells were incubated in serum for 30 minutes at 37° C. and then added to macrophage cultures in 96-well tissue culture plates (Corning Inc, New York City, NY). The co-cultures were incubated for 12 hours, then fixed and analyzed by flow cytometry on a LSRII (BD Biosciences, Franklin Lakes, NJ). For live-imaging experiments, Raw 264.7 macrophages and HEK 293 cells were co-cultured at a ratio of 10:1 on glass-bottom 96-well plates (Matrical Bioscience, Spokane WA) and imaged with an inverted NIKON Eclipse TiE microscope using NIS Elements software with deconvolution.

Statistical Analyses: Data was compiled in GraphPad Prism (GraphPad Software, Inc., La Jolla, CA). Statistical analysis using the tests noted in the figures were also done using GraphPad Prism. Statistical significance is indicated in figures as *, p<0.5; ***, p<0.001.

Results

Figure 14A:
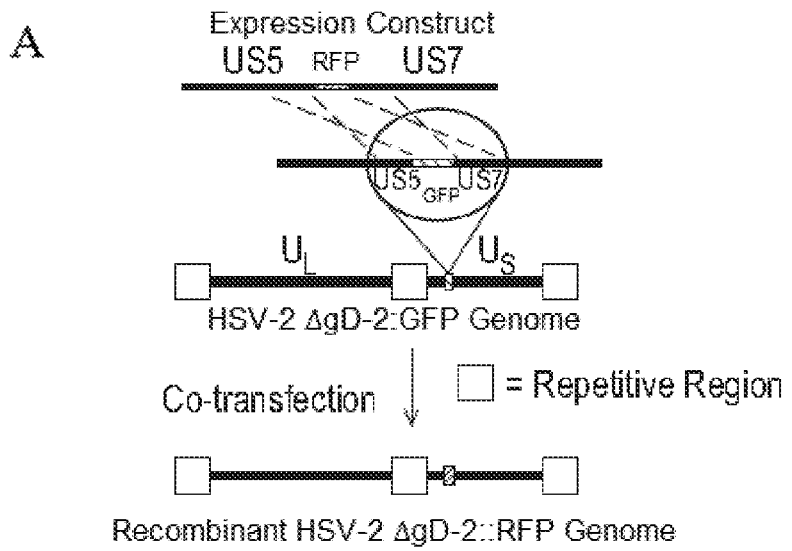
Figures 14B, 14C:
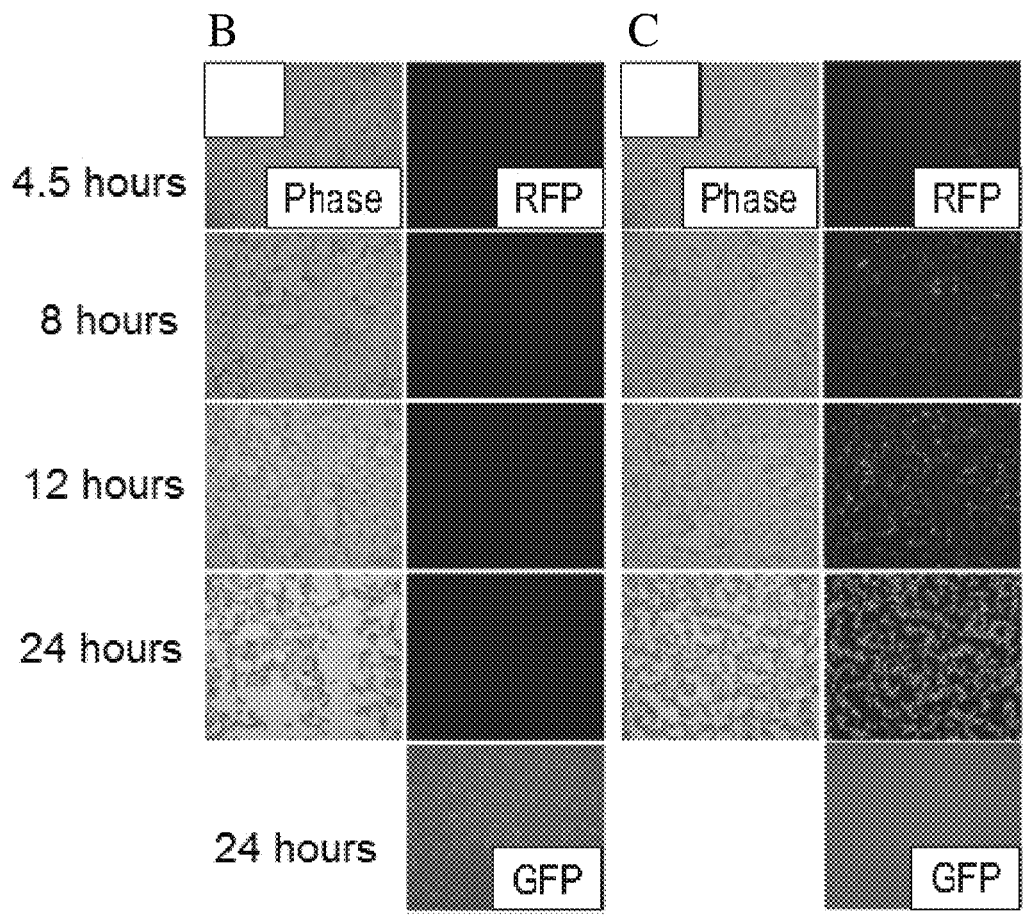
Figures 14D, 14E:
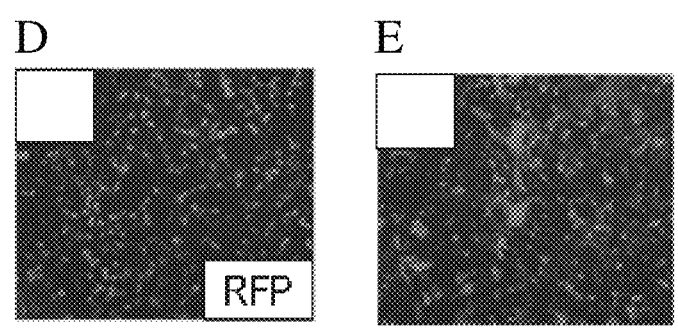

Inserting rfp into US6 of HSV-2 ΔgD does not alter viral growth phenotype. Vero cells were infected with HSV-2 ΔgD-2::GFP at a multiplicity of infection (MOI) of 1 to determine the kinetics of GFP expression. Fluorescent microscopy was used to visualize GFP expression, which was low even at 24 hours post-infection (FIG. 14B). We replaced the GFP in the US6 locus of ΔgD-2 with an RFP under an EF1α promoter to create ΔgD-2::RFP (FIG. 14A). To determine the kinetics of RFP expression, non-complementing Vero cells were infected with 1 MOI of HSV-2 ΔgD:: RFP or ΔgD-2. Visualization by fluorescent microscopy showed that RFP expression began in ΔgD-2::RFP at 4.5 hours post-infection and continued to increase up to 24 hours post-infection (FIG. 14C). Phase-contrast imaging showed that viral infection with ΔgD-2::RFP appears similar to that of the parental ΔgD-2 strain in Vero cells (FIGS. 14B and 14C). Infection with ΔgD-2::RFP at an MOI of 3 resulted in syncytia formation in VD60 (FIG. 14E) but not Vero cells (FIG. 14D) at 12 hours post-infection, indicating that the virus maintained its single-cycle replication phenotype. The introduction of pEF1α::RFP into the gD locus of ΔgD-2::GFP elicited robust RFP expression while maintaining the viral kinetics and single-cycle phenotype of the parental ΔgD-2 strain.

Serum from ΔgD-2::RFP vaccinated mice induces significant ADCK in the RFADCK assay. In order to measure the levels of ADCK activity elicited by serum from ΔgD-2::RFP vaccinated mice, an in vitro protocol was developed based on previous RFADCC assays. Target HEK 293T cells were stained with a membrane dye and a live-dead marker and infected with ΔgD-2::RFP at an MOI of 3. Infected target cells were incubated for 3.5 hours before infection media was removed and media or mouse serum was added for an additional 30-minute incubation. The infected HEK 293T cells were co-cultured for 12 hours with J774.1 murine macrophage cells which had been stimulated with LPS 12 hours prior. Based on previously reported assays, we used an effector to target cell ratio of 10:1. At this ratio, serum from ΔgD-2::RFP vaccinated mice induced killing of approximately 70.5% of highly infected (RFP$^{high}$) target cells (FIG. 15B). This was significantly more than the 49.3% killed in the absence of serum (p<0.05). It was investigated whether only RFP$^{high}$ cells would significantly decrease, since RFP in the model is a surrogate for viral protein expression and cells expressing higher levels these proteins will bind more antibodies cross-link FcγRs, initiating ADCK. There was no significant difference in the killing of RFP$^{mid}$ or RFP$^{mid+high}$ (total infected cells) between the two treatment groups (FIG. 15B). Infected target cells were defined as double positive HEK293T cells that expressed RFP in cultures lacking effector cells. RFP$^{high}$ cells were defined as cells expressing RFP above the mean intensity of infected target cells. RFP$^{mid}$ cells were defined as all infected target cells expressing RFP below the mean intensity (FIG. 15A).

ADCK is significantly increased in the presence of serum from mice vaccinated with ΔgD-2::RFP compared to serum from mice vaccinated with a control cell lysate. Infected HEK 293 cells were incubated with serum from mice vaccinated with either ΔgD-2::RFP or a control VD60 cell lysate to determine whether killing mediated by different immortalized macrophage cells lines was caused by antigen-specific ADCK. For each treatment group, the proportion of RFP$^{high}$ cells after 16 hours of co-culture was compared to that of parallel assays lacking serum. In cultures containing J774.1 macrophages, serum from ΔgD-2::RFP vaccinated mice induced significantly more killing of RFP$^{high}$ cells than serum from VD60 mock-vaccinated mice (p<0.001; FIG. 15C). A similar trend was seen in cultures containing Raw 264.7 macrophages (p=0.09). Additionally, for both J774.1 and Raw 264.7 macrophages, ADCK measured in cultures containing serum from VD60 mock-vaccinated mice were indistinguishable from cultures lacking serum (mean % difference=−5.9±7.6, −0.3±3.5). This indicates that non-specific antibodies do not induce killing in our assay. These results confirm that the ADCK measured in the RFADCK assay is a result of HSV-specific antibodies elicited by vaccination with ΔgD-2::RFP.

Figure 16:
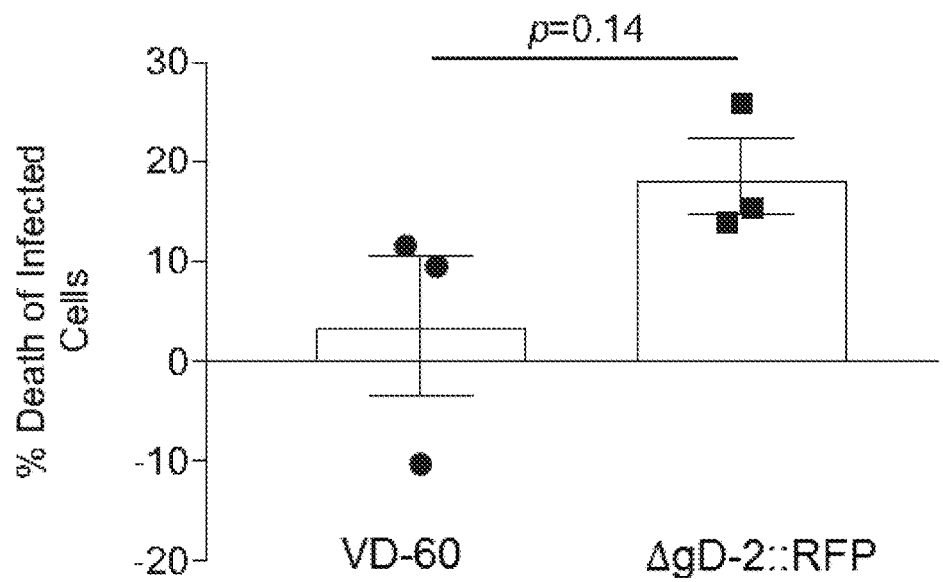
FIG. 16. ADCC and ADCP are not easily distinguishable but are mediated by Raw 264.7 macrophages in the presence of serum from HSV-2 ΔgD-2::RFP vaccinated mice. Quantification of the number of infected cells that died during three movies suggests that the addition of serum from HSV-2 ΔgD-2::RFP vaccinated mice induces more killing than serum from mice given a control VD60 cell lysate when compared to movies taken of co-cultures lacking of serum ($p=0.14$, mean=18.5, 3.7, n=58 infected cells for both groups). Images represent a partial frame of one movie taken at 60× magnification. Images were taken every 15 minutes for 24 hours. HEK 293 cells were used as target cells. Raw 264.7 cells were used as macrophages. All assays were done at a 10:1 ratio of effector to target cells. Statistics were done using a student's t test.

Tracking of infected cells by live-imaging of ADCK assay shows that cytotoxicity and phagocytosis are not mutually exclusive. ADCK assay was carried out as described above with the exceptions that glass-bottom 96-well plates were used and the effector cells were Raw 264.7 murine macrophage cells which have been shown to carry out similar amounts of ADCC and ADCP. The assays were imaged on a deconvolution microscope at 60× magnification approximately every 15 minutes for 24 hours. Infected cells are RFP+. Uninfected HEK293 cells are highly Mem+ and Live/Dead+. Macrophages are unstrained. FIG. 15A indicates that different types of cell killing of infected cells (white arrows) by macrophages are observed at the indicated time points: Macrophages (*) cluster around the left infected cell over time, and the right infected cell undergoes apoptotic blebbing observed at 4.5 hours. These resulting blebs are quickly phagocytosed by macrophages, which fluoresce with RFP observed at 7.5-hours. The controlled apoptosis of this infected cell indicates that ADCC has occurred, but phagocytosis by, and subsequent fluorescence of, macrophages would be measured by flow analysis as ADCP. The total number of infected cells captured was low, leading to high variability (n=58 infected cells/group), but quantification of killing of infected cells across movies from three experiments shows similar mean ADCK in the presence of Raw 264.7 macrophage cells as was measured previously by RFADCK assay (meanRFADCK=18.8%, meanmovie=18.5% killing; FIG. 15C, 16B).

Figures 17A, 17B:
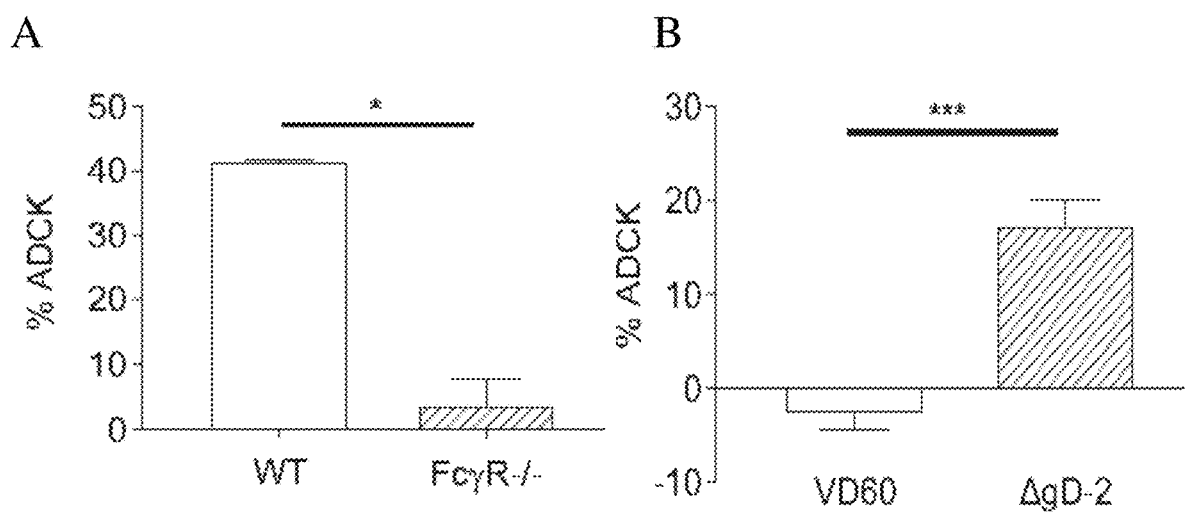
FIGS. 17A-17B. The ADCK assay can be adapted to knockout mouse strains and other model organisms.

ADCK activity by bone marrow-derived macrophages is FcγR-dependent. RFADCK assays were performed with bone marrow-derived macrophages (BMDMs) from wild-type and FcγR−/− mice to determine whether observed ADCK was FcγR dependent. ADCK activity was defined as the decrease in RFPhigh cells compared to parallel cultures with serum from VD60 lysate mock-vaccinated mice. At an effector to target cell ratio of 10:1, wild-type BMDMs killed significantly more infected target cells than FcγR−/− BMDMs in the presence of serum from HSV-2 ΔgD-2::RFP vaccinated mice (p<0.05; FIG. 17A). Additionally, killing of RFPhigh cells by FcγR−/− BMDMs in the presence of serum from HSV-2 ΔgD-2::RFP vaccinated mice was indistinguishable from killing in the presence of serum from VD60 lysate mock-vaccinated mice (mean % difference=3.6±4.0), indicating that ADCK activity measured in our assay is entirely FcγR dependent.

RFADCK using guinea pig bone marrow-derived macrophages recapitulates murine results. To determine the ability of another species' effector cells to carry out ADCK in our assay, guinea pig BMDMs were co-cultured with ΔgD-2::RFP infected HEK 293 cells in the presence of serum from ΔgD-2 vaccinated, VD60 lysate mock vaccinated, or naïve guinea pigs. The killing of RFPhigh cells in parallel co-cultures containing serum from naïve animals was used as the baseline. In the presence of serum from ΔgD-2 vaccinated animals, guinea pig BMDMs carried out significant ADCK (p<0.001; FIG. 17B).

Figure 20:
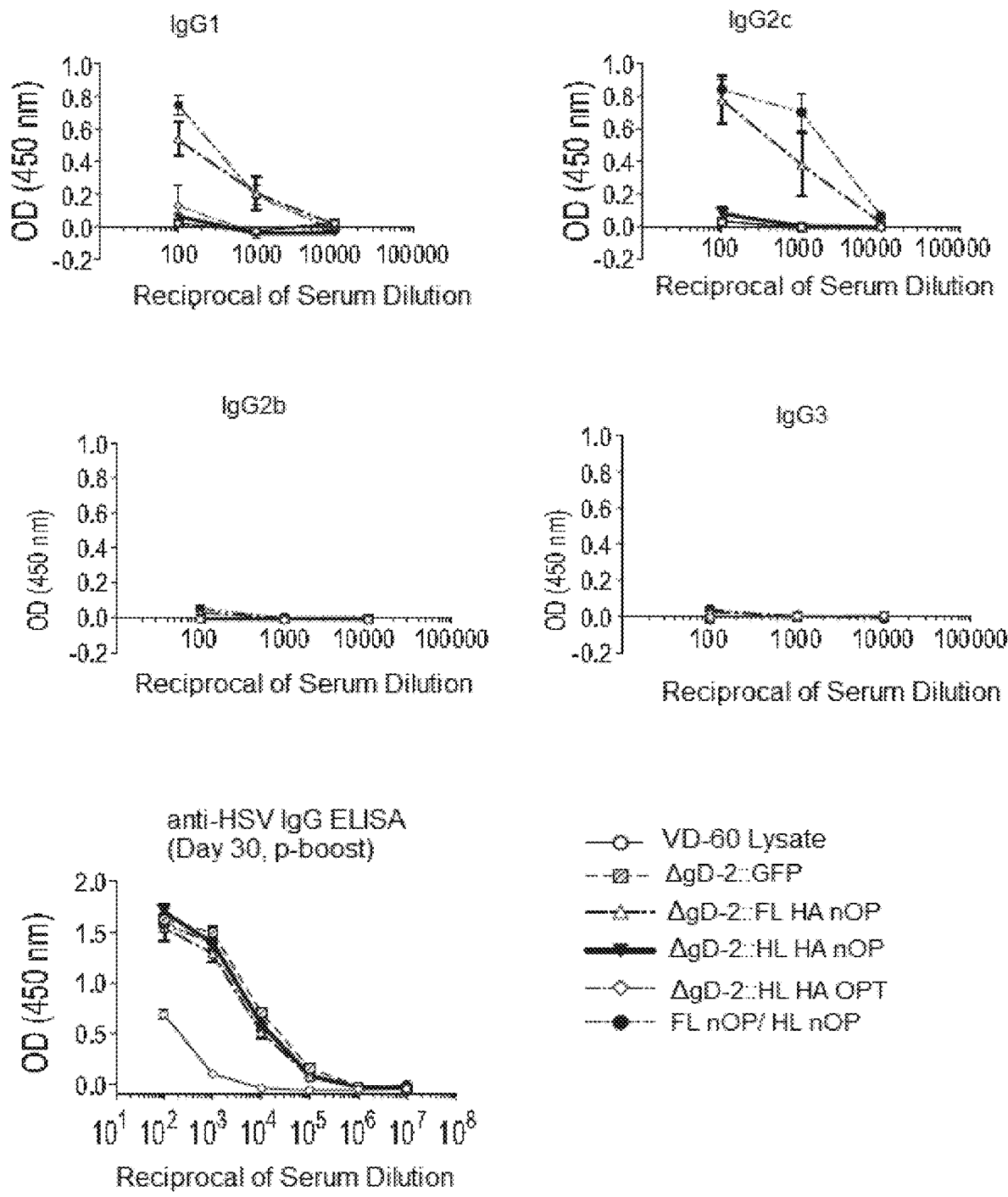
FIG. 20: Anti-PR8 IgG Isotype ELISA.

Anti-PR8 IgG Isotype ELISA. Mice were subcutaneously injected with ΔgD-2::RFP, ΔgD-2 expressing full-length PR8 hemagglutinin (FL nOP, (β3χ4), ΔgD-2 expressing headless PR8 hemagglutinin (HL nOP, β3χ5), or ΔgD-2 expressing headless PR8 hemagglutinin codon-optimized for HSV-2 (G) (HL OPT, β3χ6) or mock vaccinated with VD60 cell lysate. 5 mice/group were prime-boost vaccinated with each treatment separately. (See FIG. 20). 5 mice were primed with FL nOP and boosted with HL nOP. In each case, 5×106 PFU of virus were given with each injection. At day 30 (9 days post-boost), mice were bled and serum was collected. Enzyme-linked immunosorbent assays (ELISAs) were then run to check for antibodies against purified PR8 HA or Vero cells infected with HSV-2 4674. Mice prime-boosted with FL nOP or primed with FL nOP and boosted with HL nOP developed IgG1 and IgG2c antibodies against PR8 HA. No other group formed anti-PR8 IgG antibodies. All groups except the VD60 lysate group developed similar and high titers of anti-HSV IgGs. Anti-HSV IgGs anti-HSV IgGs were elicited with all the vaccine strains.

Example 4

Figures 21A, 21B, 21C:
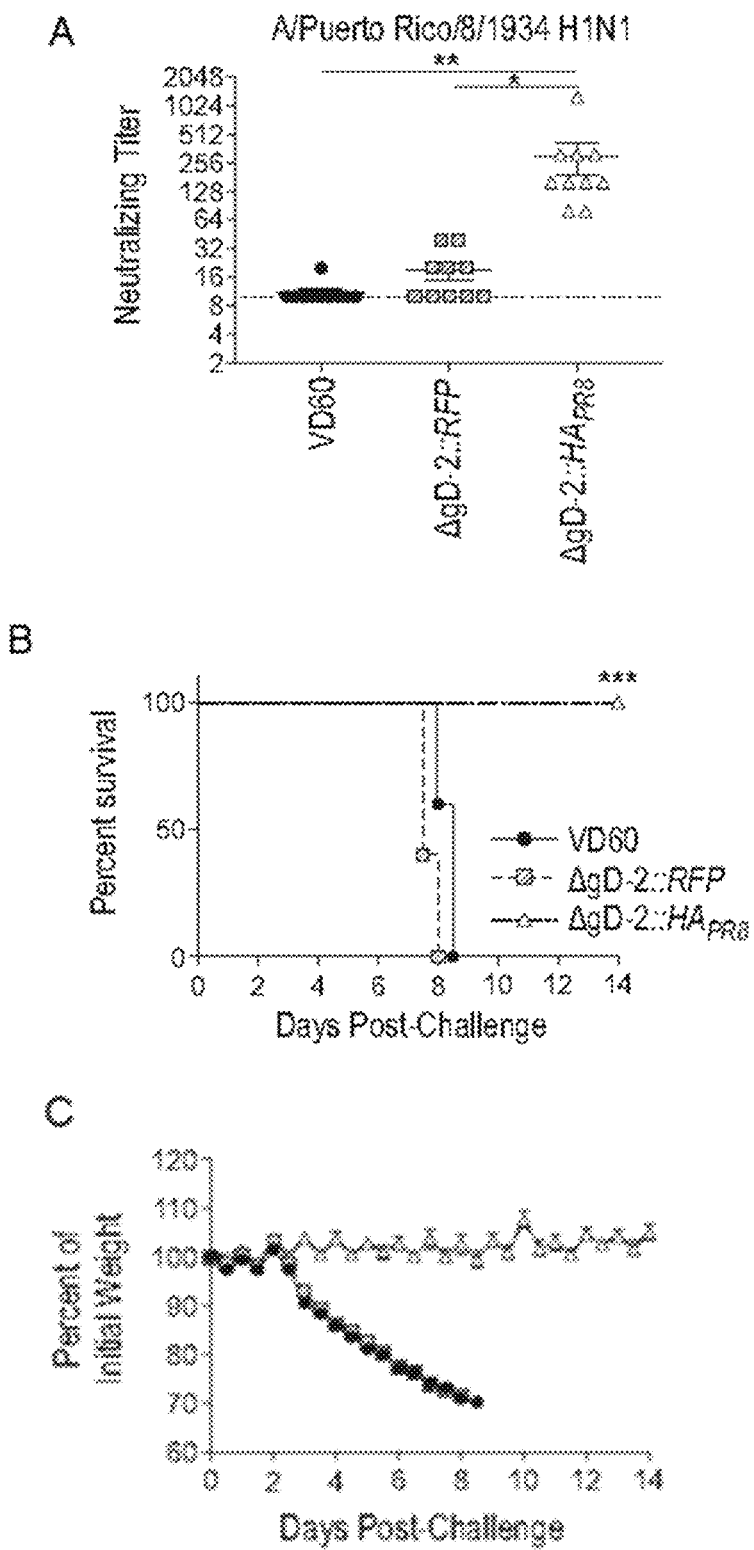
FIGS. 21A-21C: Mice vaccinated with ΔgD-2::FL HAPR8 (ΔgD-2::HAPR8) are fully protected from challenge with PR8. Mice were prime-boost vaccinated subcutaneously 3 weeks apart with 5×106 PFU of ΔgD-2::RFP or ΔgD-2::HAPR8 or mock vaccinated with VD60 cell lysate.

Mice vaccinated with ΔgD-2::HAPR8 are fully protected from challenge with PR8. Mice were prime-boost vaccinated subcutaneously 3 weeks apart with 5×106 PFU of ΔgD-2::RFP or ΔgD-2::HAPR8 or mock vaccinated with VD60 cell lysate. The mice were bled one-week post-boost and serum neutralization titer was measured against A/Puerto Rico/1934/8 IAV (PR8). (See FIG. 21A) Mice immunized with ΔgD-2::HAPR8 developed significant neutralizing Ab titers against PR8 (mean=304). Dotted line represents the limit of detection for the assay. Three weeks post-boost, mice were challenged intranasally with a 6×LD50 of the PR8 strain. The mice were sacrificed when they reached 75% of their initial weight. As shown in FIGS. 21B and 21C, mice immunized with ΔgD-2::HAPR8 were fully protected from PR8 challenge, while mice that received control vaccinations all succumbed to infection before day 9.

Figures 22A, 22B:
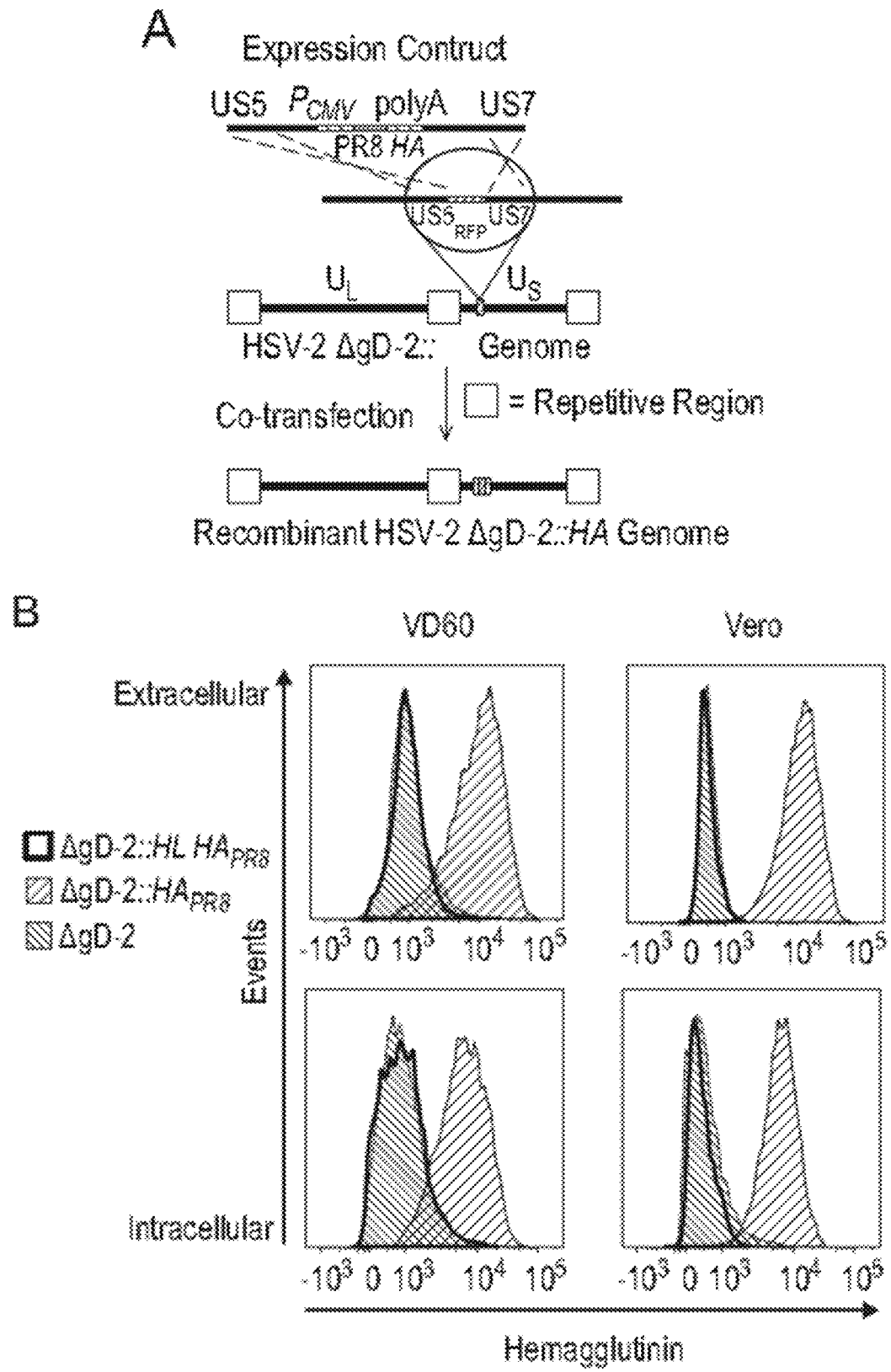
FIGS. 22A-22B show that recombinant gD-2::HAPR8 expresses high levels of PR8 protein.

Recombinant gD-2::HAPR8 expresses high levels of PR8 protein. To assess expression, ΔgD-2::RFP gDNA was co-transfected into VD60 cells alongside an HA expression cassette containing the hemagglutinin (HA) gene from IAV H1N1 strain A/Puerto Rico/1934/8 (PR8) downstream of PCMV and upstream of a poly-adenylation signal as illustrated in FIG. 22A. Extracellular and intracellular HA expression was measured by flow cytometry in Vero and VD60 cells infected with 3 MOI of ΔgD-2, ΔgD-2::HAPR8, or ΔgD-2 containing a truncated version of the PR8 HA expression cassette (ΔgD-2::HL HAPR8), and HA expression is shown in FIG. 22B.

Figures 23A, 23B, 23C, 23D, 23E, 23F:
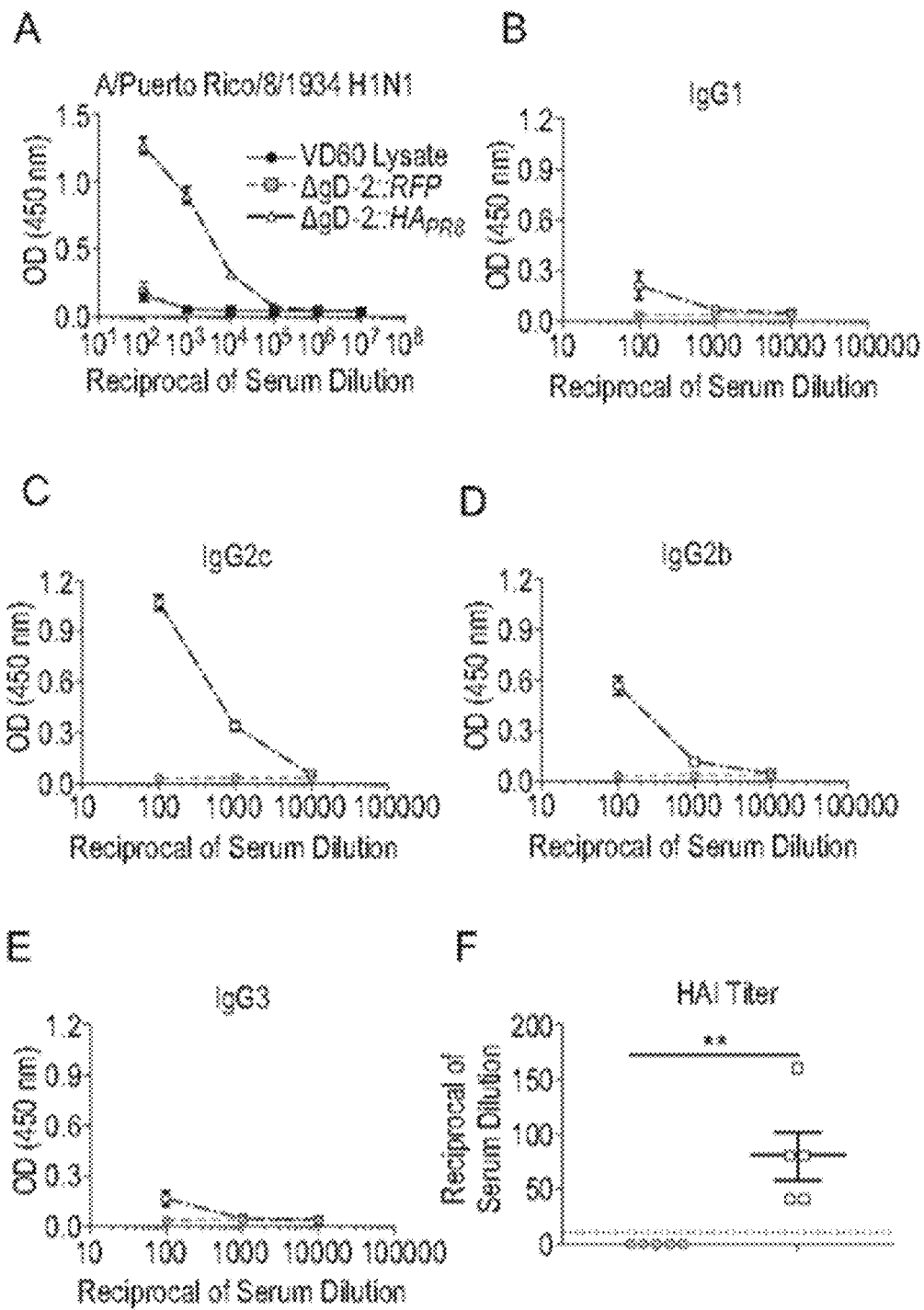
FIGS. 23A-23F show that mice immunized with ΔgD-2::HAPR8 develop high titers of functional and isotype switched anti-PR8 antibodies. Mice were prime-boost vaccinated 21 days apart with either VD60 cell lysate, ΔgD-2::RFP vector, or ΔgD-2::HAPR8. At day 28 post-prime, serum was collected for analysis. FIGS. A-E. Anti-PR8 antibodies were measured by ELISA against purified HA PR8 protein. Mice immunized with ΔgD::HAPR8 developed isotype switch anti-PR8 HA antibodies that were predominantly IgG2c and IgG2b.

Mice immunized with gD-2::HAPR8 develop high titers of functional and isotype switched anti-PR8 antibodies. Mice were prime-boost vaccinated 21 days apart with either VD60 cell lysate, ΔgD-2::RFP vector, or ΔgD-2::HAPR8 (5 mice per group). At day 28 post-prime vaccination, serum was collected for analysis. Anti-PR8 antibodies were measured by ELISA against purified HA PR8 protein. Mice immunized with ΔgD-2::HAPR8 developed isotype switch anti-PR8 HA antibodies that were predominantly IgG2c and IgG2b. (See FIGS. 23A-23E) Serum from mice immunized with ΔgD-2::HAPR8 induced significant hemagglutination inhibition compared to serum from mice immunized with ΔgD-2 (p<0.001; meanHAI titer=80). (See FIG. 23F) Mice immunized with ΔgD-2::RFP did not develop any hemagglutination inhibiting antibodies.

Figures 24A, 24B, 24C, 24D, 24E, 24F:
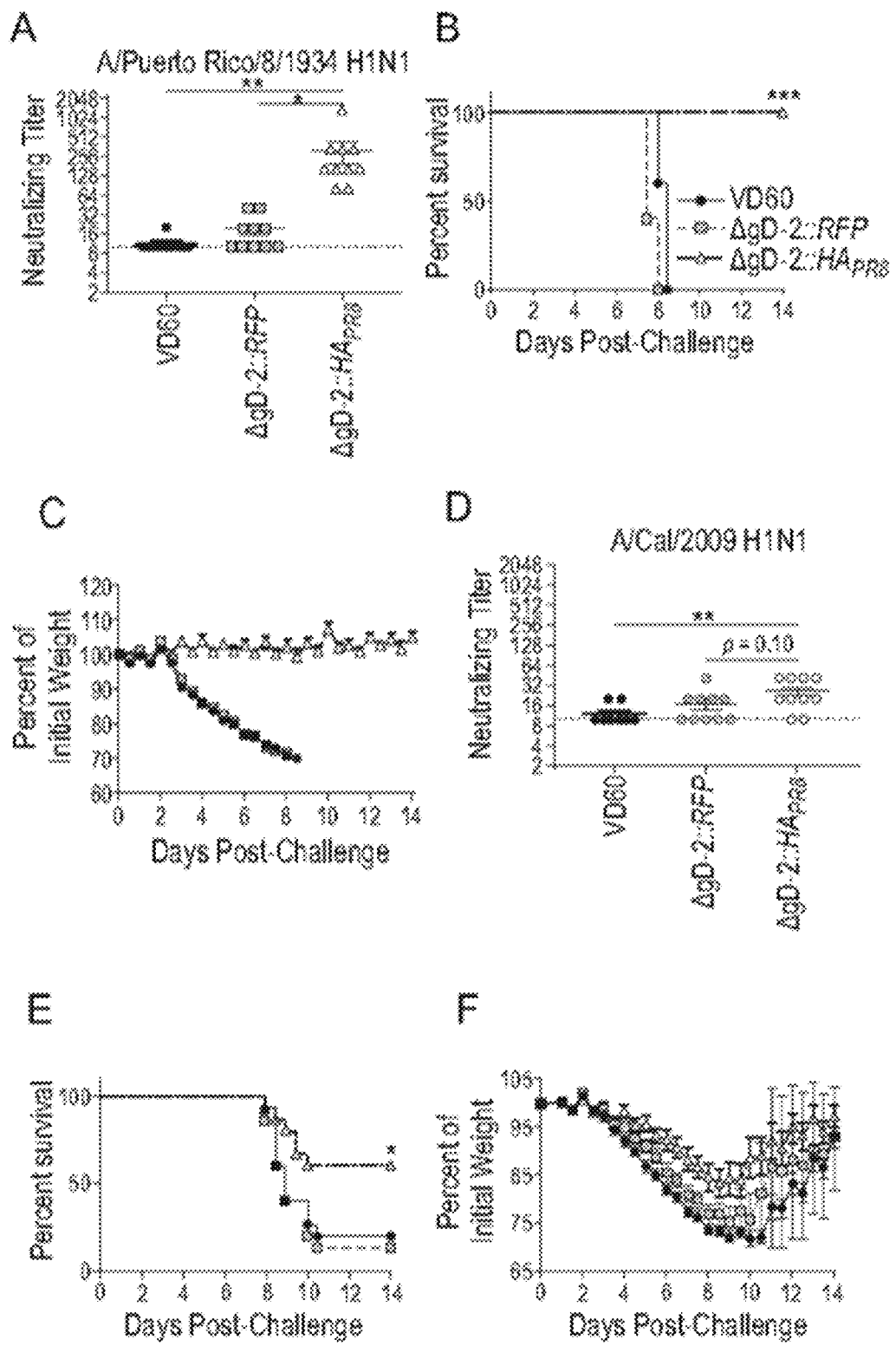

Mice immunized with gD-2::HAPR8 develop protection against IAV challenge. Mice were prime-boost immunized 21 days apart with VD60 cell lysate, ΔgD-2, or ΔgD-2::HAPR8, bled at day 28 post-prime, and challenged intranasally 14 days later with a 6× LD50 of IAV. Mice were sacrificed after reaching 70% of starting weight and neutralization titers were measured using microneutralization assays against the respective strains. As shown in FIGS. 24A-24C, mice immunized with ΔgD-2::HAPR8 developed significant neutralizing titers against PR8 (mean titerPR8=1: 304; pVD60<0.01; pΔgD-2<0.05; n=10 mice/group). Mice immunized with ΔgD-2::HAPR8 were also fully protected from weight loss and mortality followed by challenge with PR8 (p<0.001, n=5 mice/group). As shown in FIGS. 24D-

24F, mice immunized with ΔgD-2::HAPR8 developed significant neutralizing antibodies against A/California/2009 H1N1 (A/Cal/2009) IAV (mean titer A/Cal=26; pVD60<0.01 pΔgD-2=0.1; n=10 mice/group). Mice immunized with ΔgD::HAPR8 were partially protected from weight loss and mortality following challenge with A/Cal/2009 (p<0.05, n=15 mice/group). As shown in FIGS. 24G-24I, mice immunized with ΔgD-2::HAPR8, ΔgD-2::RFP, or VD60 cell lysate did not develop neutralizing antibody titers against A/Victoria/3/75 H3N2 (A/Vic), and A/Aichi/68 H3N2 (X-31) and were not protected from weight loss and mortality following challenge (nneutralization=10 mice/group; nA/Vic challenge=15 mice/group; nX-31 challenge=5 mice/group).

Figures 25A, 25B, 25C, 25D, 25E, 25F:
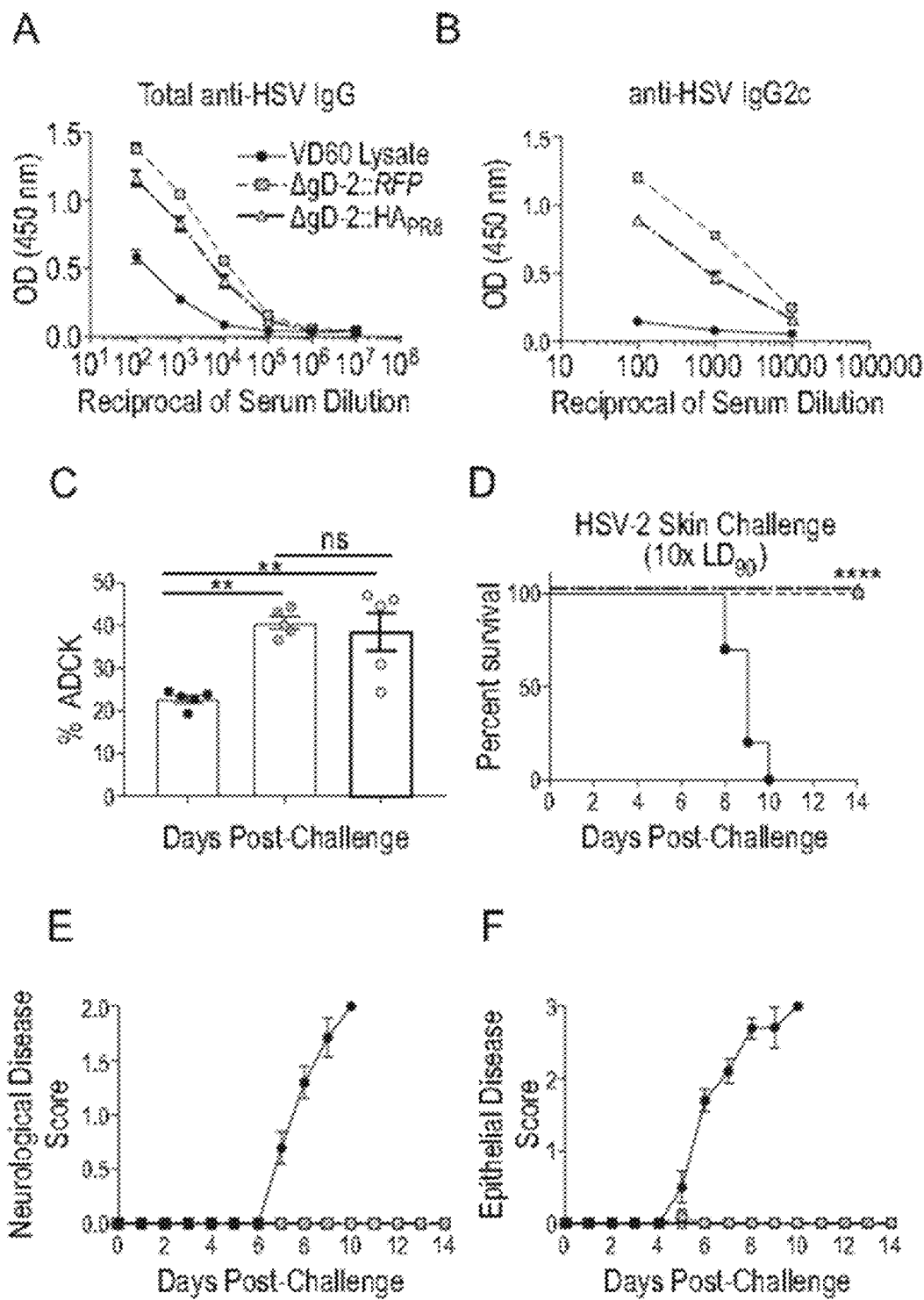
FIGS. 25A-25F. Mice immunized with ΔgD-2::HAPR8 develop fully protective ADCC immunity against HSV-2. Mice were prime-boost vaccinated 21 days apart with either VD60 cell lysate, ΔgD-2, or ΔgD-2::HAPR8.
Figure 26:
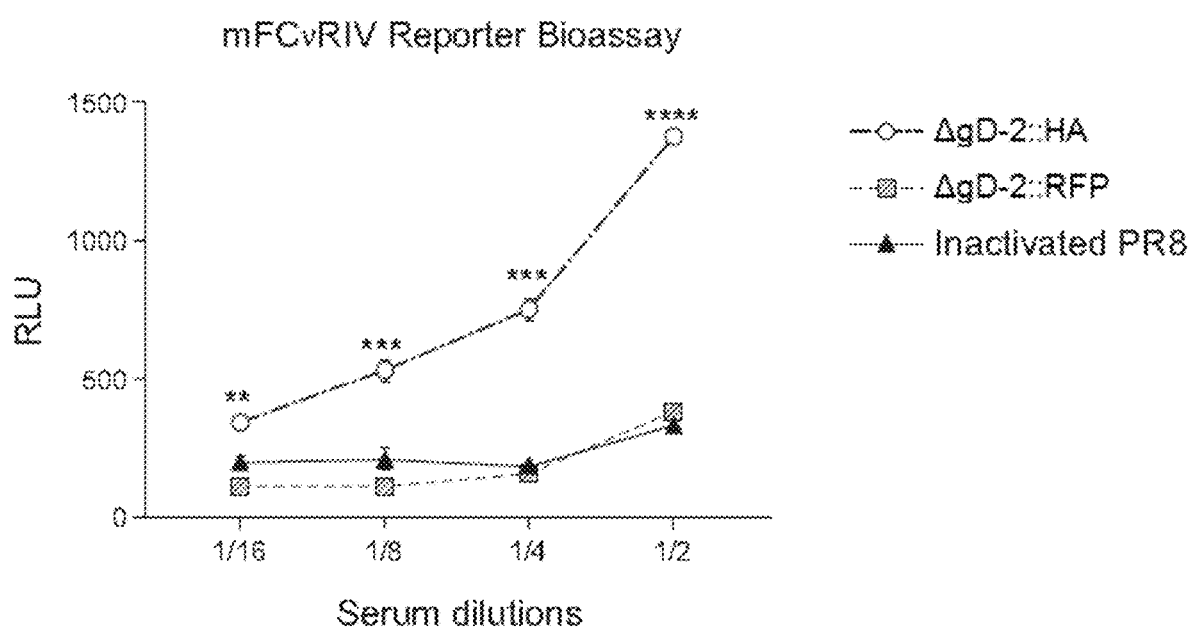
FIG. 26 shows the results of mFcγRIV ADCC reporter bioassay response to serially diluted serum samples collected from mice vaccinated with HSV-2 ΔgD::HA, HSV-2 ΔgD::RFP and inactivated A/Puerto Rico/8/1934 H1N1 virus (PR8). Madin-Darby Canine Kidney (MDCK) cells infected with PR8 virus were used as target cells and mFcγRIV expressing Jurkat T cells were used as effector cells. The target cells were incubated with serially diluted serum samples and effector cells. Bio-Glo™ Reagent was added, and luminescence was measured. The recombinant HSV-2 ΔgD-2::HA vaccinated mice showed significantly higher activation of mFcγRIV receptors in comparison to mice vaccinated with HSV-2 ΔgD-2::RFP and inactivated PR8 virus. The p value for significance is <0.05. Symbols: P<0.01, *P<0.001, ****P<0.0001.

Mice immunized with ΔgD-2::HAPR8 develop fully protective ADCC immunity against HSV-2. Mice were prime-boost vaccinated 21 days apart with either VD60 cell lysate, ΔgD-2, or ΔgD-2::HAPR8 (5 mice per group). In FIGS. 25A and 25B, the mice were bled 1-week post-boost and the serum was analyzed by ELISA. Mice that received ΔgD-2 or ΔgD-2::HAPR8 generated similarly high levels of HSV-specific IgG (FIG. 25A). Additionally, these IgGs were predominantly IgG2c. In FIG. 25C, rapid fluorometric antibody-dependent cell-mediated killing (RFADCK) assay was carried out using the same serum as FIGS. 25A and 25B. Sera from mice vaccinated with ΔgD-2 or ΔgD-2::HAPR8 elicited significant ADCK activity in the presence of J774.1 macrophages and ΔgD-2 infected cells compared with serum from mice given VD60 cell lysate (p<0.01). There was no difference between the ADCK activity elicited by sera from mice vaccinated with ΔgD-2 and ΔgD-2::HAPR8. At 21 days post-boost, mice were challenged by skin scarification with a 10× LD90 of HSV-2 4674. Mice that received VD60 cell lysate succumbed to HSV-2 by 10 and developed significant epithelial and neurological disease. Mice that received ΔgD-2 and ΔgD-2::HAPR8 were fully protected from morbidity and mortality following challenge. (See FIGS. 25D to 25F)

mFcγRIV ADCC reporter bioassay response. Serum samples collected from mice vaccinated with ΔgD-2::HA, ΔgD-2::RFP, and inactivated A/Puerto Rico/8/1934 H1N1 virus (PR8) were serially diluted and subjected to mFcγRIV ADCC reporter bioassay. Madin-Darby Canine Kidney (MDCK) cells infected with PR8 virus were used as target cells and mFcγRIV expressing Jurkat T cells were used as effector cells. The target cells were incubated with the serially diluted serum samples and effector cells. Bio-Glo™ Reagent was added, and luminescence was measured. The HSV-2 ΔgD::HA vaccinated mice showed significantly higher activation of mFcγRIV receptors at each dilution tested in comparison to mice vaccinated with ΔgD-2::RFP and inactivated PR8 virus. (See FIG. 26)

Example 5

Figure 27:
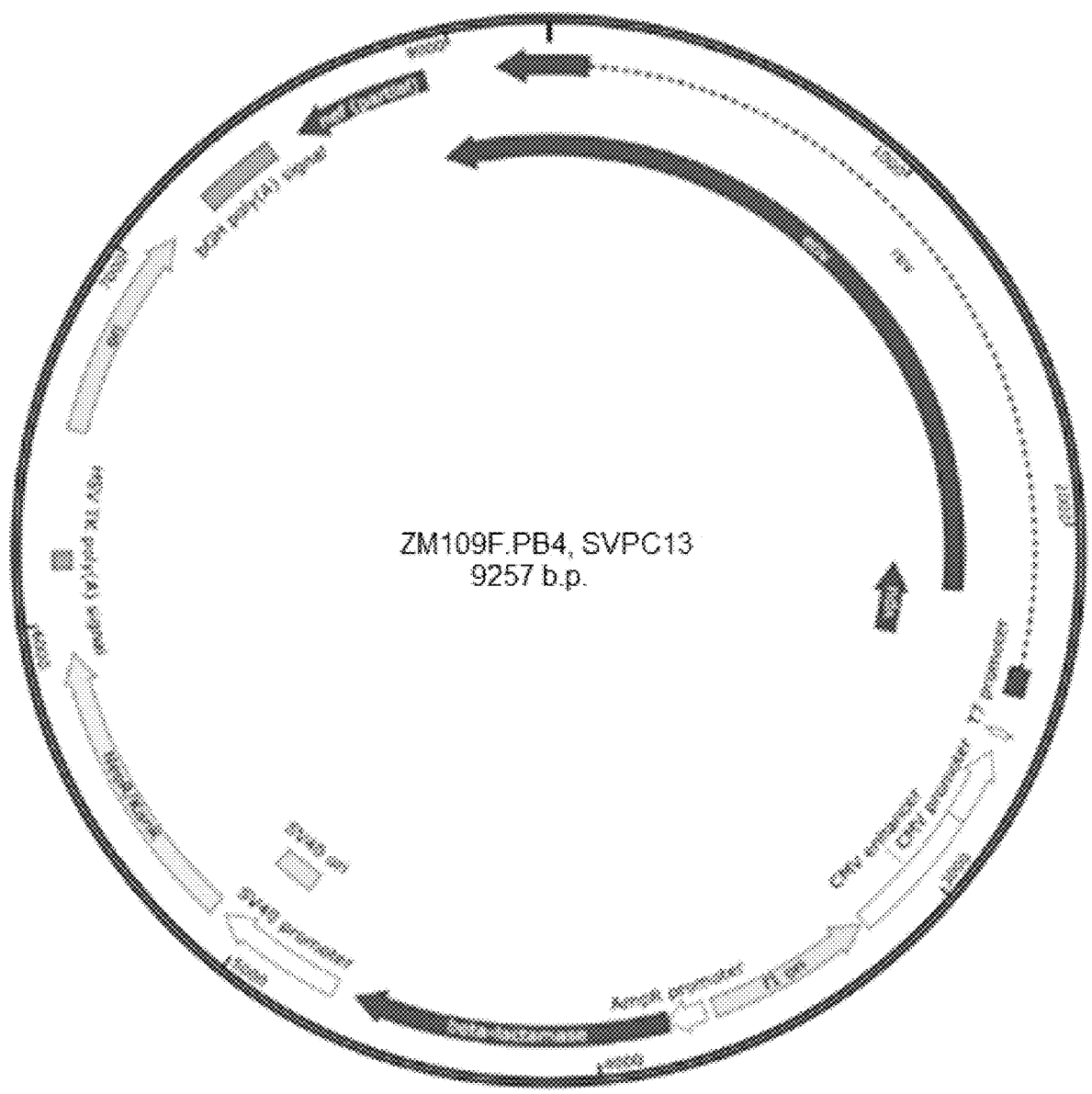
FIG. 27 is a map of the plasmid ZM109F.PB4, which was used to amplify full length HIV-1 Env (Clade C) and Rev, together with partial Nef of HIV-1.

Cloning of HIV-1 Env in pBkk412 plasmid containing HSV-2 genes. The full length HIV-1 Env (Clade C) and Rev genes, together with partial Nef gene, were PCR amplified from the plasmid ZM109F.PB4 (FIG. 27) obtained from NIH AIDS Reagent Program.

Figure 28:
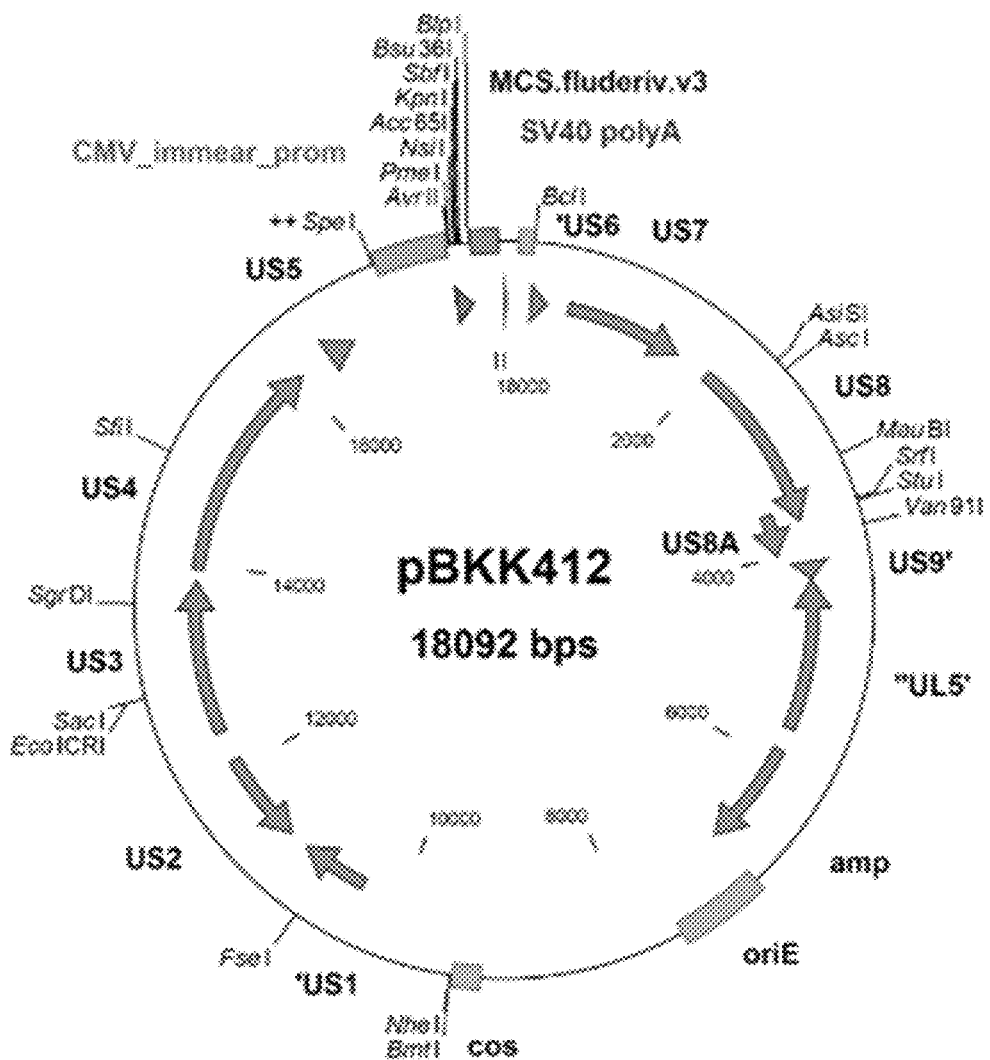
FIG. 28 is a map of the pBkk412 plasmid.

The PCR fragment product, which also contained bGH polyA signal and T7 promoter, was cloned into the multiple cloning site (MCS) of the pBkk412 plasmid under control of CMV promoter, using RE sbf I and blp I. (See FIG. 28)

Figure 29A:
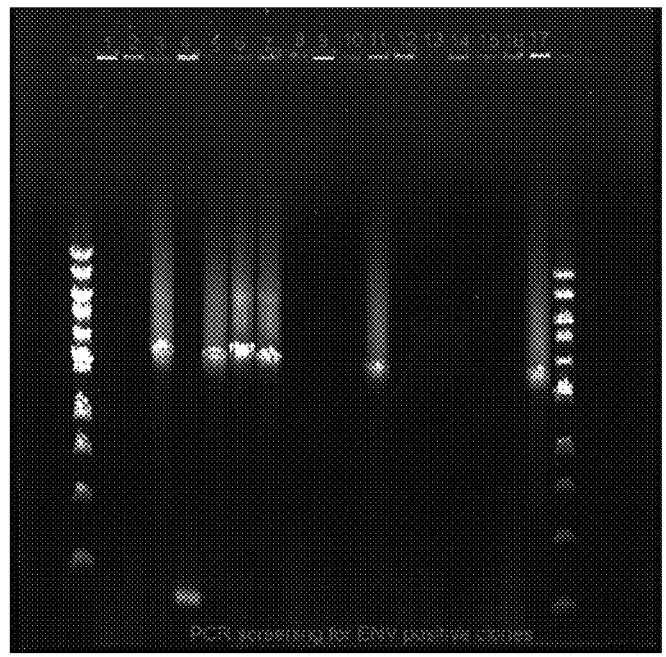
FIG. 29A. Screen of transformed E.coli colonies for the presence of the cloned insert.
Figure 29B:
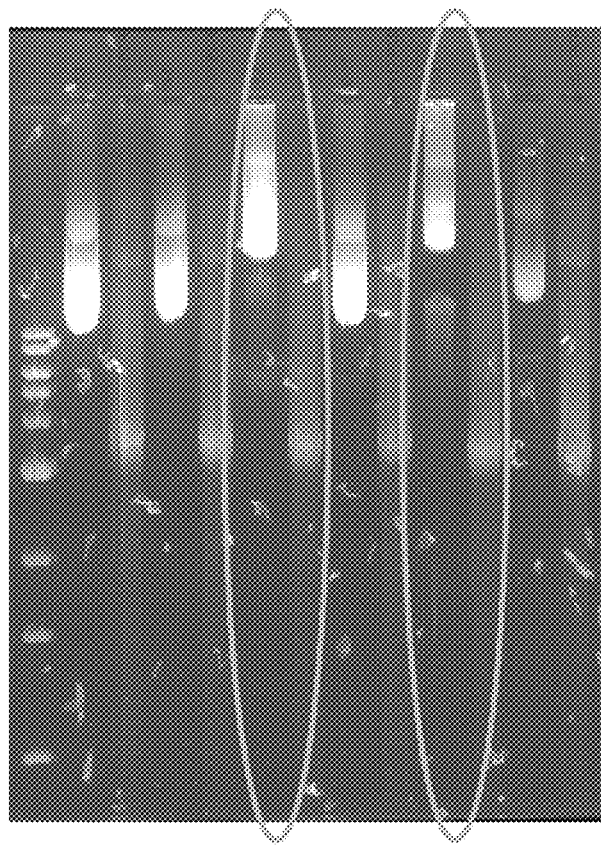
FIG. 29B. Analysis by PCR to identify clones having the correct nucleic acid size.

Stable, competent *E.coli* cells were transformed and plated on Agar+ carbenicillin. Colonies were screened for the presence of the insert using PCR (FIG. 29A), and were used to prepare DNA for analysis. The DNA was amplified by PCR and clones (CL 15-6 and CL 26-11) having the correct size were selected for transient transfection to assess HIV-1 protein expression. (FIG. 29B)

Once expression of the HIV proteins in transfected cells is confirmed, cells will be co-transfected with the linear recombinant plasmid and the HSV ΔgD-2 negative virus (e.g., ΔgD-2::RFP, ΔgD-2::GFP) and selected for recombinants that express the HIV protein and do not express the GFP or RFP marker. Expression of the HIV protein(s) by the new recombinant virus will be assessed by Western blot or flow cytometry (FACS). Mice will be immunized intramuscularly (prime and boost) and serum collected and screen for the presence of HIV-specific antibodies. The functionality (e.g., neutralizing and non-neutralizing functions) of the Abs will also be measured. A humanized mouse model which renders mice susceptible to infection with HIV, will also be used to assess whether the vaccine protects the mice from HIV infection.

Set forth below are some embodiments of the process, the recombinant virus, and the methods disclosed herein.

Embodiment 1: A process for producing a vaccine vector directed against a heterologous antigen, the process comprising: a) providing an HSV-2 genome comprising: (i) a fully or partially deleted in a gene encoding HSV-2 glycoprotein D, and (ii) a nucleic acid comprising a promoter-FP construct, wherein FP is a nucleic acid encoding a fluorescent protein; b) co-transfecting a host cell with (i) the HSV-2 genome of a) and (ii) a linear DNA fragment encoding the heterologous antigen under conditions whereby allelic recombination occurs between the HSV-2 genome and the DNA fragment; c) screening plaques resulting from b) to identify plaques not showing fluorescence under excitation light which elicits fluorescent protein fluorescence; d) recovering from those plaques not showing fluorescence in c) recombinant HSV-2 viruses or virions so as to obtain a vaccine vector directed against the heterologous antigen.

Embodiment 2: The process of embodiment 1, wherein the host cell is a HSV-1 glycoprotein D complementing cell.

Embodiment 3: The process of embodiment 1 or embodiment 2, wherein the promoter of the promoter-FP construct is a heterologous promoter.

Embodiment 4: The process of any of Embodiments 1-3, wherein the co-transfecting is effected by electroporation.

Embodiment 5: The process of any of Embodiments 1-4, wherein the fluorescent protein is Red Fluorescent Protein (RFP).

Embodiment 6: The process of any of Embodiments 1-5, wherein the host cell is co-transfected with (i) the HSV-2 genome of a) and (ii) a linear DNA fragment encoding, in order, (i) HSV-2 gD signal sequence, the heterologous antigen, HSV-2 gD transmembrane domain, HSV-2 gD cytosolic domain, but not encoding a HSV-2 gD extracellular domain, or (ii) HSV-2 gD signal sequence, the heterologous antigen, and cytosolic domain of HSV-2 gD.

Embodiment 7: The process of any of Embodiments 1-5, wherein the host cell is co-transfected with (i) the HSV-2 genome of a) and (ii) a linear DNA fragment encoding, in order, (i) a promoter, the heterologous antigen, and optionally a poly-A signal.

Embodiment 8: The process of any of Embodiments 1-7, wherein the heterologous antigen is an influenza antigen.

Embodiment 9: The process of any of Embodiments 1-8, wherein the heterologous antigen is an influenza hemagglutinin (HA) antigen.

Embodiment 10: The process of Embodiment 9, wherein the HA antigen is a full-length HA extracellular domain or is a HA stalk.

Embodiment 11: The process of any of Embodiments 1-7, wherein the heterologous antigen is an HIV antigen.

Embodiment 12: The process of Embodiment 11, wherein the HIV antigen is an Env gp145.

Embodiment 13: The process of any of Embodiments 1-12, wherein the heterologous antigen is under control of an upstream CMV promoter and has a downstream SV40 poly-A signal.

Embodiment 14: The process of any of Embodiments 1-13, wherein the promoter is a promoter of Elongation Factor 1 □ gene (PEF1α) and wherein PEF1α and FP are fused together (PEF1α-FP).

Embodiment 15: A vaccine vector, or a recombinant herpes simplex virus-2 (HSV-2) comprising a genome encoding a heterologous antigen, made by the process of any of Embodiments 1-14.

Embodiment 16: A recombinant herpes simplex virus-2 (HSV-2) comprising: (i) a complete deletion of an HSV-2 glycoprotein D-encoding gene in the genome thereof; and (ii) (a) a linear DNA fragment, encoding a promoter, a heterologous antigen signal sequence, and a heterologous antigen or (b) encoding a promoter, and a heterologous antigen.

Embodiment 17: A recombinant herpes simplex virus-2 (HSV-2) comprising: (i) a partial deletion of an HSV-2 glycoprotein D-encoding gene in the genome thereof; and (ii) (a) a linear DNA fragment encoding, in order, an HSV-2 gD signal sequence, a heterologous antigen, an HSV-2 gD transmembrane domain, optionally an HSV-2 gD cytosolic domain, but not encoding an HSV-2 gD extracellular domain, or (b) a linear DNA fragment encoding, in order, an HSV-2 gD signal sequence, a heterologous antigen, and transmembrane cytoplasmic tail of HSV-2 gD.

Embodiment 18: The recombinant HSV-2 of Embodiment 16 or 17, further comprising a parasitic surface glycoprotein on a lipid bilayer thereof, wherein the parasite is a parasite of a mammal.

Embodiment 19: The recombinant HSV-2 of any of Embodiments 16-18, wherein the HSV-2 glycoprotein D-encoding gene is an HSV-2 US6 gene.

Embodiment 20: The recombinant HSV-2 of any of Embodiments 16-19, wherein the heterologous antigen is an influenza antigen.

Embodiment 21: The recombinant HSV-2 of any of Embodiments 16-20, wherein the heterologous antigen is hemagglutinin (HA) antigen.

Embodiment 22: The recombinant HSV-2 of Embodiment 21, wherein the HA antigen is a full-length HA extracellular domain or is a HA stalk.

Embodiment 23: The recombinant HSV-2 of any of Embodiments 16-19, wherein the heterologous antigen is an HIV antigen.

Embodiment 24: The recombinant HSV-2 of Embodiment 23, wherein the HIV antigen is an Env gp145.

Embodiment 25: A cell comprising therein a recombinant virus of any of Embodiments 16-24, wherein the cell is not present in a human being.

Embodiment 26: A vaccine composition comprising the recombinant virus of any of Embodiments 16-24.

Embodiment 27: A pharmaceutical composition comprising the virus of any of Embodiments 16-24, and a pharmaceutically acceptable carrier.

Embodiment 28: A method of eliciting and/or enhancing an immune response in a subject, the method comprising administering to the subject an amount of the recombinant virus of any of Embodiments 16-24, in an amount effective to elicit and/or enhance an immune response in a subject.

Embodiment 29: A method of eliciting and/or enhancing an immune response in a subject, the method comprising administering to the subject an amount of the vaccine of Embodiment 26 in an amount effective to elicit and/or enhance an immune response in a subject.

Embodiment 30: A method of eliciting and/or enhancing an immune response in a subject, the method comprising administering to the subject an amount of the pharmaceutical composition of Embodiment 27, in an amount effective to elicit and/or enhance an immune response in a subject.

Embodiment 31: A method of treating or reducing the likelihood of an influenza infection in a subject, the method comprising administering to the subject an amount of the recombinant virus of any of Embodiments 16-22, in an amount effective to treat or reduce the likelihood of an influenza infection in a subject.

Embodiment 32: A method of treating or reducing the likelihood of an influenza infection in a subject, the method comprising administering to the subject an amount of the vaccine of Embodiment 26, in an amount effective to treat or reduce the likelihood of an influenza infection in a subject.

Embodiment 33: A method of treating or reducing the likelihood of an influenza infection in a subject, the method comprising administering to the subject an amount of the pharmaceutical composition of Embodiment 27, in an amount effective to treat or reduce the likelihood of an influenza infection in a subject.

Embodiment 34: A method of treating or reducing the likelihood of an HIV infection in a subject, the method comprising administering to the subject an amount of the recombinant virus of any of Embodiments 16-19, 23 or 24, in an amount effective to treat or reduce the likelihood of an HIV infection in a subject.

Embodiment 35: A method of treating or reducing the likelihood of an HIV infection in a subject, the method comprising administering to the subject an amount of the vaccine of Embodiment 26, in an amount effective to treat or reduce the likelihood of an HIV infection in a subject.

Embodiment 36: A method of treating or reducing the likelihood of an HIV infection in a subject, the method comprising administering to the subject an amount of the pharmaceutical composition of Embodiment 27, in an amount effective to treat or reduce the likelihood of an HIV infection in a subject.

Embodiment 37: A method of vaccinating a subject for influenza infection, the method comprising administering to the subject an amount of the recombinant virus of any of Embodiments 16-22, in an amount effective to vaccinate a subject for influenza infection.

Embodiment 38: A method of vaccinating a subject for influenza infection, the method comprising administering to the subject an amount of the vaccine of Embodiment 26, in an amount effective to vaccinate a subject for influenza infection.

Embodiment 39: A method of vaccinating a subject for influenza infection, the method comprising administering to the subject an amount of the pharmaceutical composition of Embodiment 27, in an amount effective to vaccinate a subject for influenza infection.

Embodiment 40: A method of vaccinating a subject for HIV infection, the method comprising administering to the subject an amount of the recombinant virus of any of Embodiments 16-19, 23 or 24, in an amount effective to vaccinate a subject for HIV infection.

Embodiment 41: A method of vaccinating a subject for HIV infection, the method comprising administering to the subject an amount of the vaccine of Embodiment 26, in an amount effective to vaccinate a subject for HIV infection.

Embodiment 42: A method of vaccinating a subject for HIV infection, the method comprising administering to the subject an amount of the pharmaceutical composition of Embodiment 27, in an amount effective to vaccinate a subject for HIV infection.

Embodiment 43: A method of eliciting and/or enhancing an immune response in a subject, the method comprising administering to the subject an amount of a recombinant herpes simplex virus-2 (HSV-2) made by the process of any of Embodiments 1-14 and comprising (i) a complete deletion of an HSV-2 glycoprotein D-encoding gene in the genome thereof and (ii) encoding a promoter, an influenza hemagglutinin (HA) antigen signal sequence, and an HA antigen in an amount effective to elicit and/or enhance an immune response in a subject.

Embodiment 44: A method of treating or reducing the likelihood of an influenza infection in a subject, the method comprising administering to the subject an amount of a recombinant herpes simplex virus-2 (HSV-2) made by the process of any of Embodiments 1-13 and comprising (i) a complete deletion of an HSV-2 glycoprotein D-encoding gene in the genome thereof and (ii) encoding a promoter, an influenza hemagglutinin (HA) antigen signal sequence, and an HA antigen in an amount effective to treat or reduce the likelihood of an influenza infection in a subject.

Embodiment 45: A method of vaccinating a subject for influenza infection, the method comprising administering to the subject an amount of a recombinant herpes simplex virus-2 made by the process of any of Embodiments 1-14 and comprising (i) a complete deletion of an HSV-2 glycoprotein D-encoding gene in the genome thereof and (ii) encoding a promoter, an influenza hemagglutinin (HA) antigen signal sequence, and an HA antigen in an amount effective to vaccinate a subject for influenza infection.

Embodiment 46: The method of any of Embodiments 43-45, wherein the HA antigen is a full-length HA extracellular domain.

Embodiment 47: The method of Embodiment 46, further comprising, subsequent to an initial administration of the recombinant herpes simplex virus-2 encoding a full-length HA extracellular domain, administering one or more amounts of a recombinant herpes simplex virus-2 comprising (i) a complete deletion of an HSV-2 glycoprotein D-encoding gene in the genome thereof and (ii) encoding a promoter, a HA antigen signal sequence, and an HA stalk, but not encoding a full-length HA.

Embodiment 48: The method of any of Embodiments 28-47, wherein the subject is a human being.

Embodiment 49: A method of quantitating a rate or amount of antibody-dependent cell-mediated killing (ADCK) in a population of cells, the method comprising: infecting a plurality of cells of the population of cells with a fluorescent protein-expressing recombinant HSV-2 that comprises a genome deleted for the gene encoding HSV-2 gD, under conditions permitting expression of the fluorescent protein in the cells, contacting the plurality of infected cells with an antibody-containing solution and a population of immune cells, and quantitating at one or more time points the amount of the plurality of infected cells exhibiting fluorescent protein fluorescence and, optionally, one or more markers, so as to quantitate over time the amount of live infected cells, so as to thereby quantitating the rate or amount of ADCK in the population of cells.

Embodiment 50: The method of Embodiment 49, wherein the method is performed in vitro.

Embodiment 51: The method of Embodiment 49 or 50, wherein the population of immune cells comprises macrophages.

Embodiment 52: The method of any of Embodiments 49-51, wherein the antibody-containing solution comprises serum.

Embodiment 53: The method of any of Embodiments 49-51, wherein the fluorescent protein is Red Fluorescent Protein.

Embodiment 54: The method of any of Embodiments 49-53, wherein the amount of the plurality of infected cells exhibiting fluorescent protein fluorescence and, optionally, one or more markers, is measured by fluorescence-activated cell sorting (FACS).

Embodiment 55: The method of any of Embodiments 49-55, wherein the at least one marker comprises a cell membrane marker, a live/dead marker, or a combination thereof.

Embodiment 56: The method of any of Embodiments 49-55, further comprising quantitating at one or more time points the amount of cells exhibiting fluorescent protein fluorescence and, optionally, one or more markers, in a control population of infected cells otherwise identical but not contacted with an antibody-containing solution and comparing the amount or rate quantitated to the amount or rate quantitated for the population of cells contacted with the antibody-containing solution.

Embodiment 57: The method of any of Embodiments 49-56, wherein the population of immune cells is present at effector:target ratio of 5:1 or greater.

Embodiment 58: The method of any of Embodiments 49-57, wherein the recombinant HSV-2 is made by the process of any of Embodiments 1-14.

Throughout this application various publications are referred to. Full citations for these references may be found at the end of the specification. The disclosures of these publications, and all patents, patent application publications and books referred to herein, are hereby incorporated by reference in their entirety into the subject application to more fully describe the art to which the subject invention pertains.

One skilled in the art will readily appreciate that the specific methods and results discussed hereinabove are merely illustrative of the invention as described more fully in the claims that follow thereafter.

REFERENCES

Bouvier, N. M. and A. C. Lowen (2010). "Animal Models for Influenza Virus Pathogenesis and Transmission." Viruses 2(8): 1530-1563.

Cheshenko, N., J. B. Trepanier, M. Stefanidou, N. Buckley, P. Gonzalez, W. Jacobs and B. C. Herold (2013). "HSV activates Akt to trigger calcium release and promote viral entry: novel candidate target for treatment and suppression." FASEB J 27(7): 2584-2599.

Eisenberg, R. J., D. Long, R. Hogue-Angeletti and G. H. Cohen (1984). "Amino-terminal sequence of glycoprotein D of herpes simplex virus types 1 and 2." J Virol 49(1): 265-268.

Gibson, D. G., L. Young, R. Y. Chuang, J. C. Venter, C. A. Hutchison, 3rd and H. O. Smith (2009). "Enzymatic assembly of DNA molecules up to several hundred kilobases." Nat Methods 6(5): 343-345.

Haynes, B. F., P. B. Gilbert, M. J. McElrath, S. Zolla-Pazner, G. D. Tomaras, S. M. Alam, D. T. Evans, D. C. Montefiori, C. Karnasuta, R. Sutthent, H. X. Liao, A. L. DeVico, G. K. Lewis, C. Williams, A. Pinter, Y. Fong, H. Janes, A. DeCamp, Y. Huang, M. Rao, E. Billings, N. Karasavvas, M. L. Robb, V. Ngauy, M. S. de Souza, R. Paris, G. Ferrari, R. T. Bailer, K. A. Soderberg, C. Andrews, P. W. Berman, N. Frahm, S. C. De Rosa, M. D. Alpert, N. L. Yates, X. Shen, R. A. Koup, P. Pitisuttithum, J. Kaewkungwal, S. Nitayaphan, S. Rerks-Ngarm, N. L. Michael and J. H. Kim (2012) "Immune-correlates analysis of an HIV-1 vaccine efficacy trial." N Engl J Med 366(14): 1275-1286.

He, W., G. S. Tan, C. E. Mullarkey, A. J. Lee, M. M. Lam, F. Krammer, C. Henry, P. C. Wilson, A. A. Ashkar, P. Palese and M. S. Miller (2016). "Epitope specificity plays a critical role in regulating antibody-dependent cell-mediated cytotoxicity against influenza A virus." Proc Natl Acad Sci USA 113(42): 11931-11936.

Jegaskanda S., P. C. R., and Stephen J. Kent (2014). "Influenza-Specific Antibody-Dependent Cellular Cytotoxicity: Toward a Universal Influenza Vaccine." The Journal of Immunology.

Liao, H. X., R. Lynch, T. Zhou, F. Gao, S. M. Alam, S. D. Boyd, A. Z. Fire, K. M. Roskin, C. A. Schramm, Z. Zhang, J. Zhu, L. Shapiro, N. C. S. Program, J. C. Mullikin, S. Gnanakaran, P. Hraber, K. Wiehe, G. Kelsoe, G. Yang, S. M. Xia, D. C. Montefiori, R. Parks, K. E. Lloyd, R. M. Scearce, K. A. Soderberg, M. Cohen, G. Kamanga, M. K. Louder, L. M. Tran, Y. Chen, F. Cai, S. Chen, S. Moquin, X. Du, M. G. Joyce, S. Srivatsan, B. Zhang, A. Zheng, G. M. Shaw, B. H. Hahn, T. B. Kepler, B. T. Korber, P. D. Kwong, J. R. Mascola and B. F. Haynes (2013). "Co-evolution of a broadly neutralizing HIV-1 antibody and founder virus." Nature 496(7446): 469-476.

Mullarkey, C. E., M. J. Bailey, D. A. Golubeva, G. S. Tan, R. Nachbagauer, W. He, K. E. Novakowski, D. M. Bowdish, M. S. Miller and P. Palese (2016). "Broadly Neutralizing Hemagglutinin Stalk-Specific Antibodies Induce Potent Phagocytosis of Immune Complexes by Neutrophils in an Fc-Dependent Manner" MBio 7(5).

Nicola, A. V., S. H. Willis, N. N. Naidoo, R. J. Eisenberg and G. H. Cohen (1996). "Structure-function analysis of soluble forms of herpes simplex virus glycoprotein D." J Virol 70(6): 3815-3822.

Osterholm, M. T., N. S. Kelley, A. Sommer and E. A. Belongia (2012). "Efficacy and effectiveness of influenza vaccines: a systematic review and meta-analysis." Lancet Infect Dis 12(1): 36-44.

Petro, C., P. A. Gonzalez, N. Cheshenko, T. Jandl, N. Khajoueinejad, A. Benard, M. Sengupta, B. C. Herold and W. R. Jacobs (2015). "Herpes simplex type 2 virus deleted in glycoprotein D protects against vaginal, skin and neural disease." Elife 4.

Petro, C. D., B. Weinrick, N. Khajoueinejad, C. Burn, R. Sellers, W. R. Jacobs, Jr. and B. C. Herold (2016). "HSV-2 DeltagD elicits FcgammaR-effector antibodies that protect against clinical isolates." JCI Insight 1(12).

Wang, B. Z., W. Liu, S. M. Kang, M. Alam, C. Huang, L. Ye, Y. Sun, Y. Li, D. L. Kothe, P. Pushko, T. Dokland, B. F. Haynes, G. Smith, B. H. Hahn and R. W. Compans (2007). "Incorporation of high levels of chimeric human immunodeficiency virus envelope glycoproteins into virus-like particles." J Virol 81(20): 10869-10878.

Wohlbold, T. J., R. Nachbagauer, I. Margine, G. S. Tan, A. Hirsh and F. Krammer (2015). "Vaccination with soluble headless hemagglutinin protects mice from challenge with divergent influenza viruses." Vaccine 33(29): 3314-3321.

The invention claimed is:

1. A process for producing a recombinant Herpes simplex virus-2 (HSV-2) vaccine vector directed against a heterologous antigen, the process comprising:

a) providing a HSV-2 delta-gD2 genome with a deleted glycoprotein D gene (delta gD-2), wherein the deleted gD-2 gene is replaced with a nucleic acid comprising a promoter-red fluorescent protein (RFP) construct, wherein RFP is a nucleic acid encoding a red fluorescent protein;

b) co-transfecting a eukaryotic host cell which phenotypically complements HSV-2 delta-gD-2 by expressing glycoprotein D from HSV-1 (gD-1) on its lipid bilayer with the following:

(i) the HSV-2 delta-gD2 genome of a) and (ii) a linear DNA fragment encoding the heterologous antigen wherein the linear DNA fragment consists of an expression cassette comprising one of the following in the following order: CMV promoter—the heterologous antigen—a polyadenylation signal, wherein the heterologous antigen is codon-optimized for HSV-2 expression;

wherein the linear DNA fragment is flanked on either side by regions homologous to the genomic HSV-2 regions which flank the promoter-RFP construct such that homologous recombination between genomic DNA and the DNA fragment results in the insertion of the expression cassette into the HSV-2 genome between the homologous regions and results in deletion of the promoter-RFP from the HSV-2 genome;

c) propagating the transfected cell of b) under conditions whereby homologous recombination occurs between the HSV-2 delta-gD2genome and the DNA fragment;

d) screening plaques resulting from c) to identify plaques not showing red fluorescence; and e) recovering from those plaques not showing red fluorescence in d) a recombinant HSV-2 virus or virion to obtain the HSV-2 recombinant vaccine vector directed against the heterologous antigen.

2. The process of claim 1, wherein the promoter of the promoter-FP construct is a promoter heterologous to the HSV-2.

3. The process of claim 1, wherein the heterologous antigen is an influenza antigen, an HIV antigen, or a combination thereof, and wherein the influenza antigen is full-length extracellular domain of the hemagglutinin (HA) antigen or is the HA antigen stalk, and the HIV antigen is Env gp145 antigen.

4. The process of claim 1, wherein the heterologous antigen is under control of an upstream CMV promoter and has a downstream SV40 poly-A signal.

5. The process of claim 1, wherein the promoter of the promoter-RFP construct is a promoter of Elongation Factor 1a gene (PEF1$\alpha$) and wherein PEF1$\alpha$ and FP are fused together (PEF1$\alpha$-FP).

6. A recombinant herpes simplex virus-2 (HSV-2) vaccine vector comprising a genome encoding a heterologous antigen, made by the process of claim 1.

7. The recombinant HSV-2 of claim 6, wherein the heterologous antigen is an influenza antigen, an HIV antigen, or a combination thereof, wherein the influenza antigen is full-length extracellular domain of the hemagglutinin (HA) antigen or is the HA antigen stalk, and the HIV antigen is Env gp145 antigen.

8. A vaccine composition comprising the recombinant HSV-2 of claim 7.

9. A pharmaceutical composition comprising the recombinant HSV-2 of claim 7, and a pharmaceutically acceptable carrier.

10. A method of eliciting antibody-dependent cell-mediated cytotoxicity (ADCC) immunity against HSV1 and or HSV-2 and/or a heterologous antigen in a subject, the method comprising administering to the subject an amount of the recombinant HSV-2 of claim 7 effective to elicit the immune response in the subject.

11. A method of treating an influenza infection in a subject, the method comprising administering to the subject an amount of the recombinant HSV-2 of claim 7 effective to treat an influenza infection in the subject, wherein the heterologous antigen is an influenza antigen.

12. A method of treating an HIV infection in a subject, the method comprising administering to the subject an amount of the recombinant HSV-2 of claim 7 effective to treat an HIV infection in a subject, wherein the heterologous antigen is an HIV Env gp145 antigen.

13. A method of vaccinating a subject for influenza infection, the method comprising administering to the subject an amount of the recombinant HSV-2 of claim 7 effective to vaccinate the subject for influenza infection, wherein the heterologous antigen is an influenza HA antigen.

14. A method of vaccinating a subject for HIV infection, the method comprising administering to the subject an amount of the recombinant HSV-2 of claim 7 effective to vaccinate the subject for the HIV infection and, wherein the heterologous antigen is HIV Env gp145 antigen.

15. A method of quantitating a rate or amount of antibody-dependent cell-mediated killing (ADCK) in a population of cells, the method comprising:

infecting a plurality of cells of the population of cells with a red fluorescent protein-expressing recombinant HSV-2 that comprises a genome deleted for the gene encoding HSV-2 gD, under conditions permitting expression of the fluorescent protein in the cells, contacting the plurality of infected cells with an antibody-containing solution and a population of phagocytic immune cells, and quantitating at multiple time points the amount of infected cells among the plurality of infected cells, which exhibit fluorescent protein fluorescence that is greater than the mean intensity of fluorescent protein fluorescence of the plurality of infected cells, and, optionally, quantitating one or more cell viability markers, so as to quantitate over time the amount of live infected cells and thereby quantitate the rate or amount of ADCK in the population of cells.

16. The method of claim 15, wherein the population of immune cells comprises macrophages.

17. The method of claim 15, wherein the antibody-containing solution comprises serum.

18. The method of claim 15, wherein the one or more markers comprises a cell membrane marker, a live/dead marker, or a combination thereof.

19. The method of claim 15, further comprising quantitating at one or more time points the amount of cells exhibiting fluorescent protein fluorescence and, optionally, one or more markers, in a control population of infected cells otherwise identical but not contacted with an antibody-containing solution and comparing the amount or rate quantitated to the amount or rate quantitated for the population of cells contacted with the antibody-containing solution.

* * * * *

SEQUENCE LISTING

```
Sequence total quantity: 20
SEQ ID NO: 1            moltype = AA  length = 393
FEATURE                 Location/Qualifiers
source                  1..393
                        mol_type = protein
                        organism = herpes simplex virus 2
SEQUENCE: 1
MGRLTSGVGT AALLVVAVGL RVVCAKYALA DPSLKMADPN RFRGKNLPVL DQLTDPPGVK   60
RVYHIQPSLE DPFQPPSIPI TVYYAVLERA CRSVLLHAPS EAPQIVRGAS DEARKHTYNL  120
TIAWYRMGDN CAIPITVMEY TECPYNKSLG VCPIRTQPRW SYYDSFSAVS EDNLGFLMHA  180
PAFETAGTYL RLVKINDWTE ITQFILEHRA RASCKYALPL RIPPAACLTS KAYQQGVTVD  240
SIGMLPRFIP ENQRTVALYS LKIAGWHGPK PPYTSTLLPP ELSDTTNATQ PELVPEDPED  300
SALLEDPAGT VSSQIPPNWH IPSIQDVAPH HAPAAPSNPG LIIGALAGST LAVLVIGGIA  360
FWVRRRAQMA PKRLRLPHIR DDDAPPSHQP LFY                              393

SEQ ID NO: 2            moltype = AA  length = 580
FEATURE                 Location/Qualifiers
source                  1..580
```

-continued

```
                        mol_type = protein
                        organism = Human influenzavirus type A
SEQUENCE: 2
MKANLLVLLC ALAAADADTI CIGYHANNST DTVDTVLEKN VTVTHSVNLL EDSHNGKLCR  60
LKGIAPLQLG KCNIAGWLLG NPECDPLLPV RSWSYIVETP NSENGICYPG DFIDYEELRE  120
QLSSVSSFER FEIFPKESSW PNHNTTKGVT AACSHAGKSS FYRNLLWLTE KEGSYPKLKN  180
SYVNKKGKEV LVLWGIHHPS NSKDQQNIYQ NENAYVSVVT SNYNRRFTPE IAERPKVRDQ  240
AGRMNYYWTL LKPGDTIIFE ANGNLIAPRY AFALSRGFGS GIITSNASMH ECNTKCQTPL  300
GAINSSLPFQ NIHPVTIGEC PKYVRSAKLR MVTGLRNIPS IQSRGLFGAI AGFIEGGWTG  360
MIDGWYGYHH QNEQGSGYAA DQKSTQNAIN GITNKVNSVI EKMNIQFTAV GKEFNKLEKR  420
MENLNKKVDD GFLDIWTYNA ELLVLLENER TLDFHDSNVK NLYEKVKSQL KNNAKEIGNG  480
CFEFYHKCDN ECMESVRNGT YDYPKYSEES KLNREKVDGV KLESMGIYQI LAIYSTVASS  540
LVLLVSLGAI SFWMCSNGSL QCRICIDNFR NMRKNTLVST                        580

SEQ ID NO: 3            moltype = DNA  length = 68
FEATURE                 Location/Qualifiers
misc_feature            1..68
                        note = Fwd-pCMV, forward primer
source                  1..68
                        mol_type = other DNA
                        organism = synthetic construct
SEQUENCE: 3
ttttttttcc aagaaatgga ggcctacccg ggttgacatt gattattgac tagttattaa  60
tagtaatc                                                           68

SEQ ID NO: 4            moltype = DNA  length = 39
FEATURE                 Location/Qualifiers
misc_feature            1..39
                        note = Rev-NeoR-Term, primer
source                  1..39
                        mol_type = other DNA
                        organism = synthetic construct
SEQUENCE: 4
ttttttttcc aatctatgga gccccagctg gttctttcc                         39

SEQ ID NO: 5            moltype = DNA  length = 40
FEATURE                 Location/Qualifiers
misc_feature            1..40
                        note = Fwd-Origin, forward primar
source                  1..40
                        mol_type = other DNA
                        organism = synthetic construct
SEQUENCE: 5
ttttttttcc aatttatggg ctgggctgtg tgcacgaacc                        40

SEQ ID NO: 6            moltype = DNA  length = 44
FEATURE                 Location/Qualifiers
misc_feature            1..44
                        note = Rev-AmpR, Reverse primer
source                  1..44
                        mol_type = other DNA
                        organism = synthetic construct
SEQUENCE: 6
ttttttttcc aaaagatggg cagcgcaaaa cgcctaaccc taag                   44

SEQ ID NO: 7            moltype = DNA  length = 44
FEATURE                 Location/Qualifiers
misc_feature            1..44
                        note = LL-V91I-US6, primer
source                  1..44
                        mol_type = other DNA
                        organism = synthetic construct
SEQUENCE: 7
ttttttttcc ataaattgga aagggaacag cgaccaaatg tcac                   44

SEQ ID NO: 8            moltype = DNA  length = 44
FEATURE                 Location/Qualifiers
misc_feature            1..44
                        note = LR-V91I-US6, primer
source                  1..44
                        mol_type = other DNA
                        organism = synthetic construct
SEQUENCE: 8
ttttttttcc atttcttggt gatacgcgat gcacacgaaa aacg                   44

SEQ ID NO: 9            moltype = DNA  length = 38
FEATURE                 Location/Qualifiers
misc_feature            1..38
                        note = RL-V91I-US6, Primer
```

```
source                  1..38
                        mol_type = other DNA
                        organism = synthetic construct
SEQUENCE: 9
ttttttttcc atagattggt tccccgctcc cgtgtacc                               38

SEQ ID NO: 10           moltype = DNA  length = 37
FEATURE                 Location/Qualifiers
misc_feature            1..37
                        note = RR-V91I-US6, primer
source                  1..37
                        mol_type = other DNA
                        organism = synthetic construct
SEQUENCE: 10
ttttttttcc atcttttggc gggggcgcct gtatcgg                                37

SEQ ID NO: 11           moltype = DNA  length = 20
FEATURE                 Location/Qualifiers
misc_feature            1..20
                        note = Neo-Out, Primer
source                  1..20
                        mol_type = other DNA
                        organism = synthetic construct
SEQUENCE: 11
gtataccgtc gacctctagc                                                   20

SEQ ID NO: 12           moltype = DNA  length = 19
FEATURE                 Location/Qualifiers
misc_feature            1..19
                        note = US8-Out, Primer
source                  1..19
                        mol_type = other DNA
                        organism = synthetic construct
SEQUENCE: 12
ggtgacttgg tgcgccgcc                                                    19

SEQ ID NO: 13           moltype = DNA  length = 40
FEATURE                 Location/Qualifiers
misc_feature            1..40
                        note = PCR fragment, plus strand
source                  1..40
                        mol_type = other DNA
                        organism = synthetic construct
SEQUENCE: 13
cgggttgaca ttgattattg actagttatt aatagtaatc                             40

SEQ ID NO: 14           moltype = DNA  length = 20
FEATURE                 Location/Qualifiers
misc_feature            1..20
                        note = PCR fragment, minus strand
source                  1..20
                        mol_type = other DNA
                        organism = synthetic construct
SEQUENCE: 14
agccccagct ggttctttcc                                                   20

SEQ ID NO: 15           moltype = DNA  length = 21
FEATURE                 Location/Qualifiers
misc_feature            1..21
                        note = PCR product, plus strand
source                  1..21
                        mol_type = other DNA
                        organism = synthetic construct
SEQUENCE: 15
gctgggctgt gtgcacgaac c                                                 21

SEQ ID NO: 16           moltype = DNA  length = 25
FEATURE                 Location/Qualifiers
misc_feature            1..25
                        note = PCR product, minus strand
source                  1..25
                        mol_type = other DNA
                        organism = synthetic construct
SEQUENCE: 16
gcagcgcaaa acgcctaacc ctaag                                             25

SEQ ID NO: 17           moltype = DNA  length = 25
FEATURE                 Location/Qualifiers
misc_feature            1..25
```

-continued

```
                        note = PCR product, plus strand
source                  1..25
                        mol_type = other DNA
                        organism = synthetic construct
SEQUENCE: 17
aaagggaaca gcgaccaaat gtcac                                   25

SEQ ID NO: 18           moltype = DNA  length = 25
FEATURE                 Location/Qualifiers
misc_feature            1..25
                        note = PCR product, minus strand
source                  1..25
                        mol_type = other DNA
                        organism = synthetic construct
SEQUENCE: 18
tgatacgcga tgcacacgaa aaacg                                   25

SEQ ID NO: 19           moltype = DNA  length = 19
FEATURE                 Location/Qualifiers
misc_feature            1..19
                        note = PCR product, plus strand
source                  1..19
                        mol_type = other DNA
                        organism = synthetic construct
SEQUENCE: 19
ttccccgctc ccgtgtacc                                          19

SEQ ID NO: 20           moltype = DNA  length = 18
FEATURE                 Location/Qualifiers
misc_feature            1..18
                        note = PCR product, minus strand
source                  1..18
                        mol_type = other DNA
                        organism = synthetic construct
SEQUENCE: 20
cgggggcgcc tgtatcgg                                           18
```